US008466157B2

(12) United States Patent
Lawrence et al.

(10) Patent No.: US 8,466,157 B2
(45) Date of Patent: Jun. 18, 2013

(54) PROTEASOME INHIBITORS HAVING CHYMOTRYPSIN-LIKE ACTIVITY

(75) Inventors: Harshani Lawrence, Tampa, FL (US); Yiyu Ge, Tampa, FL (US); Said M. Sebti, Tampa, FL (US); Wayne Guida, St. Petersburg, FL (US)

(73) Assignees: University of South Florida, Tampa, FL (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 13/225,976

(22) Filed: Sep. 6, 2011

(65) Prior Publication Data

US 2012/0142917 A1 Jun. 7, 2012

Related U.S. Application Data

(63) Continuation of application No. PCT/US2010/026531, filed on Mar. 8, 2010.

(60) Provisional application No. 61/158,016, filed on Mar. 6, 2009.

(51) Int. Cl.
*A61K 31/47* (2006.01)
*A61K 31/497* (2006.01)
*C07D 215/00* (2006.01)
*C07D 333/08* (2006.01)
*C07D 401/00* (2006.01)

(52) U.S. Cl.
USPC ...... 514/253.01; 514/312; 544/360; 546/153; 549/80

(58) Field of Classification Search
USPC . 514/253.01, 312; 544/360; 546/153; 549/80
See application file for complete search history.

(56) References Cited

U.S. PATENT DOCUMENTS

| 2005/0282818 A1 | 12/2005 | Ramesh et al. |
| 2007/0066600 A1 | 3/2007 | Caldirola et al. |
| 2007/0203236 A1 | 8/2007 | Smith et al. |

FOREIGN PATENT DOCUMENTS

SU  1558901 A1  4/1990

OTHER PUBLICATIONS

Patani et al., Chem Rev, 1996, vol. 96 (8), especially p. 3149.*
Xu, et al, PLoS One (2009), 4(3), pp. 1-12.*
Xu, et al., PLos One (2009), 4(3), pp. 1-12.*
International Search Report for PCT Application No. PCT/US2010/026531 with a mailing date of Nov. 29, 2010.
Sterz, I. von Metzler, J.C. Hahne, B. Lamottke, J. Rademacher, U. Heider, E. Terpos, O. Sezer, The Potential of Proteasome Inhibitors in Cancer Therapy, Expert Opin. Invest. Drugs 2008, 17(6), 879-895.
Bennett and C.J. Kirk, Development of Proteasome Inhibitors in Oncology and Autoimmune Diseases, Current Opinion in Drug Discovery &Development, 2008, 11(5), 616-625.
Obafemi, C.A., Studies in the Heterocyclic Compounds: I. Some 2-Thiophenesulfonyl Derivatives, Phosphorus and Sulfur , 1980, 8, 197-200.
Arnone, A., Direct Amination of Naphthazarin, Juglone, and Some Derivatives, Synth. Commun., 2007, 37(15), 2569-2577.
Matsubara, T. Doko, R. Uetake and S. Kobayashi, Enesulfonamides as Nucleophiles in Catalytic Asymmetric Reactions, Angew. Chem. Int. Ed, 2007, 46, 3047-3050.
Altland, H.W. and Briffa, Jr., B. F., 1,4-Addition of Triazolium Thiolates to Quinones, J. Org. Chem., 1985, 50, 433-437.
Jung, L., Holle L., and Dalton, W.S., Discovery, Development, and Clinical Applications of Bortezomib, Oncology, 2004, 18(14), 4-13.
Adams, R. and Whitaker, L., Quinone Imides. XXXIX. Adducts of Quinone Monoimides and Conversion of Active Methylene Adducts to Benzofurans, J. Am. Chem. Soc., 1956, 78, 658-663.
Esquivias, R. G. Arrayas and J. C. Carretero, Catalytic Asymmetric Inverse-Electron-Demand Diels-Alder Reaction of N-Sulfonyl-1-Aza-1,3-Dienes, J. Am. Chem. Soc., 2007, 129, 1480-1481.
Adams, R. and Wankel, R.A., Quinone Imides. III. 1,4-Naphthoquinone Disulfonimides, J. Am. Chem. Soc., 1951, 73, 131-134.

* cited by examiner

*Primary Examiner* — Susannah Chung
(74) *Attorney, Agent, or Firm* — Michael L. Lawson; Michael McGaw; Smith & Hopen, P.A.

(57) ABSTRACT

Disclosed herein is the use of HLM-008182, as well as its analogues formed via in-house synthesis, as a potent proteasome inhibitors. A new method was developed for HLM-008182 through a four-step protocol and the method was further optimized to a two step protocol. The synthesis in both protocols was regioselective with $TiCl_4$. The reaction was highly efficient with microwave assisted heating and THF as solvent. The modification around the molecule HLM-008182 established primary SAR, indicating that the proteasome inhibition activity was a function of the 2-side chain.

18 Claims, 9 Drawing Sheets

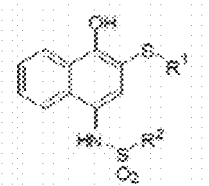

Figure 11

| Entry | Compound | R¹ | R² | IC₅₀ᵃ (μM) | IC₅₀ᵇ (μM) |
|---|---|---|---|---|---|
| 1 | HLM-008182ᶜ | CH₂COOH | (furan) | 0.65±0.40 | |
| 2 | 9a | CH₂COOC₂H₅ | (furan) | 7.33±2.82 | NTᵈ |
| 3 | 9b | (CH₂)₂COOCH₃ | (furan) | 4.99±2.08 | NT |
| 4 | 9c | CH₂COOC₂H₅ | (furan) | 5.27±2.23 | NT |
| 5 | 9e | CH₂COOC₂H₅ | (phenyl) | 3.57±1.53 | NT |
| 6 | 10aᶜ | CH₂COOH | (furan) | 1.30±0.76 | 7.3, 8.9 |
| 7 | 10b | (CH₂)₂COOH | (furan) | >10 | NT |
| 8 | 10c | CH₂COOH | (furan) | 2.08±0.78 | NT |
| 9 | 14d | (structure) | (furan) | 4.25±2.13 | 6.4, 6.4 |
| 10 | 14e | (structure) | (furan) | 4.22±2.73 | 4.8, 5.1 |
| 11 | 14h | (CH₂)₂CONHCH(CH₃)₂ | (furan) | 7.3±1.30 | NT |
| 12 | 14l | (structure) | (furan) | 4.05±2.64 | NT |
| 13 | 14m | (CH₂)₂COOCH₃ | (structure) | 1.18±0.30 | NT |
| 14 | 14n | CH₂COOH | (structure) | 2.07±0.55 | 25, 17.4 |
| 15 | 14o | CH₂COOH | (structure) | 2.07±0.69 | 8, 10 |
| 16 | 14p | CH₂COOH | (structure) | 3.75±0.30 | NT |

PROTEASOME INHIBITORS HAVING CHYMOTRYPSIN-LIKE ACTIVITY

CROSS REFERENCE TO RELATED APPLICATIONS

This application is a continuation of prior filed International Application, Ser. No. PCT/US2010/026531 filed Mar. 8, 2010, which claims priority to U.S. provisional patent application No. 61/158,016 filed Mar. 6, 2009 which is hereby incorporated by reference into this disclosure.

GOVERNMENT SUPPORT

This invention was made with government support under Grant No. 1PO1 CA118210-03 awarded by the National Institutes of Health. The government therefore has rights in the invention.

FIELD OF INVENTION

This invention relates to compounds for use in, inter alia, cancer treatment.

BACKGROUND OF THE INVENTION

A proteasome is a multi subunit proteolytic complex that degrades ubiquitinylated proteins into small peptides. The molecular and functional characteristics of the ubiquitin-proteasome system (UPS) has been studied by several groups showing that 26S proteasome is involved in a diverse array of biological processes including cell cycle progression, apoptosis, DNA repair, immune response, signal transduction, transcription, metabolism, protein quality control and developmental programs. Proteins that control such processes are subjected to proteolysis in a precise, rapid and timely manner by the 26S proteasome. Thus UPS has been reported to play a crucial role in tumorigenesis, inflammation and autoimmunity. The anticancer activity of the proteasome inhibitors has shown selective apoptosis in malignant cells, and represented a new class of antineoplastic agents. Subsequently proteasome has emerged as a promising target in search of cancer therapeutics in the recent years. Bortezomib (Velcade), Salinosporamide A, Carfilzomib represent three classes of proteasome inhibitors that have been clinically approved or in clinical trial for treatment of multiple myeloma and/or mantle cell lymphoma. However, drug resistance caused by several mechanism has emerged as a major challenge for protreasome associated cancer therapy. Studies with combination of the two agents (Bortezomib and Salinosporamide A) have suggested that combination of agents that have qualitatively different mechanism of action may become the solution to the drug resistance. Therefore developing novel molecules as proteasome inhibitors is essential for cancer therapy.

SUMMARY OF INVENTION

This invention relates to the field of cancer therapy. The invention includes a small molecule HLM-008182, identified from 20,000 in-house ChemDiv library, was confirmed by in-house synthesis as a proteasome chymotrypsin-like inhibitor. A new method to build up hydronaphthoquinone scaffold was developed for further library synthesis. A primary SAR was studied by structural modification around HLM-008182 molecule.

BRIEF DESCRIPTION OF THE DRAWINGS

For a fuller understanding of the invention, reference should be made to the following detailed description, taken in connection with the accompanying drawings, in which:

FIG. 11: Modifications on 2-substitution and 4-sulfonamide.

DETAILED DESCRIPTION OF THE PREFERRED EMBODIMENT

Figure 1:
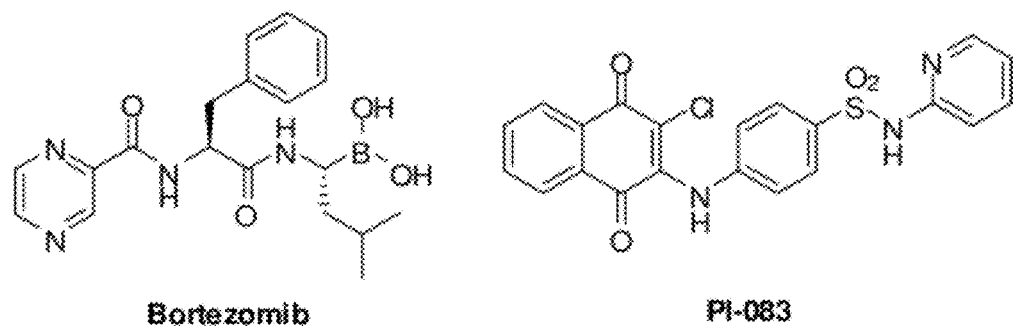
FIG. 1: structure of Bortezomib (clinically approved) and PI-083.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

This invention includes compositions for use as proteasome inhibitors which can be used to block cancer cell growth or proliferation and/or inducing cancer cell death. Proteasome inhibitors within the scope of the invention include small molecule compounds comprising a hydronaphthoquinine sulfonamide scaffold.

In one embodiment, a proteasome inhibitor of the invention has the structure shown in formula I:

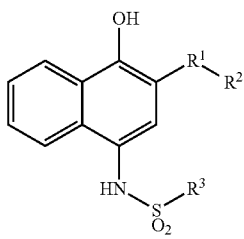

(I)

In another embodiment, a proteasome inhibitor of the invention has the structure shown in formula II:

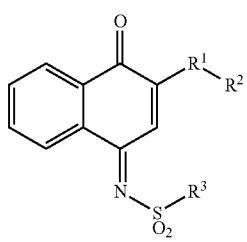

(II)

In a general embodiment: $R^1$ is selected from the group consisting of N, O, S, P, B, Cl, Br, I, heteroalkyl, heterocycloalkyl, heteroaryl, heteroarylcarbonyl, heteroaryloxycarbonyl, heterocycloalkoxy and heterocycloalkoxycarbonyl.

$R^2$ is selected from the group consisting of H, alkyl, alkoxy, cycloalkyl, cycloalkoxy, aryl, aryloxy, alkylcarbonyl, alkoxycarbonyl, cycloalkylcarbonyl, cycloalkoxycarbonyl, arylcarbonyl and aryloxycarbonyl.

$R^3$ is selected from the group consisting of alkyl, alkoxy, cycloalkyl, cycloalkoxy, aryl, aryloxy, alkylcarbonyl, alkoxycarbonyl, cycloalkylcarbonyl, cycloalkoxycarbonyl, arylcarbonyl, aryloxycarbonyl, heteroalkyl, heterocycloalkyl, heteroaryl, heteroarylcarbonyl, heteroaryloxycarbonyl, heterocycloalkoxy and heterocycloalkoxycarbonyl.

In an illustrative embodiment: $R^1$ is C or a heteroatom selected from N, O, S, P, B, Cl, Br and I; and $R^2$ is selected from COOH, $CH_2COOH$, $CH_2COOC_2H_5$, $(CH_2)_2COOCH_3$, $(CH_2)_2COOH$, $(CH_2)_2CONHCH(CH_2)_2$, $CH(CH_3)COOH$, $(CH_2)_2$—$B(OH)_2$, $CH$—$(CH_2)_n$—$B(OH)_2$, $CH$—$(CH3)$-$B(OH)_2$ and $B(OH)_2$.

$R^2$ can also be selected from the group consisting of

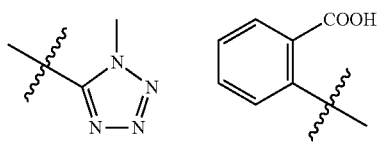

and

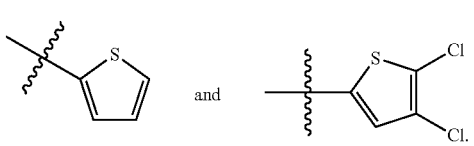 [SMILES: *c1cccs1 ; *c1cc(Cl)c(Cl)s1]

$R^3$ is selected from

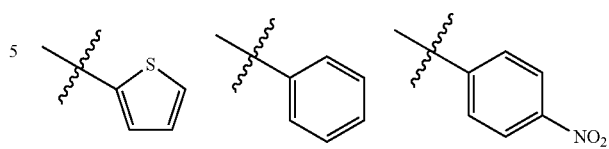

In a first illustrative embodiment, when $R^2$ is $CH_2COOH$ then $R^3$ is selected from:

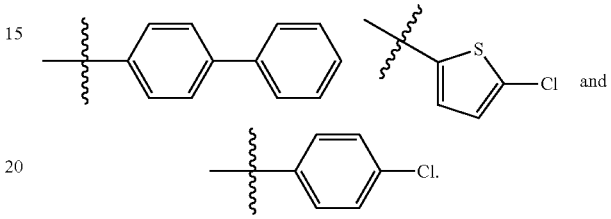

In a second illustrative embodiment, when $R^2$ is $CH_2COOC_2H_5$ then $R^3$ is selected from

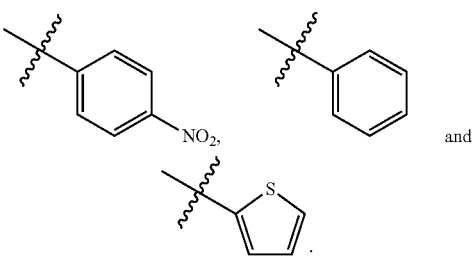

In a third illustrative embodiment, when $R^2$ is $(CH_2)_2COOCH_3$ then $R^3$ is selected from In a fourth illustrative embodiment, when $R^2$ is $(CH_2)_2COOH$ then $R^3$ is

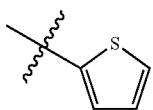 [SMILES: *c1cccs1]

In a fifth illustrative embodiment, when $R^2$ is $(CH_2)_2CONHCH(CH_2)_2$ then $R^3$ is

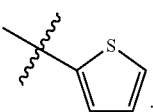

In a sixth illustrative embodiment, when $R^2$ is $CH(CH_3)COOH$ then $R^3$ is selected from

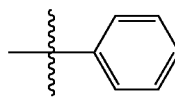 and 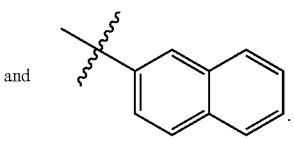

In a seventh illustrative embodiment, when $R^2$ is

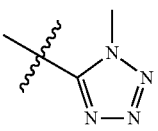 [SMILES: *c1nnnn1C]

then $R^3$ is

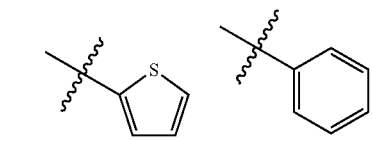

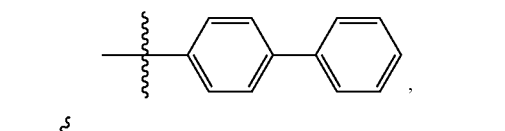

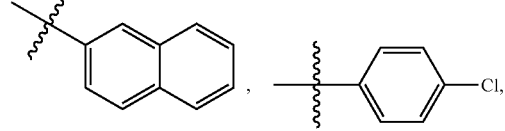

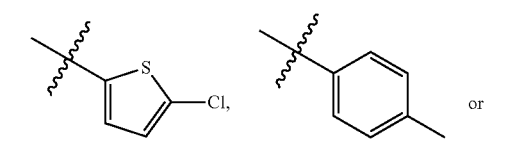 or

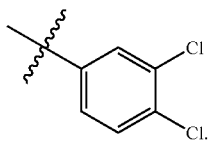

In an eight illustrative embodiment, when $R^2$ is

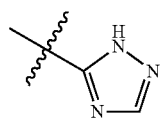

then $R^3$ is

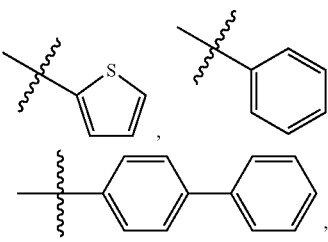

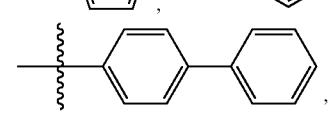

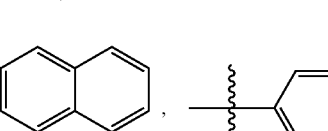

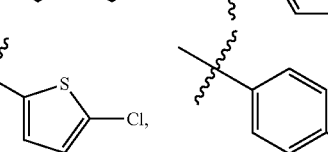

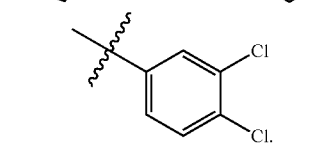

In a ninth illustrative embodiment, when $R^2$ is

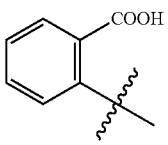 [SMILES: *c1ccccc1C(=O)O]

then $R^3$ is selected from:

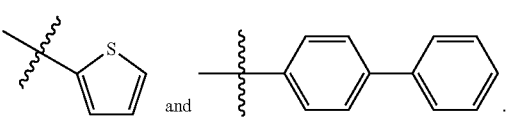 [SMILES: *c1cccs1 ; *c1ccc(-c2ccccc2)cc1]

In a tenth illustrative embodiment, when $R^2$ is

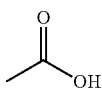

then $R^3$ is

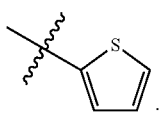

Also contemplated are molecules wherein boronic acids (e.g. $(CH_2)_2$—$B(OH)_2$, CH—$(CH_2)_n$—$B(OH)_2$, CH—$(CH3)$-$B(OH)_2$ and $B(OH)_2$) are incorporated as mimics of carboxylic acids as disclosed herein.

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to X carbon atoms wherein X is any positive integer. For example, $C_{1-6}$ alkyl means straight or branched chain alkyl groups containing from one up to 6 carbon atoms.

Alkoxy means an alkyl-O-group in which the alkyl group is as described herein.

Cycloalkyl includes a nonaromatic monocyclic or multicyclic ring system, including fused and Spiro rings, of from about three to about 10 carbon atoms. A cyclic alkyl may optionally be partially unsaturated.

Cycloalkoxy means a cycloalkyl-O-group in which cycloalkyl is as defined herein.

Aryl means an aromatic monocyclic or multicyclic carbocyclic ring system, including fused and spiro rings, containing from about six to about 14 carbon atoms.

Aryloxy means an aryl-O-group in which the aryl group is as described herein.

Alkylcarbonyl means a RC(O)— group where $R^2$ or $R^3$ is an alkyl group as previously described.

Alkoxycarbonyl means an ROC(O)— group where $R^2$ or $R^3$ is an alkyl group as previously described.

Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms wherein the nitrogen and sulphur atoms may optionally be oxidized, i.e., in the form of an N-oxide or an S-oxide.

Heterocycloalkyl means a monocyclic or multicyclic ring system (which may be saturated or partially unsaturated), including fused and spiro rings, of about five to about 10 elements wherein one or more of the elements in the ring system is an element other than carbon and is a heteroatom.

Heteroaryl means a five to about a 14-membered aromatic monocyclic or multicyclic hydrocarbon ring system, including fused and spiro rings, in which one or more of the elements in the ring system is an element other than carbon and is a heteroatom and wherein an N atom may be in the form of an N-oxide.

Arylcarbonyl means an aryl-CO-group in which the aryl group is as described herein.

Heteroarylcarbonyl means a heteroaryl-CO-group in which the heteroaryl group is as described herein and heterocycloalkylcarbonyl means a heterocycloalkyl-CO-group in which the heterocycloalkyl group is as described herein.

Aryloxycarbonyl means an ROC(O)— group where $R^2$ or $R^3$ is an aryl group as previously described. Heteroaryloxycarbonyl means an ROC(O)— group where $R^2$ or $R^3$ is a heteroaryl group as previously described.

Heterocycloalkoxy means a heterocycloalkyl-O— group in which the heterocycloalkyl group is as previously described.

Heterocycloalkoxycarbonyl means an ROC(O)— group where $R^1$, $R^2$ or $R^3$ is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, benzyl, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, isoxazolyl, thiazolyl, pyrazolyl, pyridyl, pyrimidyl, purinyl, indolyl, quinolinyl, isoquinolinyl, benzoquinolinyl, carbazolyl, and diazaphenanthrenyl.

Heteroatom means any atom that is not hydrogen (H) or carbon (C); in preferred embodiments, a heteroatom refers to nitrogen (N), oxygen (O), sulfur (C), phosphorous (P), boron (B), chlorine (Cl), bromine (Br), and iodine (I).

The subject invention also concerns compositions comprising a proteasome inhibitor of the invention, or a salt thereof, in a pharmaceutically acceptable carrier or diluent.

The inventors have identified compound PI-083 (FIG. 1) as a proteasome inhibitor that exhibits selective inhibition against three different human tumor cell lines (breast, pancreatic and ovarian) over normal cells. As a follow-up for pursuing small molecule proteasome inhibitors, HLM-008182 (1) (FIG. 2) was identified as a 'hit' from a 20,000 in-house ChemDiv library that shows potent inhibition against chymotrypsin-like proteasome activity with an $IC_{50}$ value of 0.65±0.40 μM.

Figure 2:
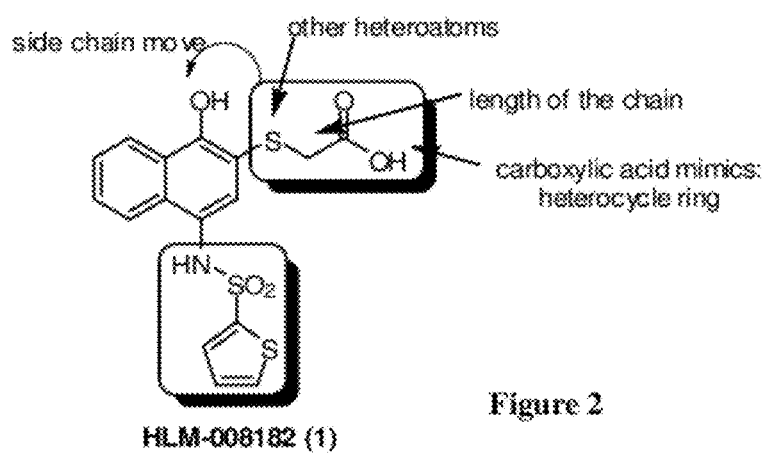
FIG. 2: chemical modification around molecule of HLM-008182 (1)

Synthesis of HLM-008182 (1) has not yet been reported in the chemical literature. This work highlights the synthesis of HLM008182 and modifications around the molecule to obtain a desirable drug-like molecule for proteasome inhibition and associated studies. The hydronaphthoquinone pharmacophore in HLM-008182 (I) has high structural diversity that was exploited for focused library synthesis and represents an attractive small molecule for medicinal chemistry. The modification is primarily focused on the 2 and 4 positions (FIG. 2).

Figure 3:
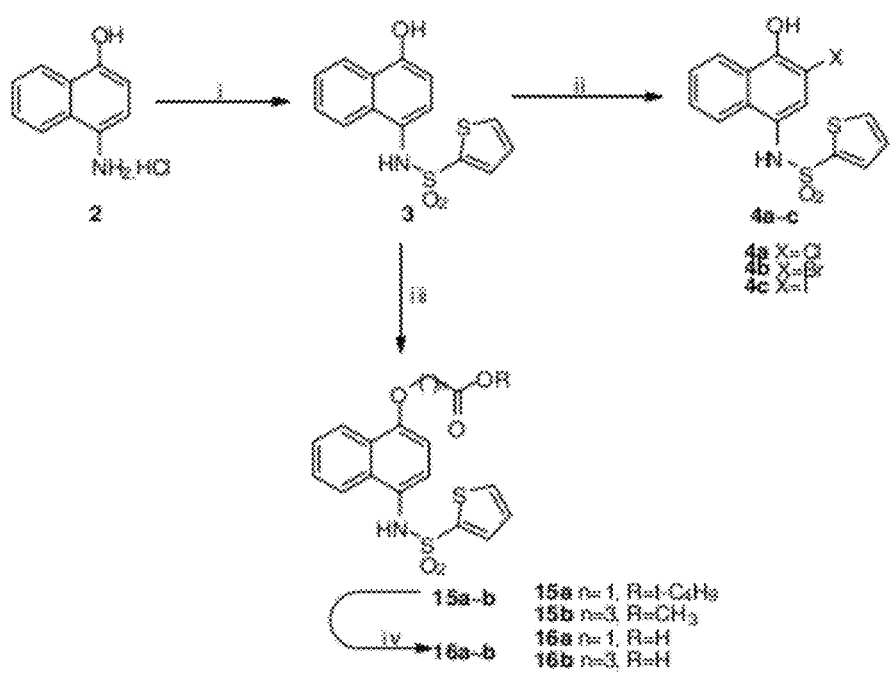
FIG. 3: synthesis scheme of compounds 4a-4-c, 15a-b and 16a-b. Reagents and conditions: i) thiophene-2-sulfonyl chloride, $Et_3N$, dichloromethylene; ii) $H_2O_2$, HCl, dioxane for 4a; $Br_2$ or $I_2$, TEA, DMF, 0° C. to r.t. for 4b, c; iii) $Br(CH_2)_n$ COOR, DBU, DMF; iv) conc. HCl, dioxane.
Figure 4:
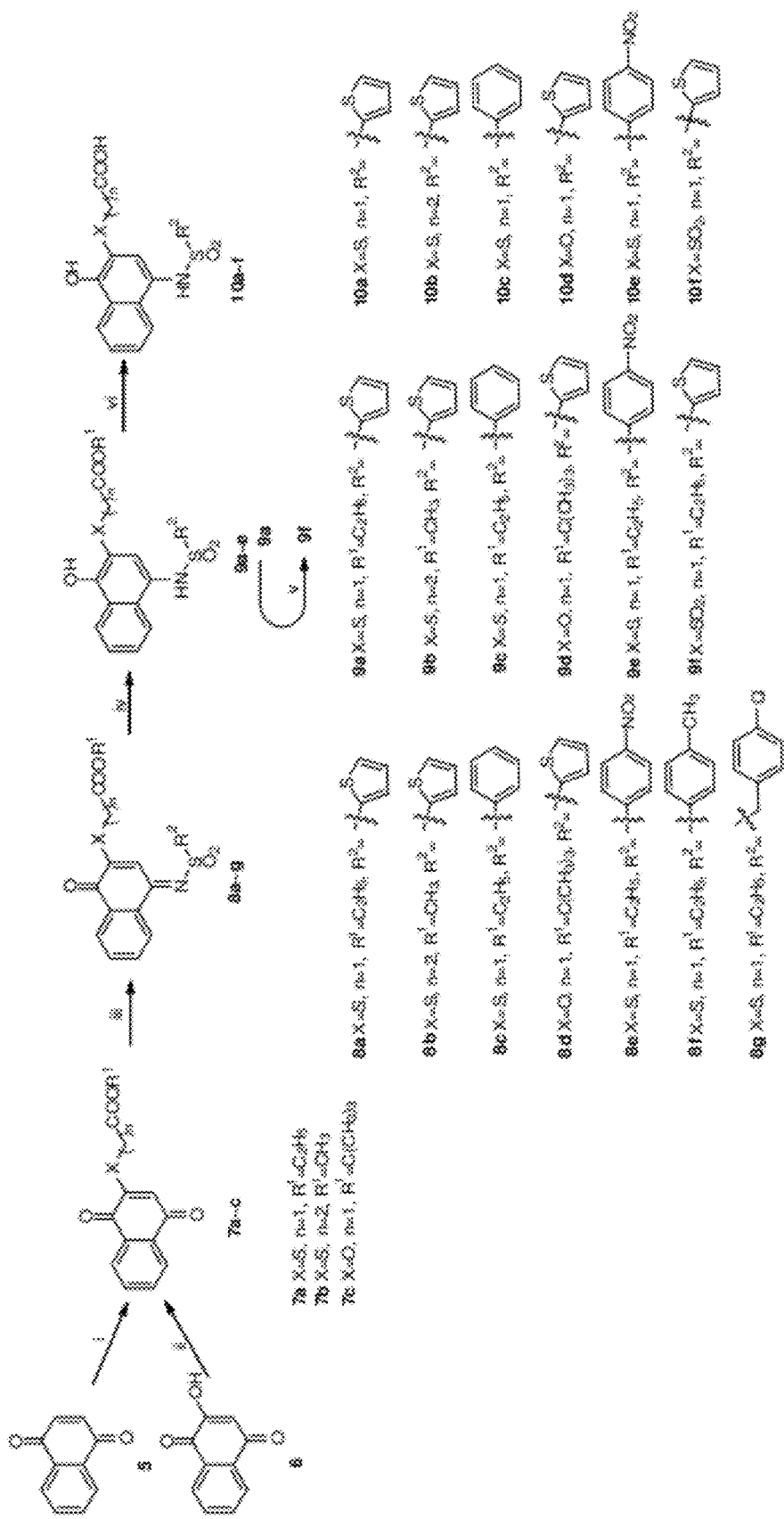
FIG. 4: synthesis scheme of compounds 7a-c, 8a-g, 9a-f and 10a-f. Reagents and conditions: i) $HS(CH_2)_n COOR^1$, ethanol, r.t.; ii) $BrCH_2COOBu$-t, $Ag_2O$, $CHCl_3$, cat. KI, reflux, overnight; iii) $R^2SO_2NH_2$, $TiCl_4.2THF$, $Et_3N$, DCM or THF, microwave, 60° C.; iv) $Na_2S_2O_4$, THF or EtOAc, $H_2O$, r.t.; v) conc. HCl, dioxane, r.t or microwave, 100° C.; vi) oxone/$H_2O$/acetone, r.t., overnight.
Figure 5:
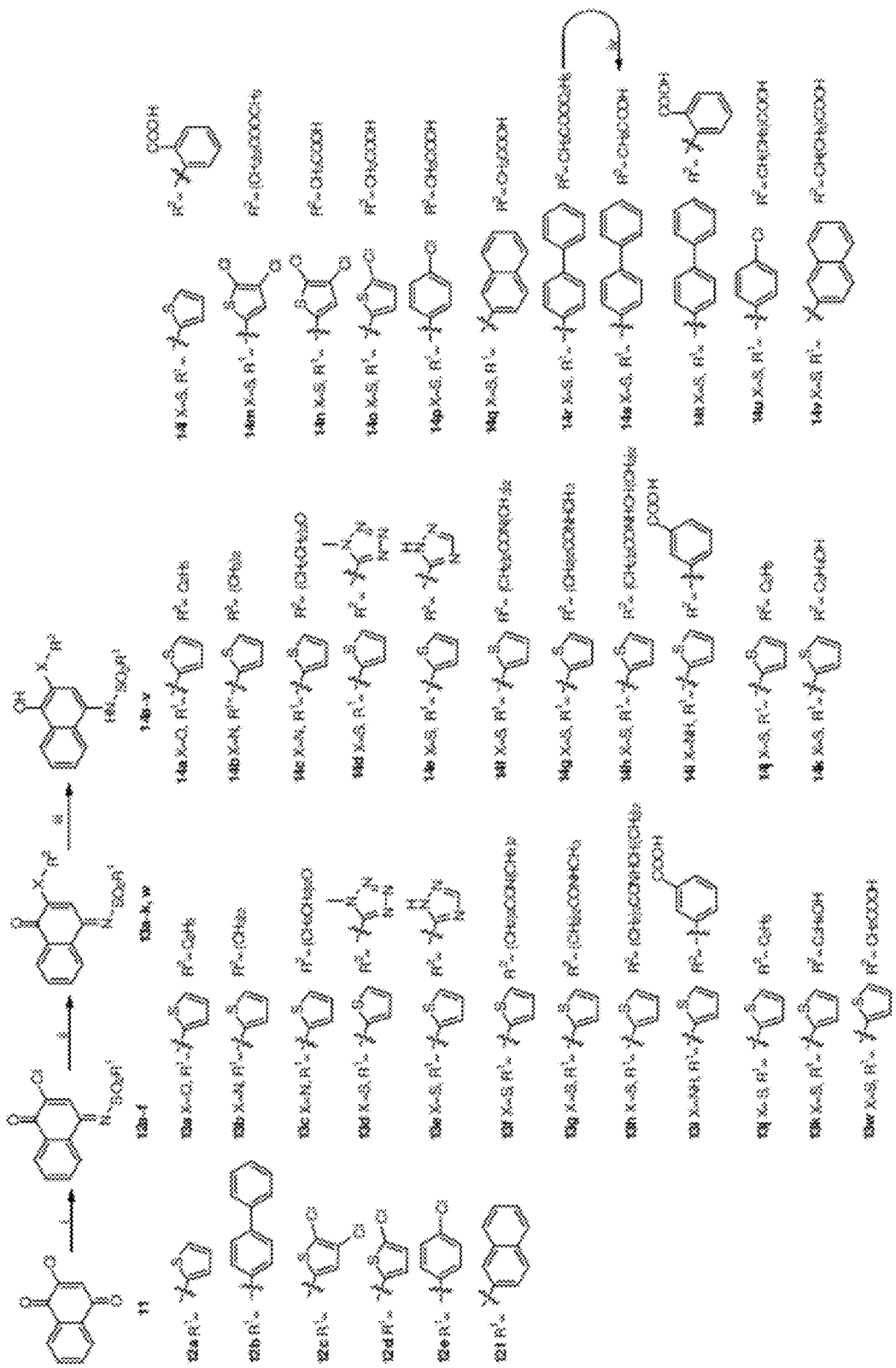
FIG. 5: synthesis scheme of compounds 12a-f, 13a-k and w, 14a-v. Reagents and conditions: i) $R^1SO_2NH_2$, $TiCl_4.2THF$, $Et_3N$, THF, microwave, 60° C.; ii) $NaOC_2H_5$, $C_2H_5OH$ for 13a; $NR^2$, THF for 13b~c, 13i; $HSR^2$, Py., THF for 13d~h, 13j~k; iii) $Na_2S_2O_4$, EtOAc and $H_2O$, shaking in separation funnel; iv) conc. HCl, dioxane, r.t.

Starting from 4-aminonaphth-1-ol hydrochloride salt 2, compound 4a was synthesized through a one pot oxidation-addition reaction of the intermediate 3 similarly to the reported procedure (see Altland, H. W. and Briffa, Jr., B. F., *J. Org. Chem.*, 1985, 50, 433-437) except in the presence of hydrogen peroxide and 4M HCl dioxane solution. 4b and 4c were synthesized in the presence of bromine or iodine in DMF (FIG. 3) according to the reported method (U.S.S.R. patent 1,558,901, 1990) except that the reaction gave the hydronaphthoquinone sulfonamide derivatives (See $^1$H-NMR and HRMS of 4b and 4c). Compound 10a~e, 14a~t were synthesized from commercially available 1,4-naphthoquinone (5), 2-hydroxyl-1,4-naphthoquinone (6) or 2-chloro-1,4-naphthoquinone (11) respectively (FIGS. 4 and 5). As shown in the FIG. 4, ethyl mercaptoacetate or methyl 3-mercaptopropionate was added to 2 eq. of the starting material 1,4-naphthoquinone (5) affording precursors 7a~b. The precursor 7c was obtained by nucleophilic substitution of 2-hydroxyl-1,4-naphthoquinone (6) with tertiary butyl bromoacetate using silver oxide as a base. The various sulfonamides ($R^2SO_2NH_2$), either commercially available or synthesized according to literature method (Obafemi, C. A., *Phosphorus and Sulfur and the Related Elements*, 1980, 8, 197-199), were regioselectively coupled with the intermediate 7a~c in the presence of titanium (IV) chloride and triethylamine with microwave assisted heating to obtain the library 8. The key intermediates 8 were then reduced by sodium hydrosulfite to hydronaphthoquinone sulfonamide derivatives 9, followed by hydrolysis in a mixture of concentrated HCl and dioxane (1:1) to give the final compounds 10a~d. The compound 10f was obtained by oxidation of compound 9a with oxone followed by acidic hydrolysis. The compound 9e was a 'side product' from coupling 4-nitrobenzenesulfonamide to the intermediate 7a in the presence of titanium (IV) chloride and triethylamine using dichloromethylene as the solvent.

Figure 6:
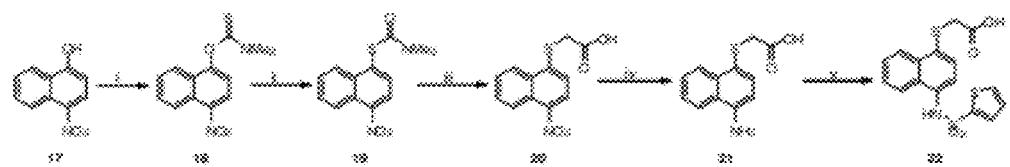
FIG. 6: synthesis scheme of compounds 18-22. Reagents and conditions: i) $Me_2NCSCl$, $K_2CO_3$, NMP, 50° C.; ii) NMP, microwave, 180° C.; iii) (1) 4 eq. KOH, $CH_3OH$, (2) $BrCH_2COOC(CH_3)_3$; iv) $H_2$ (40 bar), Pd/C, $CH_3OH$, r.t.; v) (1) Py, THF, $H_2O$, (2) thiophene-2-sulfonyl chloride.

The library 14 was synthesized, as shown in FIG. 5, via coupling various sulfonamides to 2-chloro-1,4-naphthoquinone (11) using the same procedure as for the intermediate 8, followed by substitution of 2-chlorine with the various nucleophiles with or without base. Moving the 2-side chain to the position of Cl was achieved according to FIGS. 3 and 6. 16a~b were obtained by directly alkylating compound 3 with 2-bromo acetate or 4-bromo butyrate followed by acidic hydrolysis. Newman rearrangement was applied to build up 1-S scaffold (as in intermediate 19) in approaching to compound 22 (FIG. 6). Hydrolysis of 19 in a 4 eq. KOH solution followed by alkylation with tert-butyl 2-bromo acetate without separating the 1-SH intermediate directly gave an acid derivative 20. Hydrogenation of 4-nitro group followed by sulfonylation with thiophene-2-sulfonyl chloride and pyridine in an aqueous solution afforded compound 22.

Although there were reported protocols for naphthoquinone sulfonimide synthesis (Adams, R. and Whitaker, L., *J. Am. Chem. Soc.*, 1956, 78, 658-663; Adams, R. and Wankel, R. A., *J. Am. Chem. Soc.*, 1951, 73, 131-134), these protocols failed to afford HLM-008182. The inventors successfully developed the synthesis of hydronaphthoquinone sulfonamide disclosed herein. Starting from commercially available 1,4-naphthoquinone (5), the hydronaphthoquinone sulfonamide scaffold was built up through addition-oxidation of the starting material 5 with thio-nucleophiles, coupling sulfonamides to the corresponding 1,4-naphthoquinone derivatives, reduction and hydrolysis. The synthesis method was further optimized to a two step protocol. Starting from commercially available 2-chloro-1,4-naphthoquinone (11), the scaffold was formed through coupling sulfonamides to the starting material 11, nucleophilic substitution followed by reduction.

In the protocol using 5 as the starting material (FIG. 4), the key step to afford the intermediates 8 gave several products according to TLC with dichloromethylene as the reaction solvent. In addition to the intermediates 8, the reduced products (see structure of 9) were isolated as well via flash chromatography and identified by $^1$H-NMR and HRMS-(+). In the reaction attempting 8e, only the reduced form 9e was obtained in a low yield. This type of 'side reaction' made the isolation of the intermediates 8 laborious and the library synthesis a time consuming job. The mechanism of the unexpected 'side reaction' has not been unknown yet.

Figure 9:
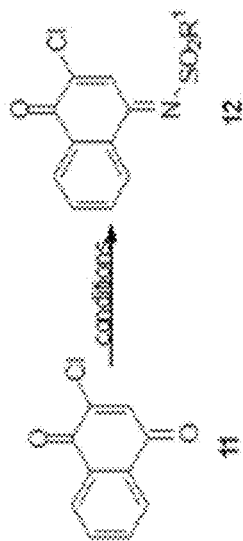
FIG. 9: optimization of coupling conditions for the key intermediate 12.

FIG. 5 represented an optimized procedure for synthesis of HLM-008182 and its analogues. The key intermediates 12 were purified by either re-crystallization or trituration from appropriate solvents, thus more convenient for library synthesis. The step for the intermediates 12 was more efficient with microwave assisted heating than conventional heating (FIG. 9, entry 2 vs 3). The yield of the coupling reaction was significantly improved when dichloromethylene was replaced by THF (FIG. 9, entry 2 vs 4, entry 5 vs 6). For example, the yields for compound 12e and f (FIG. 9, entry 7 and 8) were improved to 61.8% and 77.9% respectively when THF was utilized. When aliphatic thiol was used in the subsequent nucleophilic substitution, the products 13, in situ, were partially reduced to the final compounds 14 in the presence of aliphatic thiol giving mixtures of 13 and 14 in a certain ratio. However, the single component of the final hydronaphthoquinone sulfonamide 14 (FIG. 7) was obtained without separation of the mixtures by directly treating the mixtures with sodium hydrosulfite in biphasic solution of ethyl acetate and water. The in situ reduction was not observed with non-reductive nucleophiles such as alcohols (compound 13a) and amines (compound 13b, c, i). However, attempts to reduce these compounds to hydronaphthoquinone sulfonamide derivatives did not get the final products as a single component due to the rapid oxidation of the reduced product when exposed to air. It is notable that compound 10a was oxidized to naphthoquinone sulfonimide derivative when attempting to dissolve it in $CDCl_3$ in a NMR tube by the aid of sonication. The mechanism was not clear although the oxidation could be caused by sonication which facilitated the oxidation in $CDCl_3$.

Figure 7:
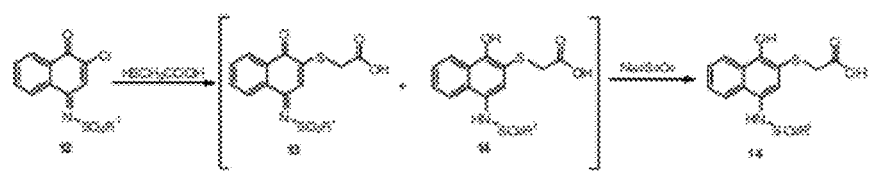
FIG. 7: in situ reduction of naphthoquinone sulfonimide derivatives 13 to the final hydronaphthoquinone sulfonamide derivatives 14.
Figure 8:
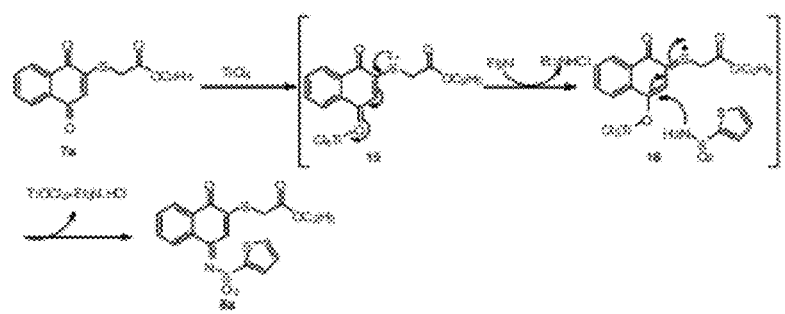
FIG. 8: proposed mechanism for regioselective coupling of sulfonamide to 1,4-naphthoquinone derivative using compound 7a as an example.

Coupling the various sulfonamides to 1,4-naphthoquinone derivatives 7 or 11 in the presence of titanium chloride and triethylamine was a key step to building up naphthoquinone sulfonimide scalffold. A $TiCl_4$-$Et_3N$ system has been widely used in forming sulfonimides[34, 35] through activation of the reactive ketone by forming a $TiCl_4$-ketone complex. In 1,4-naphthoquinone derivatives 7 or 11, the participation of 2-sulfur, oxygen or chlorine atom facilitated $TiCl_4$ to form the complex with 4-carbonyl rather than 1-carbonyl (FIG. 7, 15). The complex was stabilized by the p-π conjugation system formed between the lone pair electrons on 2-sulfur, oxygen or chlorine and the naphthoquinone ring (FIG. 8, 15→16). Therefore in the presence of $TiCl_4$, the sulfonamides were regioselectively coupled to 1,4-naphthoquinone derivatives 7 or 11 at the 4 position. In contrast to $TiCl_4$ assist, the regioselectivity, as reported (Arnone, A., *Synth. Commun.*, 2007, 37, 2569-2577), was reversed to 1-carbonyl when a coupling occurred under a basic condition because the nucleophilicity of 4-carbonyl was dramatically decreased by the participation of the 2-oxygen. The coupling procedure was not successful when there was a methyl group at the 3 position due to the steric hindrance effect.

Figure 10:
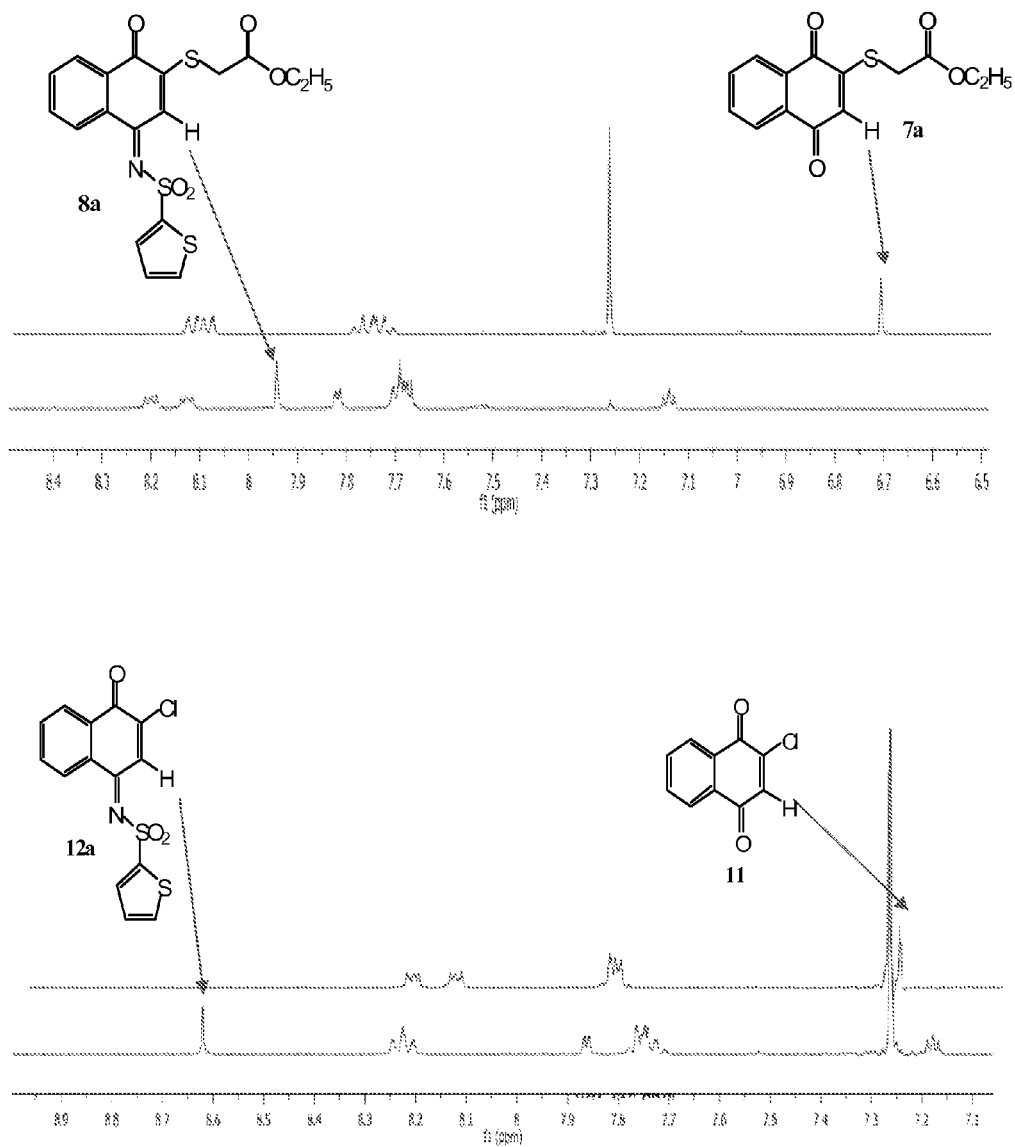
FIG. 10: A, chemical shift (in $CDCl_3$, 400 Hz) of 3-H in compound 7a (upper) and 8a (lower); B, chemical shift of 3-H in compound 11 (upper) and 12a (lower).

The regioselectivity was confirmed by 1H-NMR in that the chemical shift of 3-H significantly shifted down field from 6.70 ppm in 7a to 7.94 ppm in 8a and from 7.24 ppm in 11 to 8.62 ppm in 12a (FIG. 10) due to the effect of the sulfonimide group adjacent to 3-H.

20S Proteasome Inhibition Assay

Six distinct catalytic active sites were thought to be responsible for the hydrolysis of polypeptide substrate by proteasome, among which chymotrypsin-like (CT-L), tropsin-like (T-L) and polyglutamine peptide hydrolysis (PGPH) activity were most firmly established and characterized. These proteolysis activities are substrate specific. For example, Suc-Leu-Leu-Val-Tyr-AMC has been used for chymotrypsin-like activity substrate, Bz-Val-Gly-Arg-AMC for trypsin-like susbtrate and benzyloxycarbonyl Z-Leu-Leu-Glu-AMC for PGPH activity susbtrate. In our work, we used chymotrypsin-like substrate Suc-Leu-Leu-Val-Tyr-AMC to test the proteasome inhibition activity of the synthesized compounds.

Figure 12:
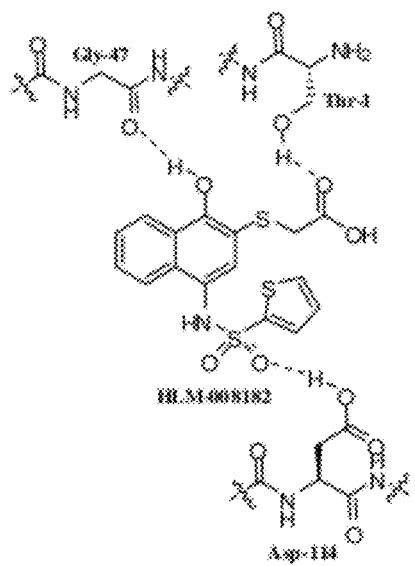
FIG. 12: H-bonding interaction between HLM-008182 and chymotrypsin-like catalytic site of 20S proteasome predicted by molecular modeling.

Structure and Activity Relationship by Modifications on 2-Substitution and 4-Sulfonamide Moiety Compound 10a is an in-house synthesis compound of HLM-008182. It exhibits comparable proteasome inhibition activity to the commercial sample HLM-008182 (FIG. 11, entry 1 and 6). This further confirmed HLM-008182 as a proteasome inhibitor. The interactions between HLM-008182 and chymotrysin-like catalytic site of 20S proteasome was predicted using molecular modeling and suggested that 2-side chain is H-bonding to the residue of Thr-1 through carboxylic acid acceptor (FIG. 12). Replacement of the side chain at the 2 position by small groups, such as hydrogen (compound 3) or halides (compound 4a~c), caused the loss of the inhibitory activity. The essentialness of the carboxylic acid moiety to the inhibitory activity was further confirmed by modification of the carboxylic group at the side chain. When the carboxylic acid moiety was replaced by the simple alkyl group (compound 14j) or the hydroxyl group (compound 14k), the inhibitory activity totally lost. The thio-ether side chain at the 2 position was essential to retain the inhibitory activity. For example, replacement of thio-ether side chain by ether or sulfone moiety diminished the inhibitory activity (compound 10d and 10f. Molecular modeling analysis indicated that 1-hydroxyl in the molecule of HLM-008182 played the role as a hydrogen bond donor to Gly47 in the 20S proteasome (FIG. 12). The inhibitory activity could be reduced or lost by formation of an intramolecular hydrogen bond between 1-hydroxyl and other groups in the inhibitor molecules. In compound 10d and 10f, ether and sulfone moiety at the 2 position could play roles as hydrogen bond acceptors from 1-hydroxyl, thus made the loss or reduction of the inhibitory activity.

The inhibitory potency of compounds with the ester chain was reduced compared to acid analogues (FIG. 11, entry 2, 4, 6 and 8: compound 9a vs 10a, 9c vs 10c). When the length of the 2-side chain was increased by one carbon, the inhibitory activity diminished (FIG. 11, entry 6 and 7: 10a vs 10b). In series of 2-amide chain inhibitors (compound 14f~h), increasing length of 2-side chain caused the partial or complete loss of the activity. As H-bonding to Thr-1 residue was essential for hydronaphthoquinone sulfonamide inhibitors to inhibit proteasome chymotrpsin-like activity, we also tested compounds with carboxylic acid mimics, such as tetrazole and triazole at the 2 position. The results showed that the compounds bearing these carboxylic acid mimics exhibited comparable inhibition potency against proteasome to the lead compound (FIG. 11, entry 9 and 10: compound 14d and 14e).

Linear side chains at the 2 position were more favorable for inhibition activity than branched side chains. When the linear chain of acetic acid at the 2 position of compound 14n and 14q was replaced by branched chain of isopropionic acid in compound 14u and 14v, the activity was decreased by ~2 fold (FIG. 11, entry 16, 17, 20 and 21). The similar results presented when the linear side chain was replaced by an aromatic ring (FIG. 11, entry 6 and 12: compound 10a vs 14l).

The modification of aromatic sulfonamide at the 4 position retained or slightly decreased the proteasome inhibition activity as compared to the lead compound 10a. For example, the inhibitory activity was tolerated by replacing the thiophene ring by phenyl ring (FIG. 11, entry 6 and 8: $IC_{50}$=1.47 μM for 10a vs 2.08 μM for 10c) or 4-biphenyl group (FIG. 11, entry 18: $IC_{50}$=1.90 μM for 14s). Substitution at the para position of 4-benzenesulfonamide by nitro group slightly enhanced the activity (FIG. 11, entry 4 and 5: compound 9c vs 9e). The decoration of the thiophene ring or phenyl with chlorine also helped to retain the inhibitory activity against proteasome (FIG. 11, entry 14~16: compound 14n~p). The bulky naphthalene ring slightly decreased the activity by 3 fold (FIG. 11, entry 17: compound 14q).

Compound 13w, the oxidized form of HLM-008182 showed comparable inhibitory potency. This indicated that the proteasome activity might be inhibited by hydronaphthoquinone sulfonamide derivatives through oxidation of the inhibitors. The mechanism of action is not clear yet.

EXAMPLES

All reagents were purchased from commercial suppliers and used without further purification. Melting points were determined using a Barnstead international melting point apparatus and remain uncorrected. 1H NMR spectra were recorded on a Varian Mercury 400 MHz spectrometer with $CDCl_3$, $CD_2Cl_2$ or $d^6$-DMSO as the solvents. All coupling constants are measured in hertz (Hz), and the chemical shifts (δH) are quoted in parts per million (ppm). High resolution mass spectroscopy was carried out on an Agilent 6210 LC/MS (ESI-TOF). Microwave reactions were performed in Biotage initiator 8 machines. Flash chromatograph was done on Flash Master II (Biotage) using a pre-packed silica gel column and gradient elution with Hexane/EtOAc system. Thin layer chromatography was performed using silica gel 60 254 plates (Fisher), with observation under UV when necessary. Anhydrous solvents (ethanol, dichloromethylene, 1,2-dichloroethane, 1,4-dioxane and tetrahydrofuran) were used as purchased from Aldrich. HPLC grade solvents (methanol, acetonitrile, and water) were purchased from Burdick and Jackson for mass analysis.

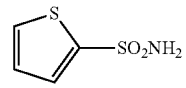

Thiophene-2-sulfonamide: 365.3 mg thiophene-2-sulfonyl chloride was dissolved in 5 ml THF, to which at 0° C. was added 1.7 ml $NH_3$ solution drop wise. The resulting mixture was stirred at r.t. for 2 hrs and acidified with conc. HCl at 0° C. to pH=~2. The organic solvent was removed via rotavap and the aqueous suspension was extracted with ethyl acetate. The extract was combined and washed with saturated $NaHCO_3$ solution, water and brine. Dried over $Na_2SO_4$, the organic phase was filtered and the filtrate was concentrated affording the title compound 212 mg (65%) as a white solid, m.p.: 137-139° C.

$^1$H-NMR, 400 MHz, $CDCl_3$, δ (ppm): 7.68 (dd, J=1.3 Hz, 3.8 Hz, 1H), 7.60 (dd, J=1.3 Hz, 5.0 Hz, 1H), 7.08 (dd, J=3.8 Hz, 5.0 Hz, 1H), 4.98 (br, 2H).

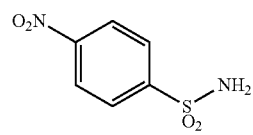

4-nitrobenzenesulfonamide was prepared according to the procedure for thiophene-2-sulfonamide YG1-030 except using 4-nitrobenzenesulfonyl chloride, which afforded the title compound 1.953 g (96.6%) as a pale yellow solid, m.p.: 178-180° C. $^1$H-NMR, 400 MHz, d$^6$-DMSO, δ (ppm): 8.40 (d, J=8.6 Hz, 2H), 8.04 (d, J=8.6 Hz, 2H), 7.72 (br, 2H). HRMS (ESI-ve) m/z calculated for $C_6H_6N_2O_4S$ (M−H)$^-$ 200.9976. Found 200.9986.

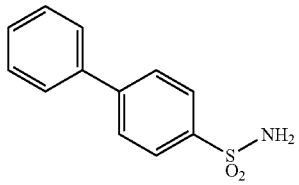 [SMILES: NS(=O)(=O)c1ccc(-c2ccccc2)cc1]

4-biphenylsulfonamide was prepared according to the procedure for thiophene-2-sulfonamide YG1-030 except using 4-biphenylsulfonyl chloride, which afforded the title compound 642.2 mg (90.6%) as a white solid, m.p.: 223-225° C.

$^1$H-NMR, 400 MHz, d$^6$-DMSO, δ (ppm): 7.88 (d, J=8.0 Hz, 2H), 7.84 (d, J=7.9 Hz, 2H), 7.71 (d, J=7.3 Hz, 2H), 7.49 (t, J=7.1 Hz, 2H), 7.41 (m, 3H).

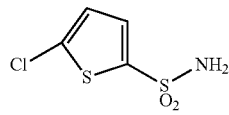

5-chlorothiophene-2-sulfonamide was prepared according to the procedure for thiophene-2-sulfonamide YG1-030 except using 4-biphenylsulfonyl chloride, which afforded the title compound 932.5 mg (94.4%) as a white solid, m.p.: 110-112° C.

$^1$H-NMR, 400 MHz, CDCl$_3$, δ (ppm): 7.44 (d, J=4.0 Hz, 1H), 7.06 (d, J=4.1 Hz, 1H), 6.01 (br, 2H).

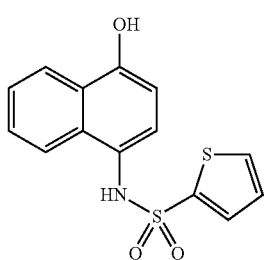

(3)

N-(4-hydroxynaphthalen-1-yl)thiophene-2-sulfonamide (3): 1.957 g 4-aminonaphth-1-ol hydrochloride salt was suspended in 80 ml dichloromethylene, to which at 0° C. was added 3.0 ml triethylamine. The suspension became a dark brown solution. To the solution was added 1.827 g thiophene-2-sulfonyl chloride. The mixture was stirred at r.t. overnight. The reaction mixture was diluted with dichloromethylene to 200 ml and washed with 1N HCl solution (30 ml×3), water (30 ml×3) and brine (30 ml). Dried over MgSO$_4$, the organic phase was filtered and the filtrate was concentrated to dryness. The crude product was suspended in 50% methanol/H2O and filtered. The solid was washed with 50% methanol/H$_2$O affording 2.7 g (90%) brown solid, m.p.: 146-148° C.

$^1$H-NMR, 400 MHz, CD$_2$Cl$_2$, δ (ppm): 7.81 (m, 2H), 7.70 (dd, J=1.4 Hz, 5.0 Hz, 1H), 7.60 (dd, J=1.3 Hz, 3.8 Hz, 1H), 7.46 (m, 2H), 7.07 (d, J=8.2 Hz, 1H), 7.06 (dd, J=3.8 Hz, 5.0 Hz, 1H), 6.66 (d, J=8.2 Hz, 1H), 4.30 (br, 2H).

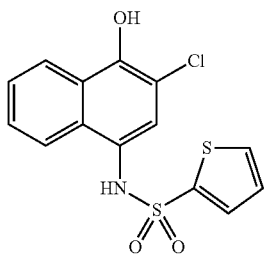

(4a)

N-(3-chloro-4-hydroxynaphthalen-1-yl)thiophene-2-sulfonamide (4a): 0.987 g N-(4-hydroxynaphthalen-1-yl)thiophene-2-sulfonamide (3) was suspended in 10 ml methanol, to which was added 3 ml hydrogen peroxide solution (35%). The mixture was stirred at r.t. for 2 h. Additional 3 ml hydrogen peroxide solution was added followed by 1 ml HCl solution (4 M in dioxane). The reaction was continued for another 2 h. The organic solvent was removed via rotavap and the residue was redissolved in ethyl acetate (100 ml). Washed with water (20 ml×3) and brine (20 ml×2), the organic phase was dried over Mg$_2$SO$_4$. The organic phase was filtered and concentrated. The crude product was separated via flash chromatography (Hex/EtOAc) affording 244 mg (22.2%) brown solid, m.p.: 113-115° C.

$^1$H-NMR, 400 MHz, CDCl$_3$, δ (ppm): 7.79 (d, J=8.4 Hz, 1H), 7.70 (d, J=8.1 Hz, 1H), 7.64 (dd, J=1.1 Hz, 4.9 Hz, 1H), 7.60 (dd, J=1.2 Hz, 3.8 Hz, 1H), 7.40 (m, 2H), 7.19 (s, 1H), 7.02 (dd, J=4.0 Hz, 4.8 Hz, 1H), 4.46 (br, 2H).

HRMS (ESI+ve) m/z calculated for $C_{14}H_{10}ClO_3S_2$ (M+H)$^+$ 339.9863. Found 339.9856.

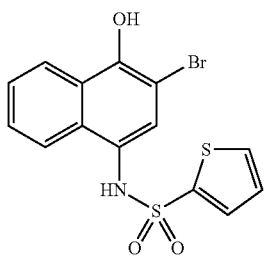

(4b)

N-(3-bromo-4-hydroxynaphthalen-1-yl)thiophene-2-sulfonamide (4b): 305.7 mg N-(4-hydroxynaphthalen-1-yl)thiophene-2-sulfonamide (3) was dissolved in 1 ml DMF, to which at 0° C. was added 320 mg Br$_2$ in 1 ml dichloromethylene solution. After stirred at r.t. for 1 h, 558 μl TEA was added at 0° C. The reaction was stirred at r.t. overnight and diluted with ethyl acetate to 50 ml. The organic phase was washed with water and brine. Dried over Na2SO4, the organic phase was filtered and concentrated. The crude product was purified via flash chromatography (Hex/EtOAc gradient) affording an orange-red solid 140 mg (36.4%), m.p.: 128-130° C.

$^1$H-NMR, 400 MHz, CDCl$_3$, δ (ppm): 7.81 (m, 1H), 7.75 (m, 1H), 7.66 (dd, J=1.3 Hz, 5.0 Hz, 1H), 7.61 (dd, J=1.3 Hz, 3.8 Hz, 1H), 7.43 (m, 2H), 7.32 (s, 1H), 7.04 (dd, J=3.9 Hz, 5.0 Hz, 1H), 4.75 (br, 2H).

HRMS (ESI+ve) m/z calculated for $C_{14}H_{10}BrO_3S_2$ (M+H)$^+$ 383.9358. Found 383.9347.

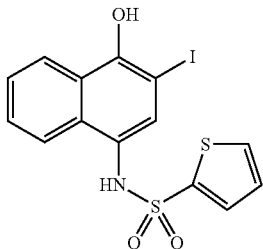
(4c)

N-(3-iodo-4-hydroxynaphthalen-1-yl)thiophene-2-sulfonamide (4c): was prepared according to the procedure for 4b except using $I_2$ solid. The reaction afforded title compound 129.4 mg (100%) as a brown solid, m.p.: 134-136° C.

$^1$H-NMR, 400 MHz, CDCl$_3$, δ (ppm): 7.82 (d, J=8.0 Hz, 1H), 7.74 (d, J=7.8 Hz, 1H), 7.68 (d, J=5.0 Hz, 1H), 7.62 (d, J=3.8 Hz, 1H), 7.45 (m, 3H), 7.06 (dd, J=3.8 Hz, 5.0 Hz, 1H).

HRMS (ESI+ve) m/z calculated for $C_{14}H_{10}IO_3S_2$ (M+H)$^+$ 431.9220. Found 431.9216.

Procedure A for 10a:

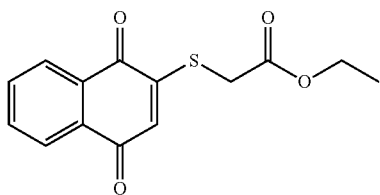
(7a)

Ethyl 2-(1,4-dioxo-1,4-dihydronaphthalen-2-ylthio)acetate (7a): 790.8 mg 1,4-naphthoquinone was added portion wise to 10 ml ethanol containing 0.5 eq. ethyl mercaptoacetate at room temperature. The mixture was stirred at room temperature for 30 min. The yellow solid was filtered, washed with ethanol and dried over vacuum affording title compound 491 mg (88.9%) as a yellow solid, m.p.: 150-152° C.

$^1$H-NMR, 400 MHz, CDCl$_3$, δ (ppm): 8.12 (d, J=7.4 Hz, 1H), 8.09 (d, J=7.4 Hz, 1H), 7.77 (t, J=7.5 Hz, 1H), 7.72 (t, J=7.5 HZ, 1H), 6.70 (s, 1H), 4.26 (q, J=7.1 Hz, 2H), 3.67 (s, 2H), 1.31 (t, J=7.1 HZ, 3H).

HRMS (ESI+ve) m/z calculated for $C_{14}H_{12}O_4S$ (M+H)$^+$ 277.0529. Found 277.0529.

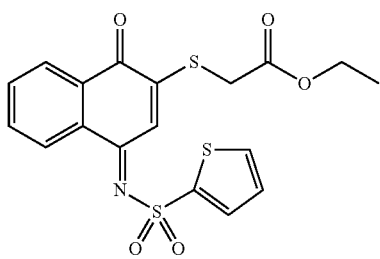
(8a)

Ethyl 2-(1-oxo-4-(thiophen-2-ylsulfonylimino)-1,4-dihydronaphthalen-2-ylthio)acetate (8a): 63 mg (0.228 mmoles) ethyl 2-(1,4-dioxo-1,4-dihydronaphthalen-2-ylthio)acetate (7a) was mixed with 37 mg (0.228 mmoles) thiophene-2-sulfonamide in 2.5 ml dichloromethylene, to which at 0° C. was added 76 mg TiCl$_4$.2THF followed by 70 μl triethylamine. The mixture was heated at 60° C. with microwave synthesizer (Initiator 8, Biotage) for 20 min. Diluted with dichloromethylene to 60 ml, the reaction mixture was washed with H$_2$O and brine and dried over Na$_2$SO$_4$. After removal of Na$_2$SO$_4$, the filtrate was concentrated and the residue was purified with flash column (EtOAc/Hexane) affording title compound 58 mg (60.4%) as orange oil which was solidified on standing, m.p.: 110-112° C.

$^1$H-NMR, 400 MHz, CDCl$_3$, δ (ppm): 8.22 (dd, J=3.3 Hz, 5.9 Hz, 1H), 8.15 (dd, J=3.5 Hz, 5.7 HZ, 1H), 7.96 (s, 1H), 7.83 (dd, J=1.3 Hz, 3.8 Hz), 7.70 (m, 3H), 7.15 (dd, J=3.8 Hz, 5.0 Hz, 1H), 4.32 (q, J=7.1 Hz, 2H), 3.80 (s, 2H), 1.35 (t, J=7.1 Hz, 3H).

HRMS (ESI+ve) m/z calculated for $C_{18}H_{15}NO_5S_3$ (M+H)$^+$ 422.0185. Found 422.0193.

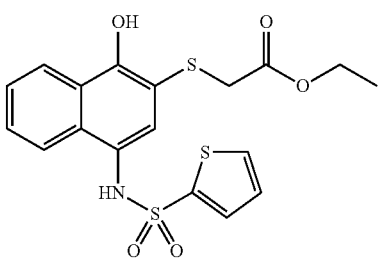
(9a)

Ethyl 2-(1-hydroxy-4-(thiophene-2-sulfonamido)naphthalen-2-ylthio)acetate (9a): 52 mg (E)-ethyl 2-(1-oxo-4-(thiophen-2-ylsulfonylimino)-1,4-dihydronaphthalen-2-ylthio)acetate (8a) was dissolved in 2 ml THF, to which was added 2 ml aqueous solution containing 107 mg Na$_2$S$_2$O$_4$. The resulting biphasic solution was stirred at r.t. for 1 h until it turned pale yellow. The mixture was diluted with ethyl acetate and washed with water and brine. Dried over Na$_2$SO$_4$, the organic solution was filtered and the filtrate was concentrated. The crude product was purified via flash column (EtOAc/Hexane) yielding 25.2 mg (58.7%) title compound, m.p.: 116-118° C.

$^1$H-NMR, 400 MHz, CDCl$_3$, δ (ppm): 8.42 (s, 1H), 8.29 (dd, J=3.2 Hz, 6.3 Hz, 1H), 7.80 (dd, J=3.1 Hz, 6.3 Hz, 1H), 7.52 (d, J=4.0 Hz, 1H), 7.48 (dd, J=3.2 Hz, 6.4 Hz, 2H), 7.38 (d, J=2.7 Hz, 1H), 7.35 (s, 1H), 6.95 (t, J=4.6 Hz, 1H), 6.77 (s, 1H), 4.18 (q, J=7.1 Hz, 2H), 3.48 (s, 2H), 1.21 (t, J=7.1 Hz, 3H).

HRMS (ESI+ve) m/z calculated for $C_{18}H_{17}NO_5S_3$ (M+H)$^+$ 424.0342. Found 424.0335.

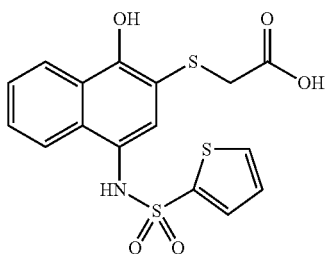
(10a)

2-(1-hydroxy-4-(thiophene-2-sulfonamido)naphthalen-2-ylthio)acetic acid (10a): 8 mg Ethyl 2-(1-hydroxy-4-

(thiophene-2-sulfonamido)naphthalen-2-ylthio)acetate (9a) was dissolved in 0.5 ml dioxane, to which was added 0.5 ml HCl solution (4 N). The reaction mixture was heated at 100° C. with M.W. for 10 min and diluted to 20 ml with ethyl acetate. Washed with water and brine, the organic solution was dried over Na₂SO₄ and filtered. The filtrate was concentrated to dryness affording title compound 6 mg (80%) as a pale yellow solid, m.p.: 175-177° C.

¹H-NMR, 400 MHz, d⁶-DMSO, δ (ppm): 10.08 (s, 1H), 8.13 (d, J=8.5 Hz, 1H), 7.85 (s, 1H), 7.84 (d, J=3.6 Hz, 2H), 7.44 (m, 2H), 7.34 (d, J=3.2 Hz, 1H), 7.06 (s, 1H), 7.05 (t, J=4.1 Hz, 1H), 3.52 (s, 2H).

HRMS (ESI−ve) m/z calculated for $C_{16}H_{13}NO_5S_3$ (M−H)⁻ 393.9883. Found 393.9885.

Oxidation of 10a: around 1 mg 10a was suspended in 0.6 ml CDCl₃ in a NMR tube. The suspension was sonicated with a supersound power of 308 W (50/60 Hz) until a clear bright yellow solution was afforded.

¹H-NMR, 400 MHz, CDCl₃, δ (ppm): 8.22 (m, 1H), 8.15 (m, 1H), 7.99 (s, 1H), 7.83 (dd, J=1.3 Hz, 3.8 Hz, 1H), 7.71 (m, 3H), 7.15 (dd, J=3.8 Hz, 5.0 Hz, 1H), 3.86 (s, 2H).

Procedure B for 10a:

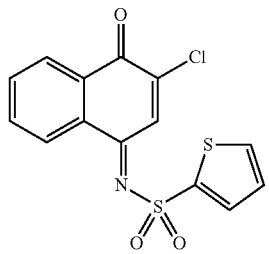

(12a)

N-(3-chloro-4-oxonaphthalen-1(4H)-ylidene)thiophene-2-sulfonamide (12a): 385.2 mg 2-chloro-1,4-naphthoquinone (11) was mixed with 326.4 mg thiophene-2-sulfonamide in 15 ml dichloromethylene, to which at 0° C. was added 2 ml TiCl₄ dichloromethylene solution followed by 613.3 μl. The mixture was heated at 60° C. with M.W. for 15 min and the black mixture was poured into 100 ml ethyl acetate. The insoluble was removed by filtrate through a pad of celite. The filtrate was concentrated and the residue was suspended in dichloromethylene. The brown insoluble stuff was removed by filtration and the filtrate was again concentrated to dryness. The residue was suspended in ethyl acteate/hexane (1:1) and the yellow solid was filtered. The solid was washed with ethyl acteate/hexane (1:1) and dried over vacuum affording title compound 377.7 mg (55.9%) as a yellow solid. When TiCl₄·2THF and THF were used instead, the reaction afforded the title compound 522 mg (77.3%) as a yellow solid, m.p.: 167-169° C.

¹H-NMR, 400 MHz, CDCl₃, δ (ppm): 8.62 (s, 1H), 8.23 (tt, J=1.5 Hz, 9.2 Hz, 2H), 7.86 (dd, J=1.4 Hz, 3.8 Hz, 1H), 7.75 (m, 3H), 7.18 (dd, J=3.8 Hz, 5.0 Hz, 1H).

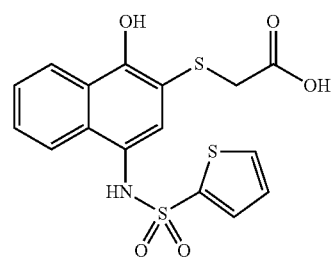

(10a)

2-(1-hydroxy-4-(thiophene-2-sulfonamido)naphthalen-2-ylthio)acetic acid (10a): 33.8 mg (E)-N-(3-chloro-4-oxonaphthalen-1(4H)-ylidene)thiophene-2-sulfonamide (12a) was dissolved in 2 ml THF, to which was added 0.1 ml THF solution containing 0.1 mmole thioglycolic acid followed by 1 eq. pyridine. The mixture was stirred at r.t. for 10 min and the solvent was removed via rotavap. The orange-red residue was redissolved in 50 ml ethyl acetate and 0.5 M NaHSO₄ solution and transferred to a separation funnel. The organic layer was separated and washed with 0.5 M NaHSO₄ solution. To the ethyl acetate solution, was added 5 eq. sodium hydrosulfite solid, followed by 10 ml water. The mixture was shaken until the organic phase turned colorless. The organic phase was separated and washed with water and brine. Dried over Na₂SO₄, the organic phase was filtered and the filtrate was concentrated to dryness. The residual solid was suspended in dichloromethylene/hexane (1:1) and filtered. The solid was washed with dichloromethylene affording title compound 25 mg (63.6%) as an off-white solid.

¹H-NMR, 400 MHz, d⁶-DMSO, δ (ppm): 12.65 (br, 1H), 10.07 (s, 1H), 8.13 (d, J=8.0 Hz, 1H), 7.85 (s, 1H), 7.84 (d, J=3.6 Hz, 1H), 7.44 (m, 2H), 7.34 (d, J=3.7 Hz, 1H), 7.06 (s, 1H), 7.04 (t, J=3.8 Hz, 1H), 3.52 (s, 2H).

HRMS (ESI−ve) m/z calculated for $C_{16}H_{13}NO_5S_3$ (M−H)⁻ 393.9883. Found 393.9889.

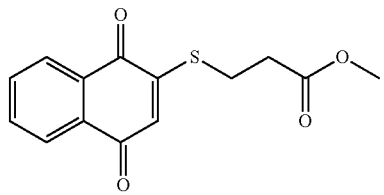

(7b)

Methyl 3-(1,4-dioxo-1,4-dihydronaphthalen-2-ylthio)propanoate (7b) was prepared according to the procedure for (7a) except using methyl 3-mercaptopropionate. The reaction afforded title compound 1.298 g (93.9%) as a yellow solid, m.p.: 108-110° C.

¹H-NMR, 400 MHz, CDCl₃, δ (ppm): 8.10 (t, J=7.6 Hz, 2H), 7.76 (t, J=7.5 Hz, 1H), 7.71 (t, J=7.4 Hz, 1H), 6.64 (s, 1H), 3.74 (s, 3H), 3.13 (t, J=7.4 Hz, 2H), 2.78 (t, J=7.3 Hz, 2H).

HRMS (ESI+ve) m/z calculated for $C_{14}H_{12}O_4S$ (M+H)⁺ 277.0529. Found 277.0539.

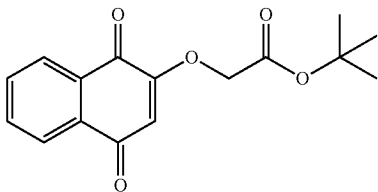

tert-Butyl 2-(1,4-dioxo-1,4-dihydronaphthalen-2-yloxy) acetate (7c): a mixture of 2-hydroxynaphthalene-1,4-dione (6, 0.52 g, 3.0 mmol), tert-butyl 2-bromoacetate (0.78 g, 4.0 mmol), silver oxide (0.93 g, 4.0 mmol) and potassium iodide (0.05 g, 0.3 mmol) were refluxed in 10 ml of chloroform overnight under Ar. The reaction mixture was filtered and washed with DCM (3×20 ml), the filtrate was concentrated and purified with flash chromatography to give compound 7c as a light yellow solid, 13%, m.p.=120-122° C.

$^1$H NMR, 400 MHz, CDCl$_3$, δ (ppm): 8.15 (d, J=7.2 Hz, 1H), 8.08 (d, J=7.2 Hz, 1H), 7.78-7.73 (m, 2H), 6.04 (s, 1H), 4.62 (s, 2H), 1.41 (s, 9H).

HRMS (ESI+ve) m/z calculated for C$_{16}$H$_{17}$O$_5$ (M+H)$^+$ 289.1071. Found 289.1090.

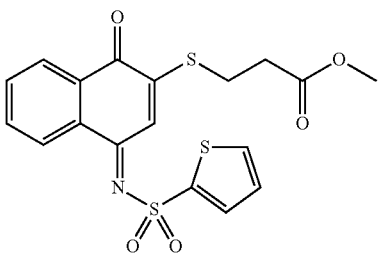

5.2.17 Methyl 3-(1-oxo-4-(thiophen-2-ylsulfonylimino)-1,4-dihydronaphthalen-2-ylthio) propanoate (8b) was prepared according to the procedure for 8a except using 7b, which afforded 74 mg (35.1%) title compound as an orange solid, m.p.: 140-142° C.

$^1$H-NMR, 400 MHz, CDCl$_3$, δ (ppm): 8.22 (m, 1H), 8.12 (m, 1H), 7.90 (s, 1H), 7.82 (dd, J=1.3 Hz, 3.8 Hz, 1H), 7.69 (m, 3H), 7.15 (dd, J=5.0 Hz, 8.8 Hz, 1H), 3.75 (s, 3H), 3.26 (t, J=6.9 Hz, 2H), 2.85 (t, J=6.9 Hz, 2H).

HRMS (ESI+ve) m/z calculated for C$_{18}$H$_{15}$NO$_5$S$_3$ (M+H)$^+$ 422.0185. Found 422.0185.

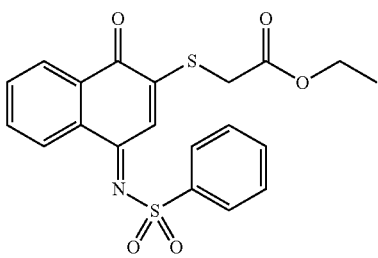 [SMILES: CCOC(=O)CSC1=C/C(=N\S(=O)(=O)c2ccccc2)c2ccccc2C1=O]

Ethyl 2-(1-oxo-4-(phenylsulfonylimino)-1,4-dihydronaphthalen-2-ylthio)acetate (8c) was prepared according to the procedure for 8a except using benzenesulfonamide, which afforded 131.8 mg (31.7%) title compound as a yellow solid, m.p.: 93-95° C.

$^1$H-NMR, 400 MHz, CDCl$_3$, δ (ppm): 8.11 (dd, J=2.1 Hz, 6.6 Hz, 2H), 8.07 (d, J=7.3 Hz, 2H), 7.99 (s, 1H), 7.64 (m, 3H), 7.85 (t, J=8.0 Hz, 2H), 4.32 (q, J=7.1 Hz, 2H), 3.81 (s, 2H), 1.34 (t, J=7.1 Hz, 3H).

HRMS (ESI+ve) m/z calculated for C$_{20}$H$_{17}$NO$_5$S$_2$ (M+H)$^+$ 416.0621. Found 416.0621.

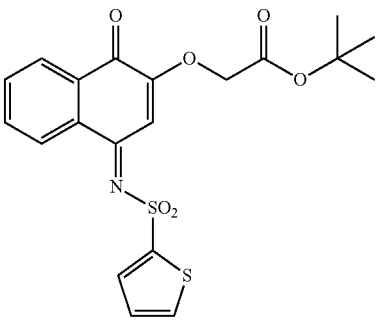

tert-Butyl-2-(1-oxo-4-(thiophen-2-ylsulfonylimino)-1,4-dihydronaphthalen-2-yloxy)acetate (8d): triethyl amine (0.12 ml, 0.88 mmol) was added in the mixture of tert-Butyl 2-(1,4-dioxo-1,4-dihydronaphthalen-2-yloxy)acetate (7c, 0.115 g, 0.4 mmol) and thiophene-2-sulfonamide (0.078 g, 0.48 mmol) in anhydrous DCM (4 ml), followed by adding TiCl$_4$.2THF. The reaction mixture was heated with μW at 60° C. for 20 min. and poured into EtOAC, then filtered with celite. The filtrate was concentrated under reduce pressure and purified by flash chromatography to give compound 8d as a yellow solid, 22%, m.p.=153-155° C.

$^1$H NMR, 400 MHz, CDCl$_3$, δ (ppm): 8.07 (d, J=9.0 Hz, 1H), 8.01 (d, J=9.0 Hz, 1H), 7.64 (d, J=3.7 Hz, 1H), 7.55-7.53 (m, 3H), 7.10 (s, 1H), 6.98 (t, J=3.8 Hz, 1H), 4.58 (s, 2H), 1.39 (s, 9H);).

HRMS (ESI+ve) m/z calculated for C$_{16}$H$_{17}$O$_5$ (M+H-tBu-CO$_2$)$^+$ 334.0208. Found 334.0222.

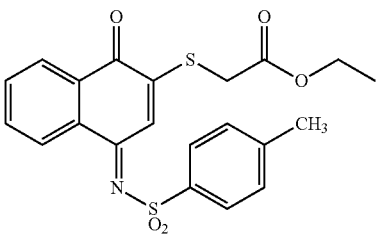

Ethyl 2-(1-oxo-4-(tosylimino)-1,4-dihydronaphthalen-2-ylthio)acetate (8f) was prepared according to the procedure for 8a except using 4-methylbenzenesulfonamide, TiCl$_4$.2THF and THF as solvent. The title compound 100.7 mg (46.9%) was obtained according to the workup procedure for 12a as a yellow solid, m.p.: ° C.

$^1$H-NMR, 400 MHz, CDCl$_3$, δ (ppm): 8.14 (dd, J=1.4 Hz, 7.2 Hz, 2H), 8.03 (s, 1H), 7.95 (d, J=8.2 Hz, 2H), 7.65 (m, 2H), 7.38 (d, J=8.5 Hz, 2H), 4.32 (q, J=7.1 Hz, 2H), 3.81 (s, 2H), 2.47 (s, 3H), 1.35 (t, J=7.1 Hz, 3H).

HRMS (ESI+ve) m/z calculated for C$_{21}$H$_{19}$NO$_5$S$_2$ (M+H)$^+$ 430.0777, found 430.0776.

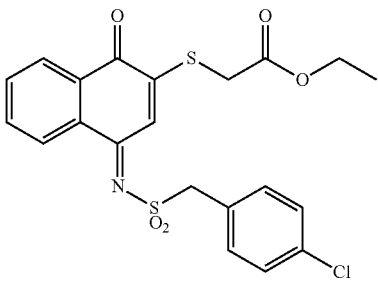

(8g)

Ethyl 2-(4-(4-chlorobenzylsulfonylimino)-1-oxo-1,4-dihydronaphthalen-2-ylthio)-acetate (8g) was prepared according to the procedure for 8a except using (4-chlorophenyl)methanesulfonamide, TiCl$_4$·2THF and THF as solvent. The title compound 130 mg (56%) was obtained according to the workup procedure for 12a as a yellow solid, m.p.: ° C.

$^1$H-NMR, 400 MHz, CDCl$_3$, δ (ppm): 8.14 (m, 2H), 7.72 (m, 2H), 7.70 (s, 1H), 7.47 (d, J=8.4 Hz, 2H), 7.38 (d, J=8.4 Hz, 2H), 4.55 (s, 2H), 4.26 (q, J=7.1 Hz, 2H), 3.70 (s, 2H), 1.30 (t, J=7.1 Hz, 3H).

HRMS (ESI+ve) m/z calculated for C$_{21}$H$_{18}$ClNO$_5$S$_2$ (M+H)$^+$ 464.0388, found 464.0388.

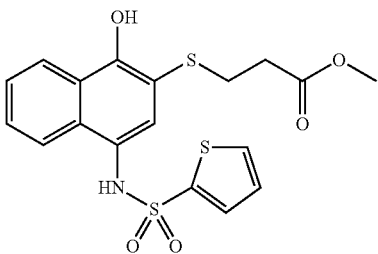

(9b)

Methyl 3-(1-hydroxy-4-(thiophene-2-sulfonamido)naphthalen-2-ylthio)propanoate (9b) was prepared according to the procedure for 9a except using 8b affording 28 mg (93%) title compound as a pale yellow solid without column purification, m.p.: 117-119° C.

$^1$H-NMR, 400 MHz, CDCl$_3$, δ (ppm): 8.25 (dd, J=3.2 Hz, 6.4 Hz, 1H), 7.87 (dd, J=3.2 Hz, 6.3 Hz, 1H), 7.60 (br, 1H), 7.50 (m, 3H), 7.41 (dd, J=1.3 Hz, 3.7 Hz, 1H), 7.32 (s, 1H), 6.95 (dd, J=3.8 Hz, 5.0 Hz, 1H), 6.91 (br, 1H), 3.70 (s, 3H), 2.93 (t, J=7.1 Hz, 2H), 2.51 (t, J=7.0 Hz, 2H).

HRMS (ESI+ve) m/z calculated for C$_{18}$H$_{17}$NO$_5$S$_3$ (M+Na)$^+$ 446.0161, found 446.0157.

(9c)

Ethyl 2-(1-hydroxy-4-(phenylsulfonamido)naphthalen-2-ylthio)acetate (9c) was prepared according to the procedure for 9a affording 68 mg (81.5%) title compound as a pale yellow solid, m.p.: 118-120° C.

$^1$H-NMR, 400 MHz, CD$_2$Cl$_2$, δ (ppm): 8.52 (s, 1H), 8.27 (m, 1H), 7.84 (m, 1H), 7.68 (d, J=8.4 Hz, 2H), 7.57 (t, J=7.5 Hz, 1H), 7.50 (m, 2H), 7.43 (t, J=7.9 Hz, 2H), 7.17 (s, 1H), 6.59 (br, 1H), 4.17 (q, J=7.1 Hz, 2H), 3.44 (s, 2H), 1.21 (t, J=7.2 Hz, 3H).

HRMS (ESI+ve) m/z calculated for C$_{20}$N$_{19}$NO$_5$S$_2$ (M+Na)$^+$ 440.0597, found 440.0596.

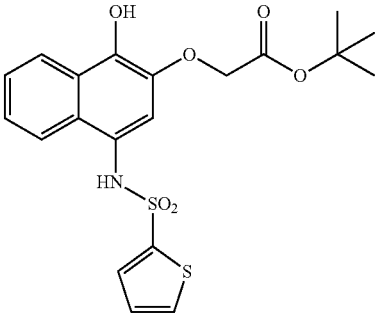

(9d)

tert-Butyl-2-(1-hydroxy-4-(thiophene-2-sulfonamido)naphthalen-2-yloxy)acetate (9d): tert-Butyl-2-(1-oxo-4-(thiophen-2-ylsulfonylimino)-1,4-dihydronaphthalen-2-yloxy)acetate (8d, 0.07 g, 0.16 mmol) was dissolved in 3 ml of THF and stirred at r.t., Na$_2$SO$_4$ (0.139 g, 0.8 mmol) was added with vigorously stirring. 1 ml of H$_2$O was added to mixture until Na$_2$SO$_4$ was dissolved completely. The reaction mixture was stirred at r.t. for 10 min. The color changed from orange to light yellow. 40 ml of EtOAc was added into the mixture and washed with 40 ml of water, followed by washing with brine, dried with MgSO$_4$ and filtered. The filtrate was concentrated under reduced pressure. The product was obtained by crystallization with EtOAc and hexane as a light yellow solid, 71%, m.p.=155-157° C.

$^1$H NMR, 400 MHz, CDCl$_3$, δ (ppm): 8.55 (broad s, 1H, disappear on D$_2$O shake), 8.25 (d, J=8.0 Hz, 1H), 7.55 (d, J=8.0 Hz, 1H), 7.45 (d, J=4.8 Hz, 1H), 7.45-7.29 (m, 3H), 7.24 (s, 1H), 6.90 (1H, J=4.8 Hz, 1H), 6.71 (s, 1H, disappear on D$_2$O shake), 4.54 (s, 2H), 1.51 (s, 9H).

HRMS (ESI–ve) m/z calculated for C$_{20}$H$_{20}$NO$_6$S$_2$ (M–H)$^-$ 434.0738, found 434.0755.

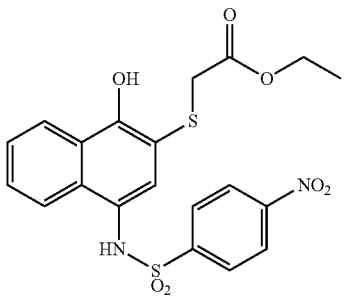 [SMILES: CCOC(=O)CSc1cc(NS(=O)(=O)c2ccc([N+](=O)[O-])cc2)c2ccccc2c1O]

(9e)

Ethyl 2-(1-hydroxy-4-(4-nitrophenylsulfonamido)naphthalen-2-ylthio)acetate (9e) was prepared according to the procedure for 8a except using 4-nitrobenzenesulfonamide, 1,2-dichloroethane as solvent and applying 100° C. to the reaction. The reaction was worked up according to the procedure for 12a and the title compound was isolated from the product mixture by flash chromatography (EtOAc/Hex) affording 48 mg (10.4%) as a brown solid, m.p.: 143-145° C.

¹H-NMR, 400 MHz, CD₃CN, δ (ppm): 8.49 (s, 1H), 8.25 (d, J=8.9 Hz, 2H), 8.24 (m, 1H), 8.01 (br, 1H), 7.89 (m, 1H), 7.87 (d, J=8.7 Hz, 2H), 7.54 (m, 2H), 7.13 (s, 1H), 4.11 (q, J=7.1 Hz, 2H), 3.47 (s, 2H), 1.16 (t, J=7.1 Hz, 3H).

HRMS (ESI+ve) m/z calculated for C₂₀H₁₈N₂O₇S₂ (M+Na)⁺ 485.0448, found 485.0438.

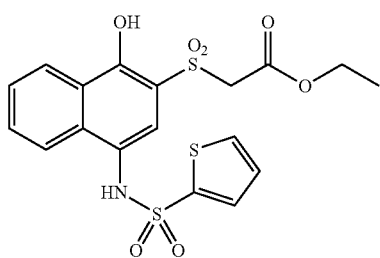

(9f)

Ethyl 2-(1-hydroxy-4-(thiophene-2-sulfonamido)naphthalen-2-ylsulfonyl)acetate (9f): 42.4 mg Ethyl 2-(1-hydroxy-4-(thiophene-2-sulfonamido)naphthalen-2-ylthio)acetate (9a) was dissolved in 2 ml acetone, to which was added 2 ml aqueous solution containing 307.4 mg oxone. The resulting mixture was stirred at r.t. overnight. The organic solvent was removed by rotavap and the residue extracted with ethyl acetate. The organic extract was combined and washed with water and brine. Dried over Na₂SO₄, the organic phase was filtered and the filtrate was concentrated to dryness affording 47 mg (100%) title compound as a pale yellow solid, m.p.: 154-156° C.

¹H-NMR, 400 MHz, CDCl₃, δ (ppm): 10.02 (s, 1H), 8.43 (d, J=8.4 Hz, 1H), 7.98 (d, J=8.4 Hz, 1H), 7.70 (t, J=8.0 Hz, 1H), 7.62 (t, J=7.9 Hz, 1H), 7.57 (d, J=5.0 Hz, 1H), 7.43 (d, J=3.7 Hz, 1H), 7.29 (s, 1H), 7.00 (dd, J=3.8 Hz, 4.9 Hz, 1H), 6.58 (s, 1H), 4.16 (q, J=7.2 Hz, 2H), 4.12 (s, 2H), 1.15 (t, J=7.2 Hz, 3H).

HRMS (ESI-ve) m/z calculated for C₁₈H₁₇NO₇S₃ (M-H)⁻ 454.0094, found 454.0112.

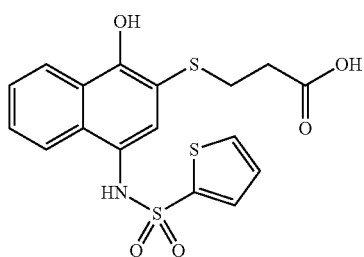

(10b)

3-(1-hydroxy-4-(thiophene-2-sulfonamido)naphthalen-2-ylthio)propanoic acid (10b) was prepared according to the procedure of procedure A for 10a except applying r.t. to the reaction overnight, which afforded 5.6 mg (13.5%) title compound as a white solid, m.p.: 185° C. (dec.).

¹H-NMR, 400 MHz, d⁶-DMSO, δ (ppm): 12.35 (s, 1H), 10.07 (s, 1H), 9.70 (s, 1H), 8.13 (d, J=7.6 Hz, 1H), 7.91 (d, J=7.8 Hz, 1H), 7.85 (d, J=5.0 Hz, 1H), 7.46 (m, 2H), 7.36 (d, J=3.7 Hz, 1H), 7.07 (t, J=4.9 Hz, 1H), 6.96 (s, 1H), 2.84 (t, J=7.2 Hz, 2H), 2.37 (t, J=7.1 Hz, 2H).

HRMS (ESI-ve) m/z calculated for C₁₇H₁₅NO₅S₃ (M-H)⁻ 408.0040, found 408.0054.

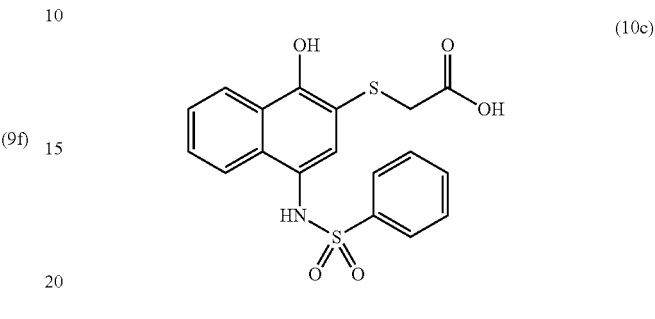

(10c)

2-(1-hydroxy-4-(phenylsulfonamido)naphthalen-2-ylthio)acetic acid (10c) was prepared according to the procedure of procedure A for 10a except applying r.t. to the reaction overnight, which afforded 20 mg (53.6%) title compound as an off-white solid, m.p.: 100-102° C.

¹H-NMR, 400 MHz, d⁶-DMSO, δ (ppm): 12.75 (br, 1H), 9.91 (s, 1H), 9.80 (br, 1H), 8.10 (d, J=8.1 Hz, 1H), 7.83 (d, J=8.3 Hz, 1H), 7.60 (d, J=7.7 Hz, 2H), 7.56 (t, J=7.3 Hz, 1H), 7.46 (t, J=7.6 Hz, 2H), 7.39 (m, 2H), 6.96 (s, 1H), 3.47 (s, 2H).

HRMS (ESI-ve) m/z calculated for C₁₈H₁₅NO₅S₂ (M-H)⁻ 388.0319, found 388.0330.

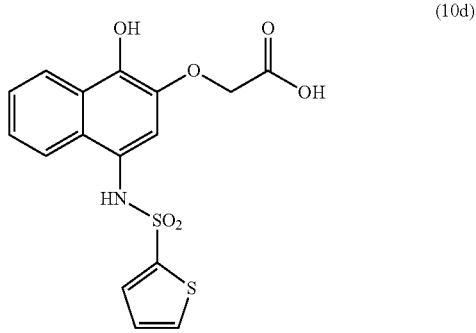

(10d)

2-(1-hydroxy-4-(thiophene-2-sulfonamido)naphthalen-2-yloxy)acetic acid (10d): tert-Butyl-2-(1-hydroxy-4-(thiophene-2-sulfonamido)naphthalen-2-yloxy)acetate (9d, 0.025 g, 0.057 mmol) was dissolved in 4 ml of 1:1 ratio of dioxane and concentrated hydrochloric acid and stirred at r.t. for 3 h. The mixture solution changed from clear to white cloudy. The solvent was evaporated under reduced pressure. The solid was washed with DCM and hexane separately to get pure product as a gray solid, 97%, m.p.=155-157° C.

¹H NMR, 400 MHz, DMSO-d₆, δ (ppm): 10.08 (s, 1H, disappear on D₂O shake), 8.03 (d, J=8.4 Hz, 1H), 7.81 (d, J=4.8 Hz, 1H), 7.77 (d, J=8.4 Hz, 1H), 7.38 (t, J=7.6 Hz, 1H), 7.33 (d, J=2.4 Hz, 1H), 7.27 (t, J=7.6 Hz, 1H), 7.04 (t, J=4.0 Hz, 1H), 6.86 (s, 1H), 4.55 (s, 2H).

HRMS (ESI-ve) m/z calculated for C₁₆H₁₂NO₆S₂ (M-H)⁻ 378.0112, found 378.011.

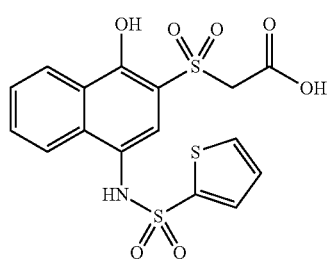

(10f)

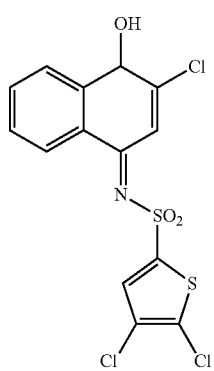

(12c)

2-(1-hydroxy-4-(thiophene-2-sulfonamido)naphthalen-2-ylsulfonyl)acetic acid (10f): 20 mg Ethyl 2-(1-hydroxy-4-(thiophene-2-sulfonamido)naphthalen-2-ylsulfonyl)-acetate (9f) was dissolved in 2 ml dioxane, to which was added 2 ml conc. HCl. The mixture was stirred at r.t. for 36 h. The solvent was removed by rotavap. The solid residue was washed with dichloromethylene affording title compound 18.3 mg (97.3%) as an off-white solid, m.p.: 210-212° C.

$^1$H-NMR, 400 MHz, d$^6$-DMSO, δ (ppm): 10.24 (s, 1H), 8.37 (d, J=8.7 Hz, 1H), 7.97 (d, J=7.8 Hz, 1H), 7.86 (d, J=4.3 Hz, 1H), 7.62 (m, 2H), 7.35 (s, 1H), 7.33 (d, J=3.0 Hz, 1H), 7.05 (dd, J=3.9 Hz, 4.9 Hz, 1H), 4.52 (s, 1H).

HRMS (ESI–ve) m/z calculated for $C_{16}H_{13}NO_7S_3$ (M–H)$^-$ 425.9781, found 425.9788.

4,5-dichloro-N-(3-chloro-4-oxonaphthalen-1(4H)-ylidene)thiophene-2-sulfonamide (12c) was prepared according to the procedure for 12a except using 4,5-dichlorobenzenesulfonamide, which afforded the title compound 260 mg (35%) as a yellow solid, m.p.: ° C.

$^1$H NMR (400 MHz, CDCl$_3$), δ (ppm): 8.49 (s, 1H), 8.22 (dt, J=6.0, 1.6 Hz, 2H), 7.82-7.74 (m, 2H), 7.64 (s, 1H).

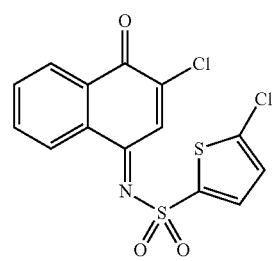

(12d)

5-chloro-N-(3-chloro-4-oxonaphthalen-1(4H)-ylidene)thiophene-2-sulfonamide (12d) was prepared according to the procedure for 12a except using 5-chlorothiophene-2-sulfonamide, which afforded the title compound 320.1 mg (43.0%) as a yellow solid, m.p.: 149-151° C.

$^1$H-NMR, 400 MHz, CDCl$_3$, δ (ppm): 8.55 (s, 1H), 8.22 (m, 2H), 7.76 (m, 2H), 7.64 (d, J=4.1 Hz, 1H), 7.01 (d, J=4.1 Hz, 1H).

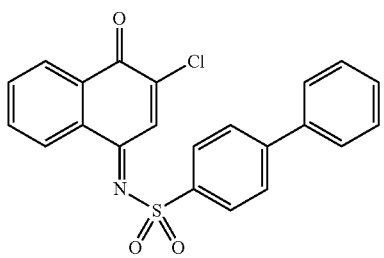

(12b)

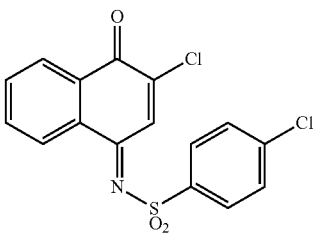

(12e)

N-(3-chloro-4-oxonaphthalen-1(4H)-ylidene)biphenyl-4-sulfonamide (12b) was prepared according to the procedure for 12a except using 4-biphenylsulfonamide, which afforded the title compound 154 mg (37.8%) as a yellow solid. When TiCl$_4$.2THF and THF were used instead, the reaction afforded the title compound 586.7 mg (71.9%) as a yellow solid, m.p.: 190-192° C.

$^1$H-NMR, 400 MHz, CDCl$_3$, δ (ppm): 8.71 (s, 1H), 8.21 (t, J=7.7 Hz, 2H), 8.14 (d, J=8.6 Hz, 2H), 7.81 (d, J=8.6 Hz, 2H), 7.74 (t, J=7.5 Hz, 1H), 7.70 (t, J=7.6 Hz, 1H), 7.65 (d, J=8.0 Hz, 2H), 7.51 (t, J=7.1 Hz, 2H), 7.45 (t, J=7.3 Hz, 1H).

4-chloro-N-(3-chloro-4-oxonaphthalen-1(4H)-ylidene)benzenesulfonamide (12e) was prepared according to the procedure for 12a except using 4-chlorobenzenesulfonamide, TiCl$_4$.2THF and THF as solvent which afforded the title compound 452.2 mg (61.8%) as a yellow solid, m.p.: 138-140° C.

$^1$H NMR, 400 MHz, CDCl$_3$, δ (ppm): 8.62 (s, 1H), 8.21 (dd, J=1.1 Hz, 7.7 Hz, 1H), 8.12 (dd, J=0.9 Hz, 7.6 Hz, 1H), 8.02 (d, J=8.7 Hz, 2H), 7.75 (td, J=1.3 Hz, 7.5 Hz, 1H), 7.70 (td, J=1.5 Hz, 7.6 Hz, 1H), 7.59 (d, J=8.8 Hz, 2H).

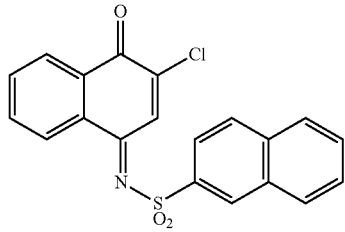

(12f)

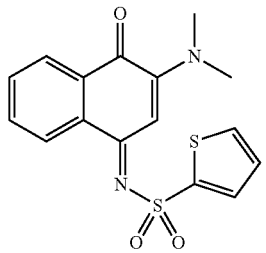

(13b)

N-(3-chloro-4-oxonaphthalen-1(4H)-ylidene)naphthalene-2-sulfonamide (12f) was prepared according to the procedure for (12a) except using naphthalene-2-sulfonamide, TiCl$_4$.2THF and THF as solvent which afforded the title compound 594.8 mg (77.9%) as a yellow solid, m.p.: 200-202° C.

$^1$H-NMR, 400 MHz, CDCl$_3$, δ (ppm): 8.73 (s, 1H), 8.64 (s, 1H), 8.20 (d, 7.7 Hz, 1H), 8.14 (d, J=7.9 Hz, 1H), 8.05 (m, 3H), 7.97 (d, 8.0 Hz, 1H), 7.72 (q, J=7.4 Hz, 2H), 7.66 (t, J=7.1 Hz, 2H).

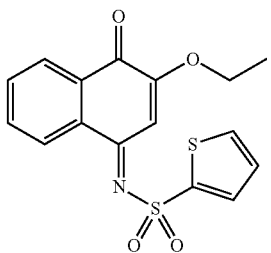

(13a)

5.2.36 N-(3-ethoxy-4-oxonaphthalen-1(4H)-ylidene)thiophene-2-sulfonamide (13a): 33.8 mg (E)-N-(3-chloro-4-oxonaphthalen-1(4H)-ylidene)thiophene-2-sulfonamide was suspended in 2 ml ethanol, to which was added 0.5 ml sodium ethoxide in ethanol solution (0.2 M). The suspension disappeared and in 5 min it turned cloudy with yellow precipitate. The resulting reaction mixture was concentrated and the crude product was purified by flash column (EtOAc/Hex) affording the title compound 10 mg (28.8%) as a bright yellow solid.

$^1$H-NMR, 400 MHz, CDCl$_3$, δ (ppm): 8.24 (m, 1H), 8.16 (m, 1H), 7.82 (d, J=2.5 Hz, 1H), 7.69 (m, 3H), 7.44 (s, 1H), 7.14 (dd, J=3.8 Hz, 4.9 Hz, 1H), 4.26 (q, J=7.0 Hz, 2H), 1.57 (t, J=7.0 Hz, 3H)

HRMS (ESI+ve) m/z calculated for C$_{16}$H$_{13}$NO$_4$S$_2$ (M+H)$^+$ 348.0359, found 348.0371.

N-(3-(dimethylamino)-4-oxonaphthalen-1(4H)-ylidene)thiophene-2-sulfonamide (13b): 33.5 mg (E)-N-(3-chloro-4-oxonaphthalen-1(4H)-ylidene)thiophene-2-sulfonamide was dissolved in 2 ml THF, to which was added 0.4 ml dimethylamine in THF solution (2 M). The wine-red solution was stirred at r.t. for 10 min and concentrated. The residue was suspended in 50 ml ethyl acetate and washed with water and brine. Dried over Na2SO4, the organic phase was filtered and the filtrate was concentrated to dryness affording the title compound 36 mg (100%) as a wine-red solid, m.p.: 183-185° C.

$^1$H-NMR, 400 MHz, CDCl$_3$, δ (ppm): 8.25 (d, J=7.7 Hz, 1H), 8.01 (d, J=7.6 Hz, 1H), 7.75 (d, J=3.7 Hz, 1H), 7.65 (t, J=7.3 Hz, 1H), 7.58 (m, 2H), 7.08 (t, J=5.0 Hz, 1H), 6.91 (s, 1H), 3.40 (s, 6H).

HRMS (ESI+ve) m/z calculated for C$_{16}$H$_{14}$N$_2$O$_3$S$_2$ (M+H)$^+$ 347.0519, found 347.0522.

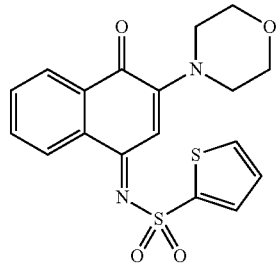

(13c)

N-(3-morpholino-4-oxonaphthalen-1(4H)-ylidene)thiophene-2-sulfonamide (13c) was prepared according to the procedure for 13b except using 0.2 eq. morpholine, which afforded the title compound 36.3 mg (93.6%) as a wine-red solid, m.p.: 195° C. (dec.).

$^1$H-NMR, 400 MHz, CDCl$_3$, δ (ppm): 8.21 (d, J=7.4 Hz, 1H), 8.01 (d, J=7.4 Hz, 1H), 7.77 (d, J=3.6 Hz, 1H), 7.63 (m, 3H), 7.13 (s, 1H), 7.10 (t, J=4.9 Hz, 1H), 3.88 (t, J=4.5 Hz, 4H), 3.77 (t, J=4.3 Hz, 4H).

HRMS (ESI+ve) m/z calculated for C$_{18}$H$_{16}$N$_2$O$_4$S$_2$ (M+H)$^+$ 389.0624, found 389.0628.

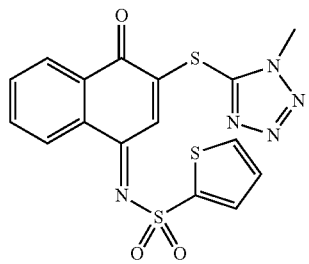

(13d)

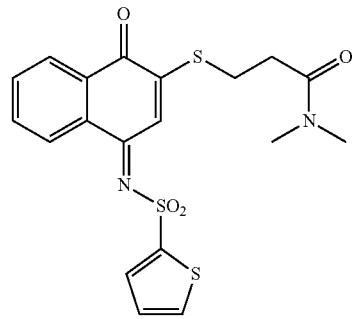 [SMILES: CN(C)C(=O)CCSC1=C/C(=N\S(=O)(=O)c2cccs2)c2ccccc2C1=O]

(13f)

N-(3-(1-methyl-1H-tetrazol-5-ylthio)-4-oxonaphthalen-1 (4H)-ylidene)thiophene-2-sulfonamide (13d): 36 mg (E)-N-(3-chloro-4-oxonaphthalen-1(4H)-ylidene)-thiophene-2-sulfonamide (12a) was dissolved in 3 ml THF, to which was added 11.7 mg 1-methyl-tetrazole-5-thiol. The reaction mixture was stirred at r.t. for 2 hrs and concentrated via rotavap. The residue was dissolved in dichloromethylene and triturated with hexane. The precipitate was filtered and washed with dichloromethylene/hexane (1:1) affording the title compound 28.8 mg (68.9%) as an orange-red solid, m.p.: 172° C. (dec.).

$^1$H-NMR, 400 MHz, CDCl$_3$, δ (ppm): 8.25 (m, 1H), 8.16 (m, 1H), 8.01 (s, 1H), 7.78 (d, J=3.8 Hz, 1H), 7.74 (m, 3H), 7.15 (dd, J=4.0 Hz, 4.9 Hz, 1H), 4.21 (s, 3H).

HRMS (ESI+ve) m/z calculated for C$_{16}$H$_{11}$N$_5$O$_3$S$_3$ (M+H)$^+$ 418.0097, found 418.0099.

N,N-dimethyl-3-(1-oxo-4-(thiophen-2-ylsulfonylimino)-1,4-dihydronaphthalen-2-ylthio)propanamide (13f) was prepared according to the procedure for 13d except using 4,5-dichloro-N-(3-chloro-4-oxonaphthalen-1(4H)-ylidene) thiophenesulfonamide (12c) and 3-mercapto-N,N-dimethylpropanamide( ), which afforded the title compound 16.1 mg (48%) as a white solid, m.p.: ° C.

$^1$H NMR (400 MHz, CDCl$_3$) δ 8.18-8.16 (m, 1H), 8.07-8.06 (m, 1H), 7.83 (s, 1H), 7.75 (dd, J=3.6, 1.2 Hz, 1H), 7.65-7.61 (m, 3H), 7.08 (dd, J=5.2, 4.0 Hz, 1H); 3.28 (t, J=6.8 Hz, 2H), 2.95 (s, 6H), 2.80 (t, J=6.8 Hz, 2H).

HRMS (ESI+ve) m/z calculated for C$_{19}$H$_{19}$N$_2$O$_4$S$_3$ (M+H)$^+$ 435.0502, found 435.0508.

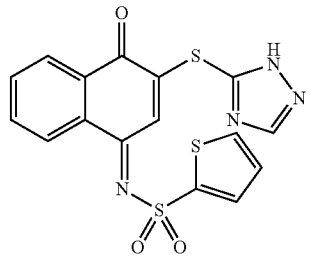

(13e)

N-(3-(1H-1,2,4-triazol-5-ylthio)-4-oxonaphthalen-1(4H)-ylidene)thiophene-2-sulfonamide (13e) was prepared according to the procedure for 13d except using 3-mercapto-1,2,4-triazole, which afforded the title compound 38.8 mg (96.5%) as an orange-red solid, m.p.: 197° C. (dec.).

$^1$H-NMR, 400 MHz, CD$_3$CN, δ (ppm): 8.63 (s, 1H), 8.18 (m, 1H), 8.15 (m, 1H), 7.89 (dd, J=1.3 Hz, 5.0 Hz, 1H), 7.81 (m, 3H), 7.55 (dd, J=1.3 Hz, 3.8 Hz, 1H), 7.21 (dd, J=3.0 Hz, 5.8 Hz, 1H).

HRMS (ESI+ve) m/z calculated for C$_{16}$H$_{10}$N$_4$O$_3$S$_3$ (M+H)$^+$ 402.9988, found 402.9989.

(13g)

(N-methyl-3-(1-oxo-4-(thiophen-2-ylsulfonylimino)-1,4-dihydronaphthalen-2-ylthio)propanamide (13g) was prepared according to the procedure for 13d except using 4,5-dichloro-N-(3-chloro-4-oxonaphthalen-1(4H)-ylidene) thiophenesulfonamide (12c) and 3-mercapto-N-methylpropanamide( ), which afforded the title compound 21 mg (32%) as a yellow solid, m.p.: ° C.

$^1$H NMR (400 MHz, CDCl$_3$) δ 8.23 (dd, J=5.6, 3.6 Hz, 1H), 8.15 (dd, J=5.6, 3.6 Hz, 1H), 7.85 (s, 1H), 7.83 (dd, J=3.6, 1.2 Hz, 1H), 7.74 (dd, J=5.2, 1.6 Hz, 1H), 7.71 (dd, J=6.0, 3.2 Hz, 1H); 7.17 (dd, J=6.0, 5.2, 2H), 6.19 (bs, 1H), 3.32 (t, J=8.0 Hz, 2H), 2.85 (d, J=4.8 Hz, 3H), 2.65 (t, J=8.0 Hz, 2H).

HRMS (ESI+ve) m/z calculated for C$_{18}$H$_{17}$N$_2$O$_4$S$_3$ (M+H)$^+$ 421.0345, found 421.0344.

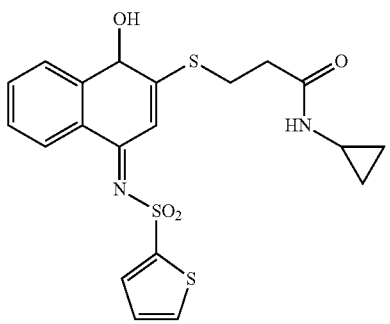 [SMILES: O=C(CCSC1=C/C(=N\S(=O)(=O)c2cccs2)c2ccccc2C1=O)NC1CC1]

(13h)

N-cyclopropyl-3-(1-oxo-4-(thiophen-2-ylsulfonylimino)-1,4-dihydronaphthalen-2-ylthio)propanamide (13h) was prepared according to the procedure for 13d except using 4,5-dichloro-N-(3-chloro-4-oxonaphthalen-1(4H)-ylidene)thiophenesulfonamide (12c) and 3-mercapto-N-cyclopropylpropanamide ( ), which afforded the title compound 20 mg (37%) as a yellow solid, m.p.: ° C.

$^1$H NMR (400 MHz, CDCl$_3$) δ 8.23 (dd, J=5.6, 3.2 Hz, 1H), 8.16 (dd, J=5.6, 3.2 Hz, 1H), 7.83 (dd, J=4.0, 1.6 Hz, 1H), 7.82 (s, 1H), 7.73 (dd, J=5.2, 1.6 Hz, 1H), 7.70 (dd, J=6.0, 3.6 Hz, 2H); 7.19 (dd, J=4.8, 4.0, 1H), 6.42 (bs, 1H), 3.31 (t, J=8.4 Hz, 2H), 2.82-2.78 (m, 1H), 2.60 (t, J=8.4 Hz, 2H), 0.78 (q, J=5.6 Hz, 2H), 0.60 (q, J=5.6 Hz, 2H).

HRMS (ESI+ve) m/z calculated for $C_{20}H_{19}N_2O_4S_3$ (M+H)$^+$ 447.0512, found 447.0505.

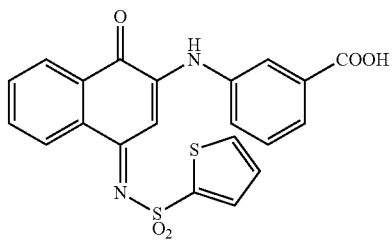

(13i)

3-(1-oxo-4-(thiophen-2-ylsulfonylimino)-1,4-dihydronaphthalen-2-ylamino)-benzoic acid (13i): 33.8 mg (E)-N-(3-(1-methyl-1H-tetrazol-5-ylthio)-4-oxonaphthalen-1(4H)-ylidene)thiophene-2-sulfonamide (12a) was dissolved in 3 ml THF, to which was added 13.7 mg 3-aminobenzoic acid. The resulting orange solution was stirred at r.t. for 30 min and 0.2 ml THF solution containing 1 eq. pyridine was added. The reaction was continued for 30 min. The mixture was diluted to 50 ml with ethyl acetate and washed with 0.5 N NaHSO$_4$ solution, water and brine. Dried over Na$_2$SO$_4$, the organic phase was filtered and the filtrate was concentrated. The residue was washed with dichloromethylene/hexane (1:1) affording the title compound 32.5 mg (74.2%) as a red solid, m.p.: 230° C. (dec.).

$^1$H-NMR, 400 MHz, CD$_3$CN, δ (ppm): 9.23 (br, 1H), 8.25 (d, J=7.8 Hz, 1H), 8.16 (d, J=7.2 Hz, 1H), 8.03 (s, 1H), 7.99 (d, J=7.5 Hz, 1H), 7.78 (m, 3H), 7.66 (t, J=8.0 Hz, 1H), 7.60 (m, 2H), 7.19 (d, J=2.7 Hz, 1H), 4.3 Hz, 1H).

HRMS (ESI–ve) m/z calculated for $C_{21}H_{14}N_2O_5S_2$ (M–H)$^-$ 437.0271, found 437.0276.

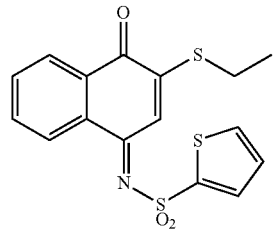

(13j)

N-(3-(ethylthio)-4-oxonaphthalen-1(4H)-ylidene)thiophene-2-sulfonamide (13j) was prepared according to the procedure for 13d except using ethanethiol, which, after purification via flash chromatography (Hex/EtOAc), afforded the title compound 25 mg (34.4%) as an orange-red solid, m.p.: ° C.

1H-NMR, 400 MHz, CDCl$_3$, δ (ppm): 8.23 (m, 1H), 8.15 (m, 1H), 7.90 (s, 1H), 7.82 (dd, J=1.3 Hz, 3.8 Hz, 1H), 7.69 (m, 3H), 7.15 (dd, J=3.8 Hz, 5.0 Hz, 1H), 3.02 (q, J=7.4 Hz, 2H), 1.50 (t, J=7.4 Hz, 3H).

HRMS (ESI–ve) m/z calculated for $C_{16}H_{13}NO_3S_3$ (M+H)$^+$ 364.0130, found 364.0136.

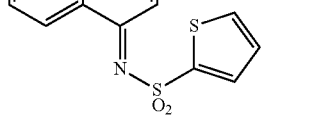

(13k)

N-(3-(2-hydroxyethylthio)-4-oxonaphthalen-1(4H)-ylidene)thiophene-2-sulfonamide (13k) was prepared according to the procedure for 13d except using 2-mercaptoethanol, which, after purification via flash chromatography (Hex/EtOAc), afforded the title compound 43 mg (56.7%) as an orange-red oil.

$^1$H-NMR, 400 MHz, CDCl$_3$, δ (ppm): 8.23 (m, 1H), 8.15 (m, 1H), 7.99 (s, 1H), 7.83 (dd, J=1.3 Hz, 3.8 Hz, 1H), 7.70 (m, 3H), 7.15 (dd, J=3.8 Hz, 5.0 Hz, 1H), 4.03 (t, J=6.1 Hz, 2H), 3.23 (t, J=6.1 Hz, 2H).

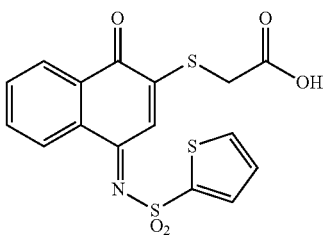

(13w)

(Z)-2-(1-oxo-4-(thiophen-2-ylsulfonylimino)-1,4-dihydronaphthalen-2-ylthio)acetic acid (13w): 188.3 mg 12a was dissolved in 5 ml THF, to which was added 0.56 ml THF solution containing 0.5 M pyridine followed by 0.56 ml THF solution containing 0.5 M 2-mercaptoglycolic acid. Another 0.56 ml THF solution containing 0.5 M pyridine was added followed by another 0.56 ml THF solution containing 0.5 M 2-mercaptoglycolic acid. The mixture was stirred at room temperature for 30 min. 114 mg DDQ was added and the mixture was stirred at room temperature overnight. The insoluble was filtered and the filtrate was concentrated. The crude residue was first purified via preparative TLC (2.5% CH$_3$OH/DCM) and then purified with manual flash chromatography (silica gel, 1.5% CH$_3$OH/0.5% CH$_3$COOH/DCM) affording a yellow solid 20.2 mg (9.2%) as the desired pure product and 80.9 mg (36.9%) mixture of the desired product and its reduced product. $^1$H NMR (400 MHz, CD$_3$CN) δ 8.20 (dd, J=6.1, 3.1 Hz, 1H), 8.12 (dd, J=6.1, 3.0 Hz, 1H), 7.92-7.90 (m, 2H), 7.87 (dd, J=3.8, 1.3 Hz, 1H), 7.82-7.77 (m, 2H), 7.24 (dd, J=5.0, 3.8 Hz, 1H), 3.88 (s, 2H). LRMS (ES−) 392 (M−H)$^-$; HRMS (ES−) m/z calculated for C$_{16}$H$_{10}$NO$_5$S$_3$ (M−H)$^-$ 391.9727, found 391.9729.

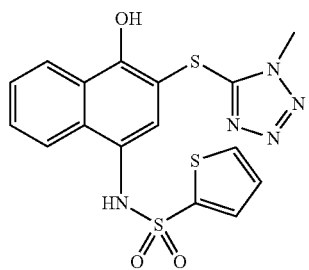

(14d)

N-(4-hydroxy-3-(1-methyl-1H-tetrazol-5-ylthio)naphthalen-1-yl)thiophene-2-sulfonamide (14d): 13 mg (E)-N-(3-(1-methyl-1H-tetrazol-5-ylthio)-4-oxonaphthalen-1(4H)-ylidene)thiophene-2-sulfonamide (13d) was dissolved in 50 ml ethyl acetate, to which was added 27 mg sodium hydrosulfite solid followed by 10 ml water. The mixture was shaken in a separation funnel until the yellow organic phase turned colorless. The organic phase was separated and washed with water and brine. Dried over Na2SO4, the organic phase was filtered and the filtrate was concentrated to dryness. The residue was dissolved in dichloromethylene and triturated with hexane. The precipitate was washed with dichloromethylene/hexane (1:1) affording the title compound 13 mg (99%) as a white solid, m.p.: 130° C. (dec.).

$^1$H-NMR, 400 MHz, CD$_3$CN, δ (ppm): 8.28 (dd, J=3.0 Hz, 6.7 Hz, 1H), 8.14 (s, 1H), 7.98 (dd, J=3.5 Hz, 6.2 Hz, 1H), 7.94 (br, 1H), 7.65 (dd, J=1.2 Hz, 5.0 Hz, 1H), 7.61 (dd, J=3.4 Hz, 6.5 Hz, 2H), 7.38 (dd, J=1.2 Hz, 3.7 Hz, 1H), 7.16 (s, 1H), 6.99 (ss, J=3.8 Hz, 4.9 Hz, 1H), 4.00 (s, 3H).

HRMS (ESI+ve) m/z calculated for C$_{16}$H$_{13}$N$_5$O$_3$S$_3$ (M+H)$^+$ 420.0253, found 420.0240.

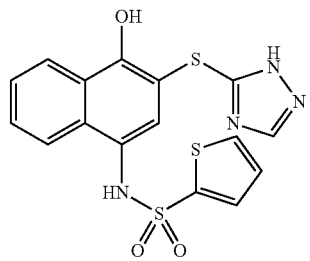

(14e)

N-(3-(1H-1,2,4-triazol-5-ylthio)-4-hydroxynaphthalen-1-yl)thiophene-2-sulfonamide (14e) was prepared according to the procedure for 14d except using (E)-N-(3-(1H-1,2,4-tria-zol-5-ylthio)-4-oxonaphthalen-1(4H)-ylidene)thiophene-2-sulfonamide (13e), which afforded the title compound 20 mg (100%) as a white solid, m.p.: 180° C. (dec.).

$^1$H-NMR, 400 MHz, d$^6$-DMSO, δ (ppm): 10.19 (br, 1H), 10.05 (s, 1H), 8.61 (br, 1H), 8.16 (d, J=7.6 Hz, 1H), 7.89 (d, J=7.4 Hz, 1H), 7.81 (d, J=4.2 Hz, 1H), 7.48 (t, J=7.9 Hz, 2H), 7.28 (d, J=2.5 Hz, 1H), 6.99 (t, J=4.2 Hz, 1H), 6.91 (br, 1H), HRMS (ESI-ve) m/z calculated for C$_{16}$H$_{12}$N$_4$O$_3$S$_3$ (M−H)$^-$ 402.9999, found 402.9989.

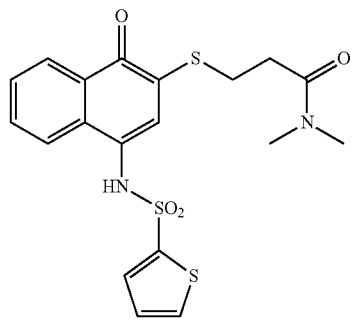

(14f)

3-(1-hydroxy-4-(thiophene-2-sulfonamido)naphthalen-2-ylthio)-N,N-dimethylpropanamide (14f) was prepared according to the procedure for 9a except using 13f affording 9.8 mg (98%) title compound, m.p.: ° C.

$^1$H NMR (400 MHz, CD$_3$CN) δ 8.32-8.29 (m, 1H), 7.97-7.95 (m, 1H), 7.83 (s, 1H), 7.71 (dd, J=5.2, 1.2 Hz, 1H), 7.54-7.52 (m, 2H), 7.40 (dd, J=3.6, 1.2 Hz, 1H); 7.08-7.06 (m, 2H), 2.30 (s, 3H), 2.98 (s, 3H), 2.93 (t, J=6.4 Hz, 2H), 2.57 (t, J=6.4 Hz, 2H).

HRMS (ESI+ve) m/z calculated for C$_{19}$H$_{21}$N$_2$O$_4$S$_3$ (M+H)$^+$ 437.0658, found 447.0606.

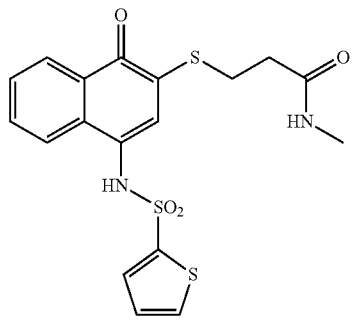

(14g)

5.2.51 3-(1-hydroxy-4-(thiophene-2-sulfonamido)naphthalen-2-ylthio)-N-methylpropanamide (14 g) was prepared according to the procedure for 9a except using 13g affording 7.8 mg (80%) title compound, m.p.: ° C.

$^1$H NMR (400 MHz, CD$_3$CN) δ 9.67 (s, 1H), 8.30-8.28 (m, 1H), 7.99-7.97 (m, 1H), 7.86 (s, 1H), 7.71 (dd, J=5.2, 1.6 Hz, 1H), 7.54 (dd, J=6.8, 3.6 Hz, 2H), 7.41 (dd, J=5.2, 1.6 Hz, 1H); 7.08-7.06 (m, 2H), 6.56 (bs, 1H), 3.81 (t, J=8.0 Hz, 2H), 2.75 (d, J=4.8 Hz, 3H), 2.30 (t, J=8.0 Hz, 2H).

HRMS (ESI+ve) m/z calculated for C$_{18}$H$_{19}$N$_2$O$_4$S$_3$ (M+H)$^+$ 423.0502, found 423.0478.

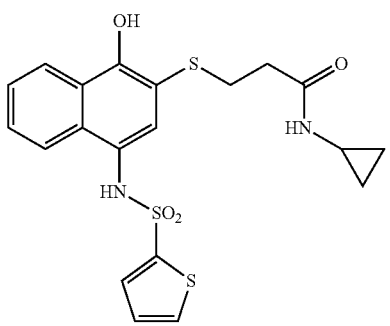 [SMILES: O=C(CCSc1cc(NS(=O)(=O)c2cccs2)c2ccccc2c1O)NC1CC1]

(14h)

N-cyclopropyl-3-(1-hydroxy-4-(thiophene-2-sulfonamido)naphthalen-2-ylthio)propanamide (14h) was prepared according to the procedure for 9a except using 13h affording 8.8 mg (89%) title compound, m.p.: ° C.

¹H NMR (400 MHz, CD₃CN) δ 9.50 (s, 1H), 8.29 (dd, J=5.6, 3.2 Hz, 1H), 7.99 (dd, J=5.6, 3.2 Hz, 1H), 7.85 (s, 1H), 7.70 (dd, J=3.6, 1.2 Hz, 1H), 7.55-7.53 (m, 2H), 7.41 (dd, J=3.6, 1.2 Hz, 1H), 7.08-7.05 (m 2H), 6.75 (bs, 1H), 2.92 (t, J=8.4 Hz, 2H), 2.74-2.68 (m, 1H), 2.46 (t, J=8.4 Hz, 2H), 0.68 (q, J=5.6 Hz, 2H), 0.47 (q, J=5.6 Hz, 2H).

HRMS (ESI+ve) m/z calculated for $C_{20}H_{21}N_2O_4S_3$ (M+H)⁺ 449.0658, found 449.0639.

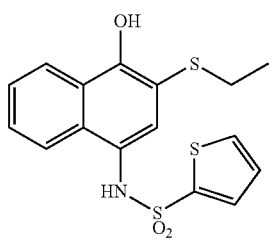

(14j)

N-(3-(ethylthio)-4-hydroxynaphthalen-1-yl)thiophene-2-sulfonamide (14j) was prepared according to the procedure for 14d except using (E)-N-(3-ethylthio-4-oxonaphthalen-1 (4H)-ylidene)thiophene-2-sulfonamide (13j), which afforded the title compound 14 mg (100%) as a grey solid, m.p.: ° C.

¹H-NMR, 400 MHz, CD₂Cl₂, δ (ppm): 8.24 (m, 1H), 7.90 (m, 1H), 7.58 (dd, J=1.2 Hz, 5.0 Hz, 1H), 7.53 (m, 2H), 7.46 (s, 1H), 7.39 (dd, J=1.3 Hz, 3.8 Hz, 1H), 7.28 (s, 1H), 7.00 (dd, J=3.8 Hz, 4.9 Hz, 1H), 6.71 (br, 1H), 2.71 (q, J=7.3 Hz, 2H), 1.17 (t, J=7.3 Hz, 3H).

HRMS (ESI+ve) m/z calculated for $C_{16}H_{15}NO_3S_3$ (M+Na)⁺ 388.0106, found 388.0107.

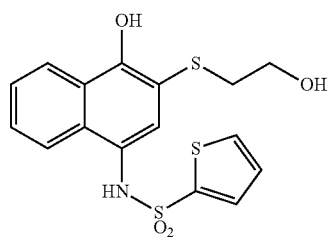

(14k)

N-(4-hydroxy-3-(2-hydroxyethylthio)naphthalen-1-yl) thiophene-2-sulfonamide (14k) was prepared according to the procedure for 14d except using N-(3-(2-hydroxyethylthio)-4-oxonaphthalen-1(4H)-ylidene)thiophene-2-sulfonamide (13k), which, after purification via flash chromatography (Hex/EtOAc), afforded the title compound 20.3 mg (53.1%) as a grey solid, m.p.: ° C.

¹H-NMR, 400 MHz, d⁶-DMSO, δ (ppm): 10.06 (s, 1H), 9.70 (s, 1H), 8.12 (d, J=7.7 Hz, 1H), 7.88 (m, 2H), 7.45 (m, 2H), 7.35 (dd, J=1.3 Hz, 3.7 Hz, 1H), 7.07 (dd, J=3.8 Hz, 5.0 Hz, 1H), 6.99 (s, 1H), 5.10 (t, J=5.1 Hz, 1H), 2.75 (t, J=6.7 Hz, 2H).

¹H-NMR, 400 MHz, CD₂Cl₂+CD₃CN, δ (ppm): 8.24 (m, 1H), 8.10 (br, 1H), 7.90 (m, 1H), 7.58 (dd, J=1.3 Hz, 5.0 Hz, 1H), 7.51 (m, 2H), 7.37 (dd, J=1.3 Hz, 3.7 Hz, 1H), 7.23 (s, 1H), 7.11 (br, 1H), 7.00 (dd, J=3.8 Hz, 5.0 Hz, 1H), 3.60 (t, J=5.9 Hz, 2H), 2.83 (t, J=5.8 Hz, 2H), 2.02 (br, 1H).

HRMS (ESI+ve) m/z calculated for $C_{16}H_{15}NO_4S_3$ (M+Na)⁺ 404.0055, found 404.0049.

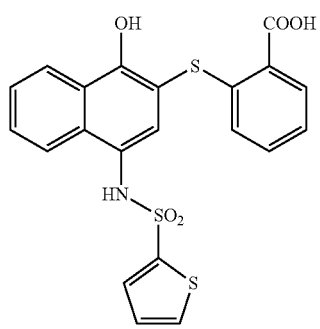

(14l)

5.2.55 2-(1-hydroxy-4-(thiophene-2-sulfonamido)naphthalen-2-ylthio)benzoic acid (14l) was prepared according to the procedure of procedure B for 10a except using thiosalicylic acid, which afforded the title compound 19 mg (99%) as a white solid, m.p.: 215° C. (dec.).

¹H-NMR, 400 MHz, d⁶-DMSO, δ (ppm): 13.13 (br, 1H), 10.09 (s, 1H), 8.20 (d, J=8.3 Hz, 1H), 8.01 (d, J=7.7 Hz, 1H), 7.93 (d, J=8.1 Hz, 1H), 7.76 (d, J=5.0 Hz, 1H), 7.54 (m, 2H), 7.33 (m, 2H), 7.18 (t, 7.5 Hz, 1H), 6.91 (m, 2H), 6.47 (d, J=8.5 Hz, 1H).

HRMS (ESI−ve) m/z calculated for $C_{21}H_{15}NO_5S_3$ (M−H)⁻ 456.0040, found 456.0025.

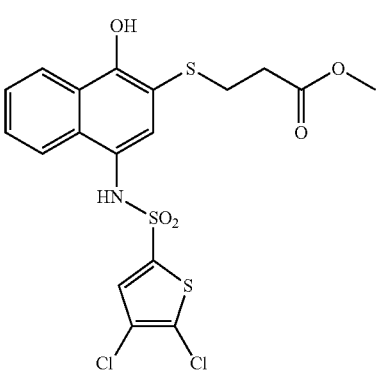

(14m)

Methyl-3-(4-(4,5-dichlorothiophene-2-sulfonamido)-1-hydroxynaphthalen-2-ylthio)propanoate (14m) was prepared according to the procedure of procedure B for 10a except using 4,5-dichloro-N-(3-chloro-4-oxonaphthalen-1(4H)- ylidene)thiophenesulfonamide (12c) and ethyl mercaptoacetate, which afforded the title compound 16.1 mg (33%) as a grey solid after flash chromatography (Hex/EtOAc), m.p.: ° C.

$^1$H NMR (400 MHz, CD$_3$CN) δ 8.24 (s, 1H), 8.22 (d, J=8.4 Hz, 1H), 7.87 (d, J=8.4 Hz, 1H), 7.65 (s, 1H), 7.60-7.51 (m, 2H), 7.29 (s, 2H); 3.66 (s, 3H), 2.94 (t, J=6.8 Hz, 2H), 2.73 (t, J=6.8 Hz, 2H).

HRMS (ESI-ve) m/z calculated for C$_{18}$H$_{14}$Cl$_2$NO$_5$S$_3$ (M−H)$^-$ 489.9417, found 489.9454.

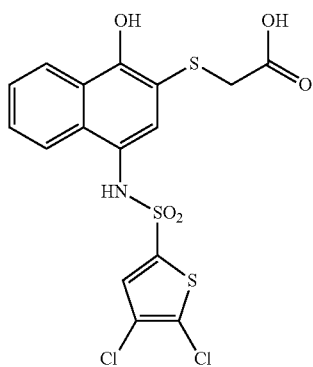

(14n)

2-(4-(4,5-dichlorothiophene-2-sulfonamido)-1-hydroxynaphthalen-2-ylthio)acetic acid (14n) was prepared according to the procedure of procedure B for 10a except using 4,5-dichloro-N-(3-chloro-4-oxonaphthalen-1(4H)-ylidene)thiophenesulfonamide (12c), which afforded the title compound 17.8 mg (39%) as a white solid, m.p.: ° C.

$^1$H NMR (400 MHz, DMSO-d$_6$) δ 10.63 (s, 1H), 10.36 (s, 1H), 8.18 (d, J=8.4 Hz, 1H), 7.81 (d, J=8.4 Hz, 1H), 7.53 (t, J=7.6 Hz, 1H), 7.49-7.45 (m, 2H), 7.14 (s, 1H).

HRMS (ESI-ve) m/z calculated for C$_{16}$H$_{10}$Cl$_2$NO$_5$S$_3$ (M−H)$^-$ 461.9104, found 461.9083.

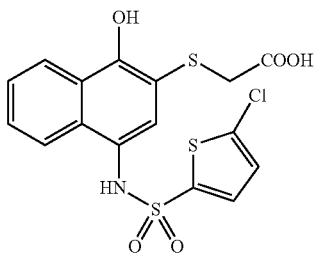

(14o)

2-(4-(5-chlorothiophene-2-sulfonamido)-1-hydroxynaphthalen-2-ylthio)acetic acid (14o) was prepared according to the procedure of procedure B for 10a except using (E)-5-chloro-N-(3-chloro-4-oxonaphthalen-1(4H)-ylidene)thiophene-2-sulfonamide (12d), which afforded the title compound 32.4 mg (54%) as a white solid, m.p.: 143-145° C.

$^1$H-NMR, 400 MHz, d$^6$-DMSO, δ (ppm): 12.73 (br, 1H), 10.28 (s, 1H), 9.97 (br, 1H), 8.15 (d, J=7.7 Hz, 1H), 7.85 (d, J=8.6 Hz, 1H), 7.47 (m, 2H), 7.22 (d, J=4.1 Hz, 1H), 7.13 (s, 1H), 7.12 (d, J=4.1 Hz, 1H), 3.56 (s, 2H).

HRMS (ESI-ve) m/z calculated for C$_{16}$H$_{12}$ClNO$_5$S$_3$ (M−H)$^-$ 427.9493, found 427.9461.

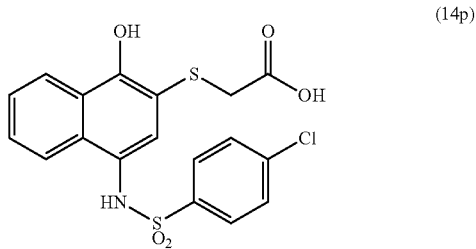

(14p)

2-(4-(4-chlorophenylsulfonamido)-1-hydroxynaphthalen-2-ylthio)acetic acid (14p) was prepared according to the procedure of procedure B for 10a except using (E)-4-chloro-N-(3-chloro-4-oxonaphthalen-1(4H)-ylidene)-benzenesulfonamide (12e), which afforded the title compound 57.7 mg (68.4%) as a white solid, m.p.: 158-160° C.

$^1$H-NMR, 400 MHz, d$^6$-DMSO, δ (ppm): 12.76 (br, 1H), 10.03 (s, 1H), 9.85 (br, 1H), 8.12 (d, J=8.2 Hz, 1H), 7.81 (d, J=8.4 Hz, 1H), 7.60 (d, J=8.7 Hz, 2H), 7.54 (d, J=8.8 Hz, 2H), 7.46 (t, J=7.5 Hz, 1H), 7.41 (t, J=7.5 Hz, 1H), 7.01 (s, 1H), 3.5 (s, 2H).

HRMS (ESI-ve) m/z calculated for C$_{18}$H$_{14}$ClNO$_5$S$_2$ (M−H)$^-$ 421.9929, found 421.9955.

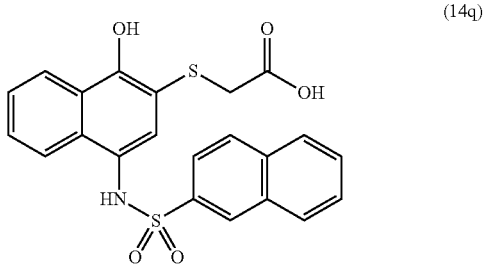

(14q)

5.2.60  2-(1-hydroxy-4-(naphthalene-2-sulfonamido)naphthalen-2-ylthio)acetic acid (14q) was prepared according to the procedure of procedure B for 10a except using (E)-N-(3-chloro-4-oxonaphthalen-1(4H)-ylidene)naphthalene-2-sulfonamide (12f), which afforded the title compound 64.3 mg (73.5%) as a white solid, m.p.: 185-187° C.

$^1$H-NMR, 400 MHz, d$^6$-DMSO, δ (ppm): 12.72 (br, 1H), 10.02 (s, 1H), 9.75 (br, 1H), 8.20 (s, 1H), 8.07 (t, J=8.3 Hz, 2H), 8.01 (d, J=8.3 Hz, 1H), 7.98 (d, J=8.4 Hz, 1H), 7.90 (d, J=8.2 Hz, 1H), 7.75 (d, J=8.7 Hz, 1H), 7.65 (t, J=7.5 Hz, 1H), 7.58 (t, J=7.6 Hz, 1H), 7.40 (t, J=7.2 Hz, 1H), 7.35 (t, J=7.3 Hz, 1H), 6.97 (s, 1H).

$^1$H-NMR, 400 MHz, CD$_3$CN, δ (ppm): 8.22 (m, 1H), 8.19 (s, 1H), 8.02 (m, 3H), 7.93 (d, J=7.9 Hz, 1H), 7.81 (s, 1H), 7.78 (d, J=8.9 Hz, 1H), 7.69 (t, J=7.5 Hz, 1H), 7.62 (t, J=7.2 Hz, 1H), 7.49 (m, 2H), 6.99 (s, 1H), 3.28 (s, 2H).

HRMS (ESI-ve) m/z calculated for C$_{22}$H$_{17}$NO$_5$S$_2$ (M−H)$^-$ 438.0475, found 438.0500.

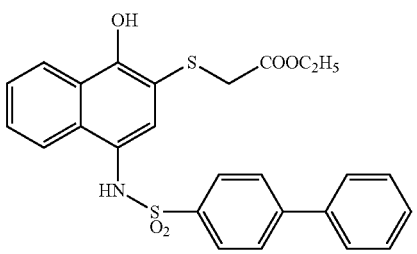

(14r)

Ethyl 2-(4-(biphenyl-4-ylsulfonamido)-1-hydroxynaphthalen-2-ylthio)acetate (14r) was prepared according to the procedure of procedure B for 10a except using (E)-N-(3-chloro-4-oxonaphthalen-1(4H)-ylidene)biphenyl-4-sulfonamide (12b) and ethyl mercapto-acetate, which afforded the title compound 71.5 mg (85.5%) as an off-white solid, m.p.: 166-168° C.

$^1$H-NMR, 400 MHz, CDCl$_3$, δ (ppm): 8.40 (s, 1H), 8.27 (m, 1H), 7.85 (m, 1H), 7.76 (d, J=8.4 Hz, 2H), 7.59 (d, J=8.4 Hz, 2H), 7.55 (d, J=6.9 Hz, 2H), 7.46 (m, 4H), 7.41 (t, J=7.1 Hz, 1H), 7.28 (s, 1H), 6.83 (s, 1H), 4.15 (q, J=7.1 Hz, 2H), 3.41 (s, 2H), 1.20 (t, J=7.1 Hz, 3H).

HRMS (ESI–ve) m/z calculated for C$_{26}$H$_{23}$NO$_5$S$_2$ (M+Na)$^+$ 516.0910, found 516.0903.

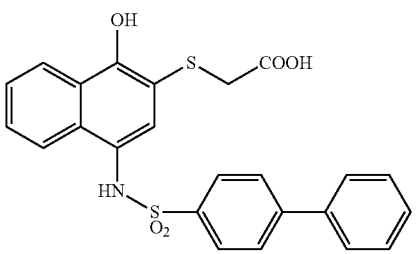

(14s)

5.2.62 2-(4-(biphenyl-4-ylsulfonamido)-1-hydroxynaphthalen-2-ylthio)acetic acid (14s) was prepared according to the procedure of procedure B for 10a except using ethyl 2-(4-(biphenyl-4-ylsulfonamido)-1-hydroxynaphthalen-2-ylthio)acetate (14r) and applying r.t. overnight to the reaction, which afforded the title compound 19.2 mg (40.7%) as a grey solid, m.p.: 170° C. (dec.).

$^1$H-NMR, 400 MHz, d$^6$-DMSO, δ (ppm): 12.76 (br, 1H), 9.96 (s, 1H), 9.81 (br, 1H), 8.11 (d, J=7.7 Hz, 1H), 7.89 (d, J=7.6 Hz, 1H), 7.77 (d, J=8.2 Hz, 2H), 7.67 (m, 4H), 7.45 (m, 5H), 7.01 (s, 1H), 3.47 (s, 2H).

HRMS (ESI–ve) m/z calculated for C$_{24}$H$_{19}$NO$_5$S$_2$ (M–H)$^-$ 464.0632, found 464.0638.

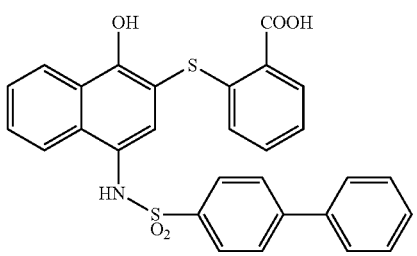

(14t)

2-(4-(biphenyl-4-ylsulfonamido)-1-hydroxynaphthalen-2-ylthio)benzoic acid (14t) was prepared according to the procedure of procedure B for 10a except using 2-thiosalicylic acid and (E)-N-(3-chloro-4-oxonaphthalen-1(4H)-ylidene) biphenyl-4-sulfonamide (12b), which afforded the title compound 17.4 mg (65.9%) as an off-white solid, m.p.: 205° C. (dec.).

$^1$H-NMR, 400 MHz, d$^6$-DMSO, δ (ppm): 13.12 (br, 1H), 10.07 (br, 1H), 9.90 (s, 1H), 8.20 (d, J=8.8 Hz, 1H), 8.12 (d, J=8.2 Hz, 1H), 7.92 (d, J=7.9 Hz, 1H), 7.65 (d, J=8.5 Hz, 2H), 7.60 (d, J=8.3 Hz, 2H), 7.54 (m, 2H), 7.40 (m, 6H), 7.13 (t, 7.8 Hz, 1H), 6.72 (s, 1H), 6.42 (d, J=8.1 Hz, 1H).

HRMS (ESI–ve) m/z calculated for C$_{29}$H$_{21}$NO$_5$S$_2$ (M–H)$^-$ 526.0788, found 526.0788.

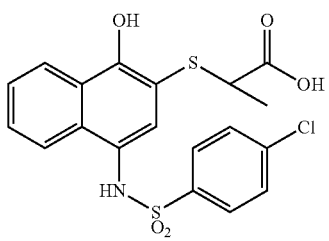

(14u)

2-(4-(4-chlorophenylsulfonamido)-1-hydroxynaphthalen-2-ylthio)propanoic acid (14u) was prepared according to the procedure of procedure B for 10a except using thiolactic acid and (E)-4-chloro-N-(3-chloro-4-oxonaphthalen-1(4H)-ylidene)-benzenesulfonamide (12e), which afforded the title compound 41.3 mg (49%) as a white solid, m.p.: 177-179° C.

$^1$H-NMR, 400 MHz, CD$_3$CN, δ (ppm): 8.22 (m, 1H), 7.93 (m, 1H), 7.84 (s, 1H), 7.64 (d, J=8.6 Hz, 2H), 7.55 (m, 2H), 7.47 (d, J=8.5 Hz, 2H), 7.10 (s, 1H), 3.64 (q, J=7.2 Hz, 1H), 1.35 (d, J=7.2 Hz, 3H).

HRMS (ESI–ve) m/z calculated for C$_{19}$H$_{16}$ClNO$_5$S$_2$ (M–H)$^-$ 436.0086, found 436.0106.

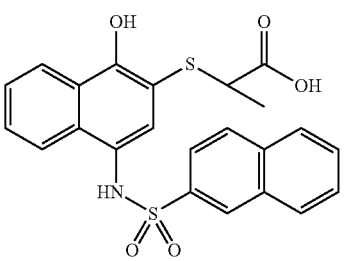

(14v)

2-(1-hydroxy-4-(naphthalene-2-sulfonamido)naphthalen-2-ylthio)propanoic acid (14v) was prepared according to the procedure of procedure B for 10a except using thiolactic acid and (E)-N-(3-chloro-4-oxonaphthalen-1(4H)-ylidene)naphthalene-2-sulfonamide (12f), which afforded the title compound 51.3 mg (58.6%) as an off-white solid, m.p.: 176-178° C.

$^1$H-NMR, 400 MHz, d$^6$-DMSO, δ (ppm): 12.70 (br, 1H), 10.01 (s, 1H), 9.74 (br, 1H), 8.18 (s, 1H), 8.10 (m, 2H), 7.99 (m, 3H), 7.80 (dd, J=1.6 Hz, 8.7 Hz, 1H), 7.65 (t, J=7.5 Hz, 1H), 7.58 (t, J=7.6 Hz, 1H), 7.43 (m, 2H), 6.88 (s, 1H), 0.87 (d, J=7.1 Hz, 3H).

$^1$H-NMR, 400 MHz, CD$_3$CN, δ (ppm): 8.19 (m, 2H), 8.04 (m, 2H), 7.99 (d, J=8.2 Hz, 1H), 7.92 (d, J=8.2 Hz, 1H), 7.85

(s, 1H), 7.81 (dd, J=1.6 Hz, 8.7 Hz, 1H), 7.68 (t, J=7.6 Hz, 1H), 7.61 (t, J=7.5 Hz, 1H), 7.50 (m, 2H), 7.00 (s, 1H), 3.36 (q, J=7.2 Hz, 1H), 1.09 (d, J=7.2 Hz, 3H).

HRMS (ESI-ve) m/z calculated for $C_{23}H_{19}NO_5S_2$ $(M-H)^-$ 452.0632, found 452.0621.

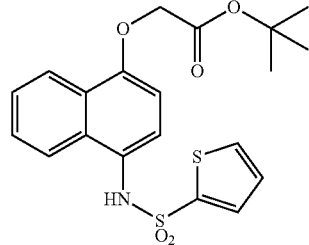

(15a)

tert-butyl 2-(4-(thiophene-2-sulfonamido)naphthalen-1-yloxy)acetate (15a): 61.1 mg 3 was dissolved in 1 ml DMF, to which was added 60 µl tert-butyl bromoacetate followed by 0.4 ml DBU solution (1M in NMP) and catalytic amount of KI. The mixture was heated with microwave initiator (biotage) to 90° C. and reacted for 20 min. TLC indicated the reaction didn't go complete. Additional 13.5 eq. of tert-butyl bromoacetate was added. The mixture was continued at 90° C. for 30 min. The mixture was diluted with ethyl acetate to 40 ml and washed with 0.5 M $NaHSO_4$, $H_2O$ and brine. Dried over $Na_2SO_4$, the organic phase was concentrated and the residue was purified via flash chromatography (5 g silica gel, Hex/EtOAc) affording 43 mg (51.3%) solid. $^1$H NMR (400 MHz, $CDCl_3$) δ 7.85 (d, J=7.8 Hz, 1H), 7.80 (dd, J=8.1, 1.2 Hz, 1H), 7.61 (dd, J=5.0, 1.3 Hz, 1H), 7.56 (dd, J=3.8, 1.3 Hz, 1H), 7.46-7.36 (m, 2H), 7.16 (d, J=8.4 Hz, 1H), 6.99 (dd, J=5.0, 3.8 Hz, 1H), 6.31 (d, J=8.4 Hz, 1H), 3.92 (s, 2H), 1.52 (s, 9H).; LRMS (ES+) 420 $(M+H)^+$; HRMS (ES+) m/z calculated for $C_{20}H_{22}NO_5S_2$ $(M+H)^+$ 420.0934, found 420.0932.

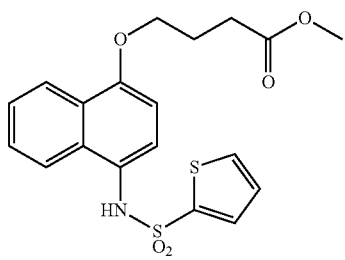

(15b)

methyl 4-(4-(thiophene-2-sulfonamido)naphthalen-1-yloxy)butanoate (15b): 15b was synthesized according to the procedure for 15a except 15 eq. of ethyl bromobutanoate was used and reaction was carried out at 90° C. for 30 min×2. After flash chromatography, 43 mg product was obtained in the yield of 51.3%. $^1$H NMR (400 MHz, $CDCl_3$) δ 7.84-7.79 (m, 1H), 7.77 (m, 1H), 7.62 (dd, J=5.0, 1.3 Hz, 1H), 7.58 (dd, J=3.8, 1.3 Hz, 1H), 7.44-7.36 (m, 2H), 7.14 (d, J=8.4 Hz, 0H), 7.00 (dd, J=5.0, 3.9 Hz, 1H), 6.44 (d, J=8.4 Hz, 1H), 4.15 (q, J=7.1 Hz, 1H), 3.31 (t, J=6.7 Hz, 1H), 2.52 (t, J=6.8 Hz, 1H), 2.11 (p, J=6.7 Hz, 1H), 1.25 (t, J=7.1 Hz, 4H).

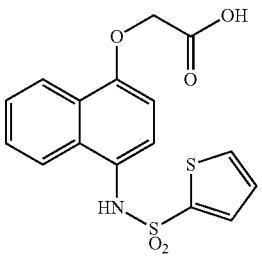

(16a)

5.2.68 2-(4-(thiophene-2-sulfonamido)naphthalen-1-yloxy)acetic acid (16a): 30 mg 15a was dissolved in 2 ml DCM, to which was added 1 ml TFA. The resulting mixture was stirred at room temperature for 1 h. TLC indicated the reaction didn't complete. The solution was concentrated and the residue was re-dissolved in 1 ml dioxane. 1 ml concentrated HCl was added. The mixture was stirred at room temperature for 1 hour and concentrated to dryness. The residue was suspended in 2 ml DCM/Hex (1:1). After standing in fridge overnight, the precipitate was collected by filtration and washed with 3 ml DCM/Hex (1:1) affording 21.4 mg (82.3%). $^1$H NMR (400 MHz, DMSO) δ 12.63 (br s, 1H), 8.13 (m, 1H), 8.11 (dd, J=5.0, 1.4 Hz, 1H), 7.78 (dd, J=3.8, 1.4 Hz, 1H), 7.68-7.62 (m, 1H), 7.48-7.41 (m, 2H), 7.20 (dd, J=5.0, 3.9 Hz, 1H), 7.01 (d, J=8.5 Hz, 1H), 6.80 (br s, 1H), 6.23 (d, J=8.6 Hz, 1H), 3.96 (s, 2H). LRMS (ES-) 362 $(M-H)^-$; HRMS (ES-) m/z calculated for $C_{16}H_{12}NO_5S_2$ $(M-H)^-$ 362.0162, found 362.0174.

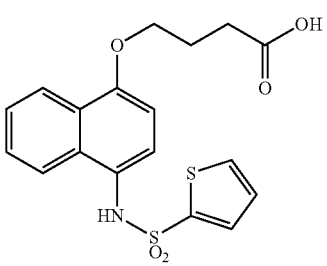

(16b)

4-(4-(thiophene-2-sulfonamido)naphthalen-1-yloxy)butanoic acid (16b): 16a was synthesized according to the procedure for 15b except 16a and 2 ml dioxane/4 ml concentrated HCl were used. 22.7 mg product was obtained in the yield of 56.6%. $^1$H NMR (400 MHz, DMSO) δ 12.11 (br s, 1H), 8.18 (m, 1H), 8.10 (dd, J=4.8, 0.9 Hz, 1H), 7.77 (dd, J=3.6, 0.9 Hz, 1H), 7.67-7.60 (m, 1H), 7.46-7.37 (m, 2H), 7.19 (dd, J=4.6, 4.2 Hz, 1H), 7.00 (d, J=8.5 Hz, 1H), 6.40 (m, 2H), 3.18 (m, 2H), 2.36 (t, J=7.2 Hz, 2H), 1.93-1.82 (m, 2H). LRMS (ES-) 390 $(M-H)^-$, HRMS (ES-) m/z calculated for $C_{18}H_{16}NO_5S_2$ $(M-H)^-$ 390.0475, found 390.0476.

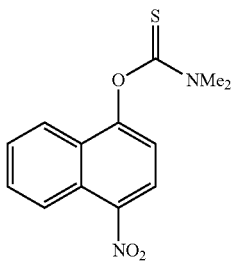

(18)

O-4-nitronaphthalen-1-yl dimethylcarbamothioate (18): 378.3 mg 4-nitronaphth-1-ol was dissolved in 2 ml NMP, to which was added 276 mg $K_2CO_3$. The mixture was heated to 50° C. To the solution was added dropwise a solution of 259.6 mg N,N-dimethyl thiochloroformate in 1 ml NMP. The resulting solution was stirred at 50° C. for 2 hours. The mixture was then quenched with 30 ml water at 50° C. The brown precipitate was filtered and washed with water. After dried in air, 496 mg product was obtained in the yield of 89.8%. $^1$H NMR (400 MHz, $CDCl_3$) δ 8.67 (d, J=8.8 Hz, 1H), 8.33 (d, J=8.4 Hz, 1H), 7.96 (d, J=8.1 Hz, 1H), 7.77-7.72 (m, 1H), 7.64 (ddd, J=8.2, 6.9, 1.1 Hz, 1H), 7.30 (d, J=8.4 Hz, 1H), 3.53 (s, 3H), 3.53 (s, 3H).

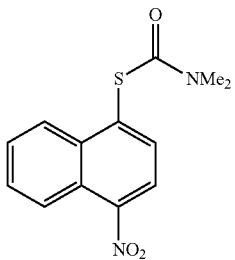

(19)

S-4-nitronaphthalen-1-yl dimethylcarbamothioate (19): 276.3 mg 18 was dissolved in 2 ml NMP. The solution was heated to 180° C. for 20 min with microwave initiator (biotage). The reaction mixture was diluted with ethyl acetate to 50 ml and washed with water and brine. Dried over $Na_2SO_4$, the organic phase was concentrated and the crude product was purified via flash chromatography (10 g silica gel, Hex/EtOAc) affording 197.5 mg (71.5%) brown solid. $^1$H NMR (400 MHz, $CDCl_3$) δ 8.52-8.46 (m, 1H), 8.13 (d, J=7.9 Hz, 1H), 7.87 (d, J=7.9 Hz, 1H), 7.76-7.66 (m, 1H), 3.24 (s, 3H), 3.03 (s, 3H).

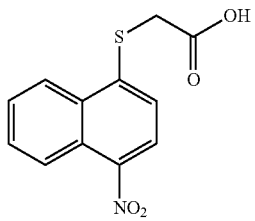

(20)

2-(4-nitronaphthalen-1-ylthio)acetic acid (20): 97 mg 19 was suspended in 1 ml methanol, to which, in Argon atmosphere, was added 1.4 ml KOH solution (1M in $CH_3OH$). The resulting mixture was stirred at room temperature for 12 hours affording a homogenous solution. 103 µl tert butyl bromoacetate was added through syringe. The reaction solution was continued for 12 hours and concentrated. The residue was dissolved in water and acidified with solid $NaHSO_4$. The yellow precipitate was filtered and washed with water. Dried in air, 78.8 mg (85.6%, 2 steps) yellow solid was obtained. $^1$H NMR (400 MHz, $CDCl_3$) δ 8.63 (d, J=8.4 Hz, 1H), 8.40 (d, J=8.4 Hz, 1H), 8.18 (d, J=8.1 Hz, 1H), 7.77 (t, J=7.6 Hz, 1H), 7.69 (t, J=7.6 Hz, 1H), 7.53 (d, J=8.4 Hz, 1H), 3.91 (s, 2H). LRMS (ES-) 218 (M—H—$CO_2$)$^-$; HRMS (ES-) m/z calculated for $C_{12}H_8NO_4S$ (M-H)$^-$ 262.0180, found 262.0180.

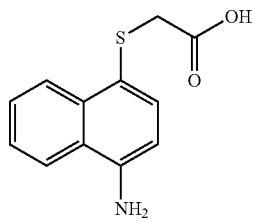

(21)

2-(4-aminonaphthalen-1-ylthio)acetic acid (21): 70 mg 20 was dissolved in 50 ml methanol. The solution was pumped at a rate of 1.0 ml/min through H-cube (25° C., 40 barr, full H2 mode) affording a colorless solution which turned in air slightly brown. The solution was concentrated to dryness affording a quantitative yield of the product 69.5 mg as a grey solid. $^1$H NMR (400 MHz, $CD_3OD$) δ 8.48 (d, J=8.4 Hz, 1H), 8.01 (d, J=8.5 Hz, 1H), 7.60 (d, J=7.8 Hz, 1H), 7.54 (ddd, J=8.3, 6.8, 1.2 Hz, 1H), 7.44 (ddd, J=8.1, 6.8, 1.2 Hz, 1H), 6.72 (d, J=7.9 Hz, 1H), 3.42 (s, 2H). LRMS (ES-) 188 (M—H—$CO_2$)$^-$; HRMS (ES-) m/z calculated for $C_{12}H_{10}NO_2S$ (M-H)$^-$ 232.0438, found 232.0435.

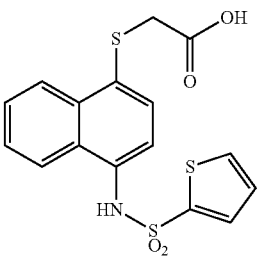

(22)

2-(4-(thiophene-2-sulfonamido)naphthalen-1-ylthio)acetic acid (22): 32.5 mg 21 was dissolved in 1 ml THF, to which at 0° C. was added 0.28 ml pyridine solution (0.5 M in THF) followed by 0.5 ml water. Upon stirring, 25.6 mg thiophene-2-sulfonyl chloride in 1 ml THF was added dropwise. Additional 0.28 ml pyridine solution was added. The resulting solution was stirred vigorously at 0° C. and slowly warmed to room temperature. After 4 hours, the organic solvent was removed. The aqueous portion was diluted with 10 ml water and acidified at 0° C. with NaHSO$_4$ solution (0.5 M). The mixture was extracted with ethyl acetate. The organic phase was combined, washed with water and brine and dried over Na$_2$SO$_4$. After removal of Na$_2$SO$_4$, the organic phase was concentrated and the crude product was purified via flash chromatography (5 g silica gel, DCM/CH$_3$OH=20:1) affording 31 mg (58.4%) grey solid. $^1$H NMR (400 MHz, CD$_3$CN) δ 8.36 (d, J=8.4 Hz, 1H), 8.00 (d, J=8.5 Hz, 1H), 7.68 (dd, J=5.0, 1.3 Hz, 1H), 7.62 (ddd, J=8.3, 6.8, 1.2 Hz, 1H), 7.54 (m, 2H), 7.43 (dd, J=3.8, 1.3 Hz, 1H), 7.28 (d, J=7.9 Hz, 1H), 7.04 (dd, J=5.0, 3.8 Hz, 1H), 3.78 (s, 2H). LRMS (ES−) 378 (M−H)$^-$; HRMS (ES−) m/z calculated for C$_{16}$H$_{12}$NO$_4$S$_3$ (M−H)$^-$ 377.9934, found 377.9937.

Proteasome Inhibition Assay

The assay was conducted by using a fluorogenic peptide as substrate to test synthesized compounds for inhibitory activity against the chymotrypsin-like activity of the purified rabbit 20S proteasome. Briefly, 70 ng of purified 20S proteasome was incubated with 20 μM Suc-Leu-Leu-Val-Tyr-AMC for 1 hour at 37° C. in 100 μl of assay buffer (50 mM Tris-HCl, pH 7.6) with or without inhibitors. After incubation, production of hydrolyzed 7-amido-4-methyl-coumarin (AMC) was measured using a WALLAC Victor2 1420 Multilabel Counter with an excitation filter of 355 nm and an emission filter of 460 nm (Perkin Elmer Life Sciences, Turku, Finland). The inhibitory activity of the compounds was calculated based on vehicle control.

TABLE 1

HLM008182 and analogues (Group I)

| Name<br>Molecular Wt/<br>Structure | IC$_{50}$ (μM)* | Chymotrypsin-like Activity<br>IC$_{50}$ (μM)-Inhibition at 30 μM | |
|---|---|---|---|
| HLM008182<br>(5591-2854)<br><br>M.W. = 395.47<br>2.02 mg submitted on Jun. 19, 2008<br>1.14 mg submitted on May 19, 2009 | | 1.5 (M-1096)<br>0.68 (M-1098)<br>0.25 (M-1099)<br>0.9 (AK)<br>0.71 (AK)<br>0.605 (AK)<br>0.475 (AK)<br>0.092 (AK)<br>1.45<br>1.8<br>0.651 ± 0.402 (n = 8)<br>0.112 (AK) (T-L activity)<br>0.172 (AK) (PGPH activity) | (Jun. 25, 2008)<br><br><br><br><br><br><br><br>(Aug. 14, 2009) |
| YG1-066 (in-house synthesis of HLM008182)<br><br>M.W. = 395.47<br>2.58 mg submitted on Jun. 19, 2008<br>1.26 mg resubmitted on Jan. 28, 2009 | 7.3<br>(Oct. 19, 2009)<br>8.9 | 1.1 (M-1096)<br>1.7 (M-1098)<br>0.54 (M-1099)<br>1.55 (AK)<br>1.42 (AK)<br>2.38 (AK)<br>3.25 (AK)<br>0.57<br>0.75<br>0.67<br>0.64<br>1.34<br>1.00<br>2.05<br>1.45<br>1.30 ± 0.76 (n = 13) | (Jun. 25, 2008)<br><br><br>(Jul. 22, 2008)<br><br>(Nov. 19, 2008)<br><br>(Feb. 17, 2009)<br><br>(Apr. 07, 2009)<br><br><br><br><br>(Aug. 14, 2009) |

TABLE 1-continued

HLM008182 and analogues (Group I)

| Name Molecular Wt/ Structure | $IC_{50}$ (μM)* | Chymotrypsin-like Activity $IC_{50}$ (μM)-Inhibition at 30 μM | |
|---|---|---|---|
| YG1-136 (in-house synthesis of HLM-008182) | | 0.7<br>2.26<br>2.5<br>1.56 (AK)<br>4.0 (AK)<br>2.20 ± 1.09 (n = 5)<br>6.5<br>6.75<br>1.64 (r.t. 2 weeks in DMSO)<br>2.76 (r.t. 2 weeks in DMSO)<br>2.04<br>3.94 | (Nov. 19, 2008)<br>(Jan. 08, 2009)<br><br>(Jan. 14, 2009)<br><br><br>Jan. 21, 2010)<br><br>Jan. 28, 2010)<br><br>(Jan. 28, 2010) |
| M.W. = 395.47<br>1.25 mg submitted on Oct. 21, 2008<br>0.83 mg submitted on Jan. 15, 2010<br>10 mM solution submitted on Jan. 26, 2010<br>1.11 mg fresh powder submitted on Jan. 26, 2010 | | | |
| YG2-176 | 8.9<br>(Oct. 19, 2010)<br>6.9 | 2.28<br>2.12<br>2.40<br>2.27 ± 0.14 (n = 3) | (Aug. 31, 2009) |
| M.W. = 393.48<br>1.28 mg submitted on Jul. 23, 2009 | | | |
| YG2-133-2 | | 4.25<br>2.75 | (Sep. 05, 2009) |
| M.W. = 377.80<br>1.72 mg submitted on Aug. 26, 2009 | | | |

TABLE 1-continued

HLM008182 and analogues (Group I)

| Name Molecular Wt/ Structure | IC$_{50}$ (μM)* | Chymotrypsin-like Activity IC$_{50}$ (μM)-Inhibition at 30 μM | | |
|---|---|---|---|---|
| YG2-120 | 1.10 | | (Aug. 14, 2009) | |
| | 1.79 | | | |

M.W. = 377.46
1.63 mg resubmitted on May 19, 2009

| PI-083 | 4.3 | 2.1 (M-1096) | (Jun. 25, 2008) | 87% |
| | (Oct. 19, 2010) | 1.4 (M-1098) | | 86% |
| | 3.7 | 2.5 (M-1099) | | 83% |
| | | 0.9 | (Feb. 17, 2009) | |
| | | 1.73 ± 0.618 (n = 4) | | |

M.W. = 439.87

| Velcade | | 0.021 (M-1096) | (Jun. 25, 2008) | |
| | | 0.024 (M-1096) | | |
| | | 0.030 (M-1098) | | |
| | | 0.034 (M-1099) | | |
| | | 0.0082 | (Feb. 17, 2009) | |
| | | 0.0234 ± 0.0089 (n = 5) | | |

| YG1-094 | | 1.6 | (Sep. 01, 2008) | |
| | | >10 | (Nov. 19, 2008) | |
| | | 2.8 | (Jan. 08, 2009) | |
| | | 3 | | |
| | | 1.5 | (Jan. 14, 2009) | |
| | | 2.5 | | |
| | | 2.28 ± 0.618 (n = 5) | | |

M.W. = 421.51
1.96 mg submitted on Aug. 12, 2008

TABLE 1-continued

HLM008182 and analogues (Group I)

| Name<br>Molecular Wt/<br>Structure | $IC_{50}$ (μM)* | Chymotrypsin-like Activity<br>$IC_{50}$ (μM)-Inhibition at 30 μM | |
|---|---|---|---|
| YG1-112<br><br>M.W. = 421.51<br>1.77 mg submitted on Sep. 05, 2008<br>2.11 mg resubmitted on Jan. 21, 2009 | | 2.2<br>5.9<br>6.1<br>>10<br>>10<br>6<br>3<br>4.64 ± 1.69 (n = 5) | (Nov. 19, 2008)<br>(Jan. 08, 2009)<br>(Jan. 14, 2009)<br>(Feb. 17, 2009) |
| YG1-107<br><br>M.W. = 423.53<br>1.50 mg submitted on Sep. 05, 2008<br>1.84 mg resubmitted on Jan. 21, 2009 | | 2.28<br>2.26<br>6.6<br>3.9<br>7.1<br>5.1<br>7.7<br>4.99 ± 2.08 (n = 7) | (Nov. 19, 2008)<br>(Jan. 08, 2009)<br>(Jan. 14, 2009)<br>(Feb. 17, 2009) |
| YG1-110<br><br>M.W. = 415.48<br>1.35 mg submitted Sep. 05, 2008 | | 1.04<br>1.86<br>2.06<br>2.35<br>3.8<br>2.22 ± 0.901 (n = 5) | (Nov. 19, 2008)<br>(Jan. 08, 2009)<br>(Jan. 14, 2009) |

TABLE 1-continued

HLM008182 and analogues (Group I)

| Name Molecular Wt/ Structure | $IC_{50}$ (μM)* | Chymotrypsin-like Activity $IC_{50}$ (μM)-Inhibition at 30 μM | |
|---|---|---|---|
| YG1-113 <br><br> M.W. = 417.5 <br> 1.55 mg submitted on Sep. 05, 2008 <br> 1.75 mg resubmitted on Jan. 21, 2009 | | 1.74 <br> 5.3 <br> 5.02 <br> 7.0 <br> 8.7 <br> 2.75 <br> 6.4 <br> 5.27 ± 2.23 (n = 7) | (Nov. 19, 2008) <br> (Jan. 08, 2009) <br><br> (Jan. 14, 2009) <br><br> (Feb. 17, 2009) |
| YG1-117 <br><br> M.W. = 389.45 <br> 1.63 mg submitted on Sep. 05, 2008 | | 0.68 <br> 2.71 <br> 2.9 <br> 1.9 <br> 2.2 <br> 2.08 ± 0.784 (n = 5) | (Nov. 19, 2008) <br> (Jan. 08, 2009) <br><br> (Jan. 14, 2009) |
| YG1-148F5 <br><br> M.W. = 462.50 <br> 1.13 mg submitted on Oct. 21, 2008 | | 0.82 <br> 3.65 <br> 4.55 <br> 3.45 <br> 5.36 <br> 3.57 ± 1.53 (n = 5) | (Nov. 19, 2008) <br> (Jan. 08, 2009) <br><br> (Jan. 14, 2009) |

TABLE 1-continued

HLM008182 and analogues (Group I)

| Name Molecular Wt/ Structure | IC$_{50}$ (μM)* | Chymotrypsin-like Activity IC$_{50}$ (μM)-Inhibition at 30 μM | |
|---|---|---|---|
| YG1-152<br>M.W. = 465.54<br>1.39 mg submitted<br>on Oct. 21, 2008 | >100<br>(Oct. 19, 2010)<br>83 | 0.81<br>2.48<br>2.28<br>1.74<br>2.2<br>1.90 ± 0.597 (n = 5) | (Nov. 19, 2008)<br>(Jan. 08, 2009)<br><br>(Jan. 14, 2009) |
| YG1-153<br>M.W. = 429.92<br>1.29 mg submitted<br>on Oct. 21, 2008 | 8<br>(Oct. 19, 2010)<br>10 | 0.73<br>2.42<br>2.7<br>2.3<br>2.2<br>2.07 ± 0.691 (n = 5) | (Nov. 19, 2008)<br>(Jan. 08, 2009)<br><br>(Jan. 14, 2009) |
| YG1-155<br>M.W. = 457.54<br>1.22 mg submitted<br>on Oct. 21, 2008<br>1.23 mg<br>resubmitted on<br>Jan. 21, 2009 | | 1.12<br>4.6<br>5.32<br>7.7<br>7.1<br>1.04<br>1.5<br>4.05 ± 2.64 (n = 7) | (Nov. 19, 2008)<br>(Jan. 08, 2009)<br><br>(Jan. 14, 2009)<br><br>(Feb. 17, 2009) |

TABLE 1-continued

HLM008182 and analogues (Group I)

| Name Molecular Wt/ Structure | $IC_{50}$ (μM)* | Chymotrypsin-like Activity $IC_{50}$ (μM)-Inhibition at 30 μM | |
|---|---|---|---|
| YG1-158-1<br>M.W. = 417.49<br>1.68 mg submitted on Oct. 21, 2008<br>1.08 mg resubmitted on Jan. 21, 2009 | | 2.46<br>7.24<br>7.9<br>9.8<br>>10<br>1.24<br>1.81<br>5.08 ± 3.35 (n = 6) | (Nov. 19, 2008)<br>(Jan. 08, 2009)<br><br>(Jan. 14, 2009)<br><br>(Feb. 17, 2009) |
| YG1-158-2<br>M.W. = 402.47<br>1.29 mg submitted on Oct. 21, 2008 | | 1.34<br>4.38<br>3.85<br>2.1<br>2.09<br>2.75 ± 1.16 (n = 5) | (Nov. 19, 2008)<br>(Jan. 08, 2009)<br><br>(Jan. 14, 2009) |
| YG1-159-1<br>M.W. = 419.50<br>1.94 mg submitted on Oct. 21, 2008<br>1.48 mg resubmitted on Jan. 21, 2009 | 6.4<br>(Oct. 19, 2010)<br>6.4 | 2.11<br>4.32<br>6.45<br>6.6<br>6.55<br>1.54<br>2.18<br>4.25 ± 2.13 (n = 7) | (Nov. 19, 2008)<br>(Jan. 08, 2009)<br><br>(Jan. 14, 2009)<br><br>(Feb. 17, 2009) |

TABLE 1-continued

HLM008182 and analogues (Group I)

| Name Molecular Wt/ Structure | IC$_{50}$ (μM)* | Chymotrypsin-like Activity IC$_{50}$ (μM)-Inhibition at 30 μM | |
|---|---|---|---|
| YG1-159-2 [structure: 4-hydroxy-naphthalene with triazolylthio and thiophenesulfonamido substituents] M.W. = 404.49 1.54 mg submitted on Oct. 21, 2008 1.21 mg resubmitted on Jan. 21, 2009 | 4.8 (Oct. 19, 2010) 5.1 | 1.4 6.55 7.40 5.6 6.6 0.85 1.12 4.22 ± 2.73 (n = 7) | (Nov. 19, 2008) (Jan. 08, 2009) (Jan. 14, 2009) (Feb. 17, 2009) |
| HL4-098-2 [structure: hydroxynaphthalene with carboxymethylthio and dichlorothiophenesulfonamido substituents] M.W. = 464.36 1.19 mg submitted on Oct. 21, 2008 | 25 (Oct. 19, 2010) 17.4 | 1.05 2.4 2.14 2.09 2.67 2.07 ± 0.550 (n = 5) | (Nov. 19, 2008) (Jan. 08, 2009) (Jan. 14, 2009) |
| HL4-098-3 [structure: hydroxynaphthalene with methyl propanoate thioether and dichlorothiophenesulfonamido substituents] M.W. = 492.41 1.27 mg submitted on Oct. 21, 2008 | | 0.81 1.5 1.52 0.9 1.16 1.18 ± 0.295 (n = 5) | (Nov. 19, 2008) (Jan. 08, 2009) (Jan. 14, 2009) |

TABLE 1-continued

HLM008182 and analogues (Group I)

| Name Molecular Wt/ Structure | $IC_{50}$ (μM)* | Chymotrypsin-like Activity $IC_{50}$ (μM)-Inhibition at 30 μM | |
|---|---|---|---|
| YG1-168 | | 2.32 | (Jan. 08, 2009) |
| | | 2.44 | |
| | | 2.15 | (Jan. 14, 2009) |
| | | 1.84 | |
| | | 2.19 ± 0.226 (n = 4) | |
| M.W. = 527.61 1.25 mg submitted on Jan. 08, 2009 | | | |
| YG2-014 | | 4.0 | (Jan. 08, 2009) |
| | | 4.7 | |
| | | 4.2 | (Jan. 14, 2009) |
| | | >10 | |
| | | 4.3 ± 0.294 (n = 3) | |
| M.W. = 429.51 1.63 mg submitted on Jan. 08, 2009 | | | |
| YG2-034-1 | | >10 | (Jan. 08, 2009) |
| | | 3.44 | |
| | | 3.65 | (Jan. 14, 2009) |
| | | 4.15 | |
| | | 3.75 ± 0.298 (n = 3) | |
| M.W. = 423.89 1.56 mg submitted on Jan. 08, 2009 | | | |

TABLE 1-continued

HLM008182 and analogues (Group I)

| Name Molecular Wt/ Structure | IC$_{50}$ (μM)* | Chymotrypsin-like Activity IC$_{50}$ (μM)-Inhibition at 30 μM |
|---|---|---|
| YG2-034-2<br><br>M.W. = 439.50<br>1.27 mg submitted<br>on Jan. 08, 2009 | | >10 (Jan. 08, 2009)<br>4.0<br>5.9 (Jan. 14, 2009)<br>4.6<br>4.83 ± 0.793 (n = 3) |
| YG1-094-2<br><br>M.W. = 423.53<br>1.45 mg submitted<br>on Aug. 12, 2008 | | 2.67 (Sep. 01, 2008)<br>7.5 (Nov. 19, 2008)<br>9.65 (Jan. 08, 2009)<br>9.5<br>7.33 ± 2.82 (n = 4) |
| YG2-019<br><br>M.W. = 463.95<br>1.94 mg submitted<br>on Jan. 08, 2009<br>1.87 mg<br>resubmitted on<br>Jan. 21, 2009 | | 6.9 (Jan. 08, 2009)<br>7.6<br>>10 (Jan. 14, 2009)<br>>10<br>>10 (Feb. 17, 2009)<br>>10<br>7.25 ± 0.350 (n = 2) |
| YG2-024-1<br><br>M.W. = 437.92<br>2.59 mg submitted<br>on Jan. 08, 2009 | | 9.5 (Jan. 08, 2009)<br>>10<br>8.0 (Jan. 14, 2009)<br>8.2<br>8.57 ± 0.665 (n = 3) |

TABLE 1-continued

HLM008182 and analogues (Group I)

| Name Molecular Wt/ Structure | IC$_{50}$ (μM)* | Chymotrypsin-like Activity IC$_{50}$ (μM)-Inhibition at 30 μM | |
| --- | --- | --- | --- |
| YG2-024-2<br>M.W. = 453.53<br>2.54 mg submitted<br>on Jan. 08, 2009 | | 8.9<br>9.6<br>9.5<br>8.45<br>9.11 ± 0.467 (n = 4) | (Jan. 08, 2009)<br>(Jan. 14, 2009) |
| HL4-078-1<br>M.W. = 434.55<br>1.44 mg submitted<br>on Oct. 21, 2008 | | 4.7<br>9.65<br>9.56<br>8.5<br>>10<br>8.10 ± 2.02 (n = 4) | (Nov. 19, 2008)<br>(Jan. 08, 2009)<br>(Jan. 14, 2009) |
| HL4-078-3<br>M.W. = 446.56<br>1.04 mg submitted<br>on Oct. 21, 2008 | | 5.5<br>10<br>8.65<br>>10<br>>10<br>8.05 ± 1.09 (n = 3) | (Nov. 19, 2008)<br>(Jan. 08, 2009)<br>(Jan. 14, 2009) |

TABLE 1-continued

HLM008182 and analogues (Group I)

| Name Molecular Wt/ Structure | $IC_{50}$ (μM)* | Chymotrypsin-like Activity $IC_{50}$ (μM)-Inhibition at 30 μM |
|---|---|---|
| HL4-100-3<br><br>[Structure: 4-hydroxy-naphthalene with thioether linked to propanamide N-cyclopropyl group, and thiophene-2-sulfonamide at the 1-position]<br><br>M.W. = 448.57<br>1.52 mg submitted<br>on Oct. 21, 2008 | 8.6 (Nov. 19, 2008)<br>6 (Jan. 08, 2009)<br>>10<br>7.3 ± 1.30 (n = 2) | |
| YG1-004<br><br>[Structure: 4-hydroxy-naphthalen-1-yl thiophene-2-sulfonamide]<br><br>M.W. = 305.37<br>2.32 mg submitted<br>on Jun. 19, 2008 | >30 (M-1096)<br>(M-1096)<br>>100 (M-1098)<br>(M-1098)<br>35 (M-1099)<br>(M-1099)<br><br>(M-1098)<br>(M-1099)<br>(Jun. 25, 2008) | −65%<br><br>14%<br><br>49%<br><br>Inhib at 100 μM<br>44%<br>67% |
| YG1-012<br><br>[Structure: 3-chloro-4-hydroxy-naphthalen-1-yl thiophene-2-sulfonamide]<br><br>M.W. = 339.82<br>3.24 mg submitted<br>on Jun. 19, 2008 | >30 (M-1096)<br>(M-1096)<br>45 (M-1098)<br>(M-1098)<br>36 (M-1099)<br>(M-1099)<br><br>(M-1098)<br>(M-1099)<br>(Jun. 25, 2008) | 33%<br><br>41%<br><br>45%<br><br>Inhib at 100 μM<br>82%<br>97% |

TABLE 1-continued

HLM008182 and analogues (Group I)

| Name Molecular Wt/ Structure | IC$_{50}$ (μM)* | Chymotrypsin-like Activity IC$_{50}$ (μM)-Inhibition at 30 μM |
|---|---|---|
| YG1-033 [structure] M.W. = 431.27 2.20 mg submitted on Jun. 19, 2008 | 26 (M-1096) (M-1096) >100 (M-1098) (M-1098) 28 (M-1099) (M-1099) (M-1098) (M-1099) (Jun. 25, 2008) | 70% 19% 67% Inhib at 100 μM 37% 93% |
| YG1-034 [structure] M.W. = 384.27 3.26 mg submitted on Jun. 19, 2008 | >30 (M-1096) (M-1096) >100 (M-1098) (M-1098) 28 (M-1099) (M-1099) (M-1098) (M-1099) (Jun. 25, 2008) | 3% 23% 56% Inhib at 100 μM 21% 95% |
| YG1-059 [structure] M.W. = 276.31 3.20 mg submitted on Jun. 19, 2008 | >30 (M-1096) (M-1096) >100 (M-1098) >100 (M-1099) (M-1099) (M-1096) (M-1099) (Jun. 25, 2008) | 49% ND Inhib at 100 μM 6% 33% |
| YG1-017 [structure] M.W. = 394.46 3.15 mg submitted on Jun. 19, 2008 | >30 (M-1096) (M-1096) 48 (M-1098) (M-1098) >100 (M-1099) (M-1099) (M-1096) (M-1099) (Jun. 25, 2008) | −17% 47% 22% Inhib at 100 μM 57% 36% |

TABLE 1-continued

HLM008182 and analogues (Group I)

| Name<br>Molecular Wt/<br>Structure | IC$_{50}$ (μM)* | Chymotrypsin-like Activity<br>IC$_{50}$ (μM)-Inhibition at 30 μM |
|---|---|---|
| YG1-116 | 7.4<br>>10<br>>10 | (Nov. 19, 2008)<br>(Jan. 08, 2009) |
| M.W. = 409.5<br>1.54 mg submitted<br>on Sep. 05, 2008 | | |
| YG1-133 | 8.2<br>>10<br>>10 | (Nov. 19, 2008)<br>(Jan. 08, 2009) |
| M.W. = 455.53<br>1.84 mg submitted<br>on Oct. 21, 2008 | | |
| HL4-078-2 | 8.1<br>>10<br>>10 | (Nov. 19, 2008)<br>(Jan. 08, 2009) |
| M.W. = 420..52<br>1.01 mg submitted<br>on Oct. 21, 2008 | | |
| YG1-122 | >10<br>>10<br>>10 | (Nov. 19, 2008)<br>(Jan. 08, 2009) |
| M.W. = 347.41<br>1.26 mg submitted<br>on Sep. 05, 2008 | | |

TABLE 1-continued

HLM008182 and analogues (Group I)

| Name<br>Molecular Wt/<br>Structure | IC$_{50}$ (μM)* | Chymotrypsin-like Activity<br>IC$_{50}$ (μM)-Inhibition at 30 μM |
|---|---|---|
| YG1-124<br><br>M.W. = 349.42<br>1.27 mg submitted<br>on Sep. 05, 2008 | >10<br>>10<br>>10 | (Nov. 19, 2008)<br>(Jan. 08, 2009) |
| YG1-125<br><br>M.W. = 346.42<br>1.44 mg submitted<br>on Sep. 05, 2008 | >10<br>>10<br>>10 | (Nov. 19, 2008)<br>(Jan. 08, 2009) |
| YG1-129<br><br>M.W. = 388.46<br>1.28 mg submitted<br>on Sep. 05, 2008 | >10<br>>10<br>>10 | (Nov. 19, 2008)<br>(Jan. 08, 2009) |
| S.M. of YL2-013<br><br>M.W. = 174.15<br>4.48 mg submitted<br>on Sep. 05, 2008 | >10<br>>10<br>>10 | (Nov. 19, 2008)<br>(Jan. 08, 2009) |

TABLE 1-continued

HLM008182 and analogues (Group I)

| Name<br>Molecular Wt/<br>Structure | IC$_{50}$ (μM)* | Chymotrypsin-like Activity<br>IC$_{50}$ (μM)-Inhibition at 30 μM |
|---|---|---|
| YL2-013<br>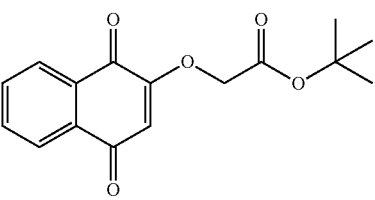 [SMILES: CC(C)(C)OC(=O)COC1=CC(=O)c2ccccc2C1=O]<br>M.W. = 288.30<br>1.23 mg submitted<br>on Sep. 05, 2008 | >10<br>>10<br>>10 | (Nov. 19, 2008)<br>(Jan. 08, 2009) |
| YL2-015 4th spot<br>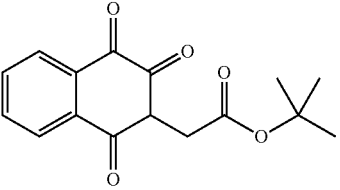 [SMILES: CC(C)(C)OC(=O)CC1C(=O)C(=O)c2ccccc2C1=O]<br>M.W. = 288.30<br>(proposed<br>structure)<br>1.13 mg submitted<br>on Sep. 05, 2008 | >10<br>>10<br>>10 | (Nov. 19, 2008)<br>(Jan. 08, 2009) |
| YL2-023<br>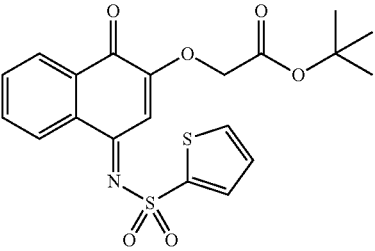 [SMILES: CC(C)(C)OC(=O)COC1=C/C(=N\S(=O)(=O)c2cccs2)c2ccccc2C1=O]<br>M.W. = 433.50<br>1.99 mg submitted<br>on Sep. 05, 2008 | >10<br>>10<br>>10 | (Nov. 19, 2008)<br>(Jan. 08, 2009) |
| YL2-025<br>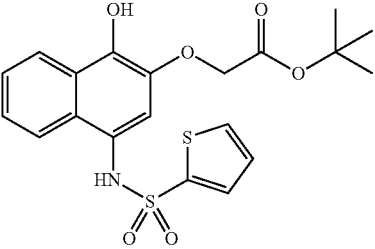 [SMILES: CC(C)(C)OC(=O)COc1cc(NS(=O)(=O)c2cccs2)c2ccccc2c1O]<br>M.W. = 435.51<br>0.75 mg submitted<br>on Sep. 05, 2008 | >10<br>>10<br>>10 | (Nov. 19, 2008)<br>(Jan. 08, 2009) |

TABLE 1-continued
HLM008182 and analogues (Group I)
| Name Molecular Wt/ Structure | IC$_{50}$ (μM)* | Chymotrypsin-like Activity IC$_{50}$ (μM)-Inhibition at 30 μM |
|---|---|---|
| YL2-030<br>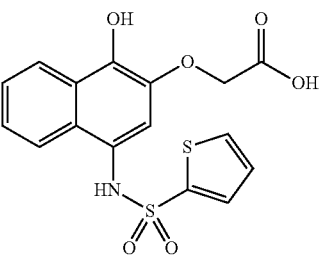<br>M.W. = 379.41<br>1.18 mg submitted on Sep. 05, 2008 | >10<br>>10<br>>10 | (Nov. 19, 2008)<br>(Jan. 08, 2009) |
| YG1-130<br>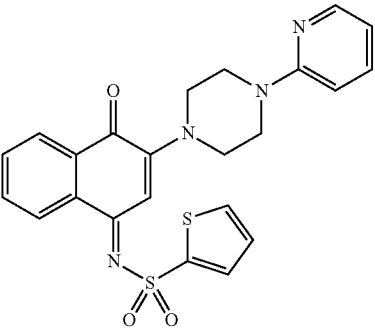 [SMILES: O=C1C(N2CCN(c3ccccn3)CC2)=C/C(=N\S(=O)(=O)c2cccs2)c2ccccc21]<br>M.W. = 464.56<br>1.47 mg submitted on Oct. 21, 2008 | >10<br>>10<br>>10 | (Nov. 19, 2008)<br>(Jan. 08, 2009) |
| YG1-134<br>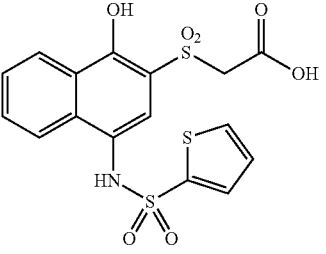 [SMILES: O=C(O)CS(=O)(=O)c1cc(NS(=O)(=O)c2cccs2)c2ccccc2c1O]<br>M.W. = 427.47<br>2.11 mg submitted on Oct. 21, 2008 | >10<br>>10<br>>10 | (Nov. 19, 2008)<br>(Jan. 08, 2009) |

TABLE 1-continued
HLM008182 and analogues (Group I)
| Name Molecular Wt/ Structure | IC$_{50}$ (μM)* | Chymotrypsin-like Activity IC$_{50}$ (μM)-Inhibition at 30 μM | |
|---|---|---|---|
YG1-174
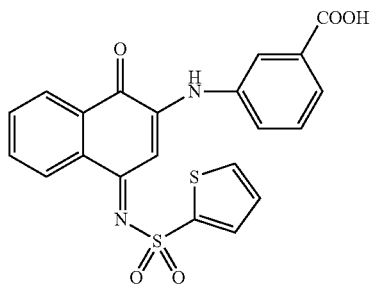 [SMILES: O=C(O)c1cccc(NC2=C/C(=N\S(=O)(=O)c3cccs3)c3ccccc3C2=O)c1]
M.W. = 438.48
1.25 mg submitted
on Jan. 08, 2009
>10
>10
(Jan. 08, 2009)
YG2-011
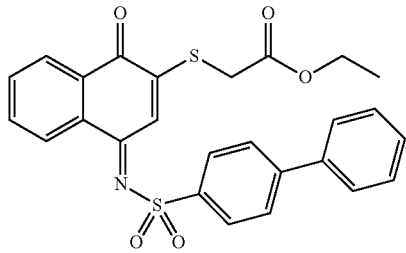 [SMILES: CCOC(=O)CSC1=C/C(=N\S(=O)(=O)c2ccc(-c3ccccc3)cc2)c2ccccc2C1=O]
M.W. = 491.58
2.70 mg submitted
on Jan. 08, 2009
>10
>10
(Jan. 08, 2009)
HL4-100-1
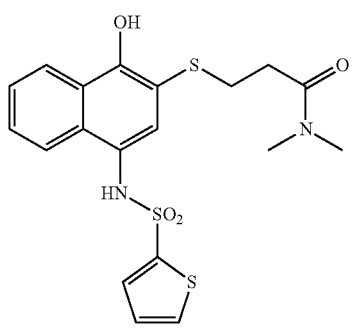 [SMILES: CN(C)C(=O)CCSc1cc(NS(=O)(=O)c2cccs2)c2ccccc2c1O]
M.W. = 436.56
1.30 mg submitted
on Oct. 21, 2008
>10
>10
>10
(Nov. 19, 2008)
(Jan. 08, 2009)

TABLE 1-continued

HLM008182 and analogues (Group I)

| Name<br>Molecular Wt/<br>Structure | $IC_{50}$ (μM)* | Chymotrypsin-like Activity<br>$IC_{50}$ (μM)-Inhibition at 30 μM |
|---|---|---|
| HL4-100-2<br><br>M.W. = 422.54<br>0.90 mg submitted<br>on Oct. 21, 2008 | >10<br>>10<br>>10 | (Nov. 19, 2008)<br>(Jan. 08, 2009) |
| YG2-080<br><br>M.W. = 419.51<br>1.60 mg submitted<br>on Mar. 31, 2009 | >10<br>>10 | (Apr. 07, 2009) |
| YG2-083<br><br>M.W. = 363.41<br>2.51 mg resubmitted<br>on Mar. 31, 2009 | >10<br>>10 | (Apr. 07, 2009) |
| YG2-086-1<br><br>M.W. = 363.47<br>1.05 mg submitted<br>on Mar. 31, 2009 | 9.4<br>9.85 | (Apr. 07, 2009) |

TABLE 1-continued

HLM008182 and analogues (Group I)

| Name Molecular Wt/ Structure | $IC_{50}$ (μM)* | Chymotrypsin-like Activity $IC_{50}$ (μM)-Inhibition at 30 μM | |
|---|---|---|---|
| YG2-087-1 | >10 >10 | | (Apr. 07, 2009) |
| M.W. = 365.49 1.20 mg submitted on Mar. 31, 2009 | | | |
| YG1-087-2 | >10 >10 | | (Apr. 07, 2009) |
| M.W. = 381.49 1.14 mg submitted on Mar. 31, 2009 | | | |
| YG2-094 | >10 >10 | | (Apr. 07, 2009) |
| M.W. = 391.46 2.24 mg submitted on Mar. 31, 2009 | | | |
| YG3-005 | >10 | | |
| M.W. = 233.29 0.96 mg submitted on Aug. 19, 2009 | | | |

TABLE 1-continued

HLM008182 and analogues (Group I)

| Name Molecular Wt/ Structure | IC$_{50}$ (μM)* | Chymotrypsin-like Activity IC$_{50}$ (μM)-Inhibition at 30 μM |
|---|---|---|
| YG3-007 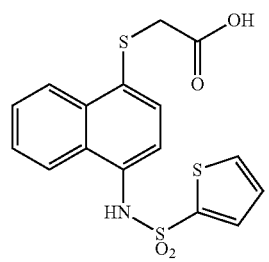 [SMILES: O=C(O)CSc1ccc(NS(=O)(=O)c2cccs2)c2ccccc12] M.W. = 379.47 1.18 mg submitted on Aug. 19, 2009 | >10 | |

* In Cell culture against CT-L

Intrmolecular cyclization derivative of HLM-008182

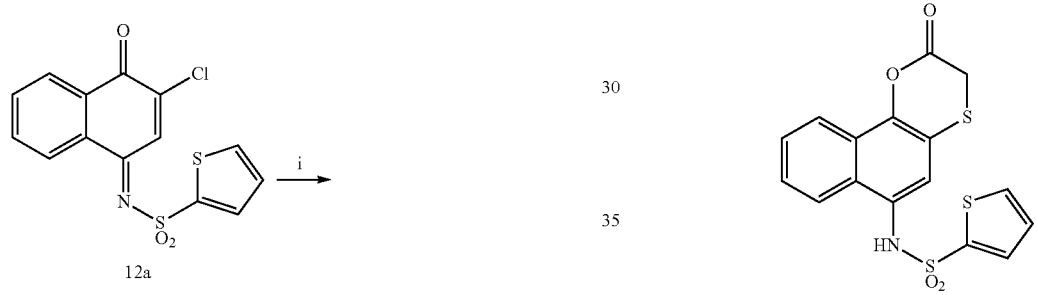

Conditions and reagents: i) (a) HSCH$_2$COOH, pyridine, THF, r.t.; (b) Na$_2$S$_2$O$_4$, H$_2$O, EtOAc; ii) EDC, CH$_3$CN, r.t.

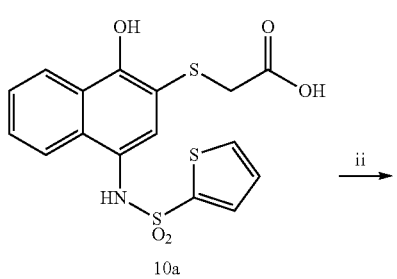

(23)

N-(2-oxo-2,3-dihydronaphtho[1,2-b][1,4]oxathiin-6-yl)thiophene-2-sulfonamide (23): 103.3 mg 12a was dissolved in 3 ml THF, to which was added 0.612 ml THF solution containing 0.5 M pyridine followed by 0.612 ml THF solution containing 0.5 M 2-mercaptoglycolic acid. The mixture was stirred at room temperature for 30 min and the organic solvent was removed via rotavap. The residue was partitioned between 40 ml ethyl acetate and 10 ml 0.5 M NaHSO$_4$. The organic phase was separated and shaken with an aqueous solution containing 5 eq. Na$_2$S$_2$O$_4$ until a colorless solution was obtained. The ethyl acetate layer was separated and washed with water and brine. Dried over Na$_2$SO$_4$, the organic phase was concentrated to dryness affording 150 mg crude product 10a. The crude product was suspended in 6 ml acetonitrile, to which was added 58.5 mg EDC. The mixture was stirred at room temperature for 1 hour and concentrated. The crude product was purified via flash chromatography (10 g silica gel, Hex/EtOAc) affording a slightly yellow solid 101.4 mg (87.8%, 2 steps).

$^1$H NMR (400 MHz, CDCl$_3$) δ 8.13 (d, J=8.5 Hz, 1H), 7.62 (d, J=8.5 Hz, 1H), 7.52-7.47 (m, 1H), 7.46 (dd, J=5.0, 1.3 Hz, 1H), 7.43-7.36 (m, 3H), 6.89 (dd, J=5.0, 3.8 Hz, 1H), 6.75 (br s, 1H), 3.50 (s, 2H).

LCMS (ESI+ve) m/z: 395 (M+NH$_4$)$^+$; HRMS (ESI+ve) m/z calculated for C$_{16}$H$_{12}$NO$_4$S$_3$ (M+H)$^+$377.9923, found 377.9916.

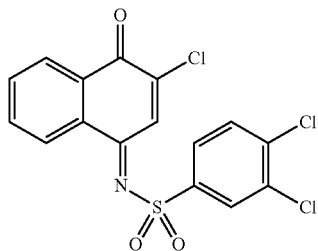 [SMILES: O=C1C(Cl)=C/C(=N\S(=O)(=O)c2ccc(Cl)c(Cl)c2)c2ccccc21]

(12g)

(E)-3,4-dichloro-N-(3-chloro-4-oxonaphthalen-1(4H)-ylidene)benzenesulfonamide (12g) was prepared according to the procedure for 12a except that the reaction was carried out with 3,4-dichlorobenzenesulfonamide in THF for 30 min. 621.7 mg (77.6%) title compound was obtained as a yellow solid.

$^1$HNMR (400 MHz, CDCl$_3$) δ 8.57 (s, 1H), 8.21 (dd, J=7.2, 1.6 Hz, 1H), 8.16 (d, J=2.4 Hz, 1H), 8.12 (dd, J=6.8, 1.6 Hz, 1H), 7.90 (dd, J=8.4, 2.8 Hz, 1H), 7.76 (dt, J=7.6, 1.2 Hz, 1H), 7.72-7.68 (m, 2H).

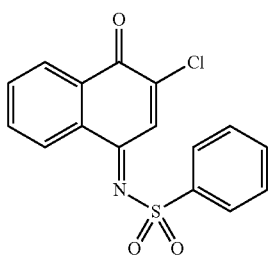 [SMILES: O=C1C(Cl)=C/C(=N\S(=O)(=O)c2ccccc2)c2ccccc21]

(12h)

(E)-N-(3-chloro-4-oxonaphthalen-1(4H)-ylidene)benzenesulfonamide (12h) was prepared according to the procedure for 12a except that the reaction was carried out with benzenesulfonamide in THF for 30 min. 508.1 mg (76.6%) title compound was obtained as a yellow solid.

$^1$H NMR (400 MHz, CDCl$_3$) δ 8.67 (s, 1H), 8.20 (dd, J=7.6, 0.8 Hz, 1H), 8.15 (dd, J=7.2, 1.2 Hz, 1H), 8.08 (d, J=7.6 Hz, 2H), 7.74 (dt, J=7.6, 1.2 Hz, 1H), 7.71-7.66 (m, 2H), 7.62 (t, J=7.5 Hz, 2H).

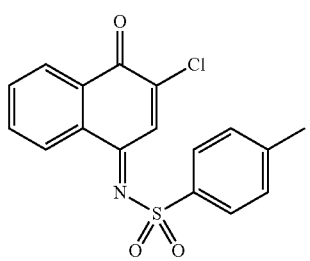 [SMILES: Cc1ccc(S(=O)(=O)/N=C2\C=C(Cl)C(=O)c3ccccc32)cc1]

(12i)

(E)-N-(3-chloro-4-oxonaphthalen-1(4H)-ylidene)-4-methylbenzenesulfonamide (12i) was prepared according to the procedure for 12a except that the reaction was carried out with p-toluenesulfonamide in THF for 30 min. 553.7 mg (80.1%) title compound was obtained as a yellow solid.

$^1$HNMR (400 MHz, CDCl$_3$) δ 8.69 (s, 1H), 8.20 (dd, J=7.6, 1.2 Hz, 1H), 8.15 (dd, J=7.6, 1.2 Hz, 1H), 7.96 (d, J=8.3 Hz, 2H), 7.73 (dt, J=7.2, 1.2 Hz, 1H), 7.67 (dt, J=7.6, 1.2 Hz, 1H), 7.40 (d, J=8.5 Hz, 2H), 2.48 (s, 3H).

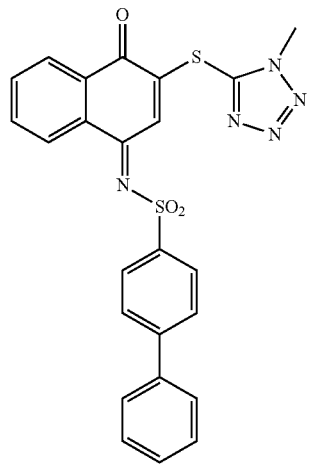 [SMILES: Cn1nnnc1SC1=C/C(=N\S(=O)(=O)c2ccc(-c3ccccc3)cc2)c2ccccc2C1=O]

(13x)

(E)-N-(3-(1-methyl-1H-tetrazol-5-ylthio)-4-oxonaphthalen-1(4H)-ylidene)biphenyl-4-sulfonamide (13x): 81.6 mg 12b was dissolved in 2 ml THF. 1 ml THF solution containing 1 eq. 1-methyl-tetrazole-5-thiol and 1 eq. pyridine was added. The mixture was shaken for 30 min. The organic solvent was removed by V-10 (biotage). The residue was suspended in 10 ml water and sonicated thoroughly. The insoluble was filtered and washed with water. The solid was dried over air affording 96.5 mg (99.0%) title compound 13x.

$^1$H NMR (400 MHz, CDCl$_3$) δ 8.22 (m, 1H), 8.15 (m, 1H), 8.07 (s, 1H), 8.05 (d, J=8.4 Hz, 2H), 7.77 (d, J=6.4 Hz, 2H), 7.74-7.71 (m, 2H), 7.63-7.61 (m, 2H), 7.51-7.41 (m, 3H), 4.23 (s, 3H).

LCMS (ES+) 488 (M+H)$^+$, 505 (M+NH$_4$)$^+$, 510 (M+Na)$^+$; HRMS (ES+) m/z calculated for C$_{24}$H$_{18}$N$_5$O$_3$S$_2$ (M+H)$^+$ 488.0846, found 488.0841.

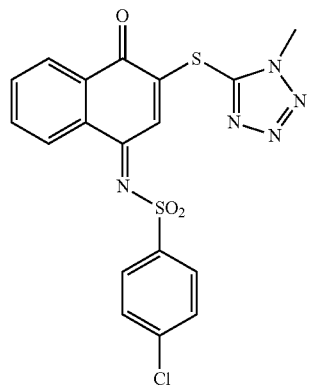 [SMILES: Cn1nnnc1SC1=C/C(=N\S(=O)(=O)c2ccc(Cl)cc2)c2ccccc2C1=O]

(13y)

(E)-4-chloro-N-(3-(1-methyl-1H-tetrazol-5-ylthio)-4-oxonaphthalen-1(4H)-ylidene) benzenesulfonamide (13y) was prepared according to the procedure for 13x except using 12e, affording 88.7 mg (99.4%) title compound as a yellow solid.

$^1$H NMR (400 MHz, CDCl$_3$) δ 8.16-8.14 (m, 2H), 8.04 (s, 1H), 7.93 (d, J=6.8 Hz, 2H), 7.74 (dt, J=6.0, 1.6 Hz, 1H), 7.71 (dt, J=5.2, 1.2 Hz 1H), 7.56 (d, J=6.8 Hz 2H), 4.22 (s, 3H).

LCMS (ES+) 446 (M+H)$^+$, 463 (M+NH$_4$)$^+$, 468 (M+Na)$^+$; HRMS (ES+) m/z calculated for C$_{18}$H$_{13}$ClN$_5$O$_3$S$_2$ (M+H)$^+$ 466.0143, found 466.0141.

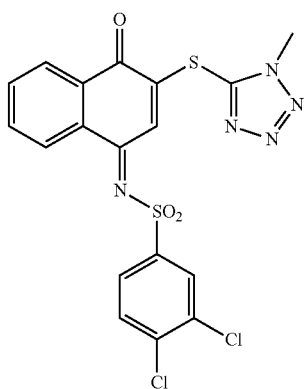 [SMILES: Cn1nnnc1SC1=C/C(=N\S(=O)(=O)c2ccc(Cl)c(Cl)c2)c2ccccc2C1=O]
(13z)

(E)-3,4-dichloro-N-(3-(1-methyl-1H-tetrazol-5-ylthio)-4-oxonaphthalen-1(4H)-ylidene)benzenesulfonamide (13z) was prepared according to the procedure for 13x except using 12g, affording 94.7 mg (98.5%) title compound as a yellow solid.

$^1$H NMR (400 MHz, CDCl$_3$) δ 8.17-8.13 (m, 2H), 8.10 (d, J=2.0 Hz, 1H), 8.04 (s, 1H), 7.83 (dd, J=8.4, 2.0 Hz, 1H), 7.76 (dt, J=7.2, 1.6 Hz, 1H), 7.73 (dt, J=5.6, 2.0 Hz, 1H), 7.67 (d, J=8.4 Hz, 1H), 4.22 (s, 3H).

LCMS (ES+) 480 (M+H)$^+$, 497 (M+NH$_4$)$^+$, 502 (M+Na)$^+$; HRMS (ES+) m/z calculated for C$_{18}$H$_{12}$Cl$_2$N$_5$O$_3$S$_2$ (M+H)$^+$ 479.9753, found 479.9746.

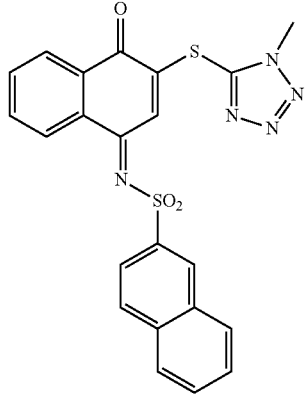
(13ab)

(E)-N-(3-(1-methyl-1H-tetrazol-5-ylthio)-4-oxonaphthalen-1(4H)-ylidene)naphthalene-2-sulfonamide (13ab) was prepared according to the procedure for 13x except using 12f, affording 85.5 mg (92.6%) title compound as a yellow solid.

$^1$H NMR (400 MHz, CDCl$_3$) δ 8.55 (s, 1H), 8.18 (dd, J=5.2, 2.0 Hz, 1H), 8.13 (dd, J=4.8, 2.0 Hz, 1H), 8.12 (s, 1H), 8.07 (apparent d, J=7.6 Hz, 1H), 8.02 (d, J=8.8 Hz, 1H), 7.96 (d, J=2.0 Hz, 1H) 7.93 (d, J=7.6 Hz, 1H), 7.74-7.62 (m, 4H), 4.24 (s, 3H).

LCMS (ES+) 462 (M+H)$^+$, 479 (M+NH$_4$)$^+$, 484 (M+Na)$^+$; HRMS (ES+) m/z calculated for C$_{22}$H$_{16}$N$_5$O$_3$S$_2$ (M+H)$^+$ 462.0689, found 462.0681.

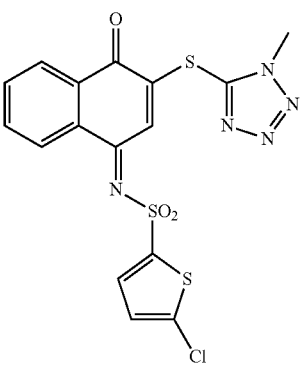 [SMILES: Cn1nnnc1SC1=C/C(=N\S(=O)(=O)c2ccc(Cl)s2)c2ccccc2C1=O]
(13aa)

(E)-5-chloro-N-(3-(1-methyl-1H-tetrazol-5-ylthio)-4-oxonaphthalen-1(4H)-ylidene)thiophene-2-sulfonamide (13aa) was prepared according to the procedure for 13x except using 12d, affording 77.1 mg (85.3%) title compound as a yellow solid.

$^1$H NMR (400 MHz, CDCl$_3$) δ 8.24-8.22 (m, 1H), 8.17-8.15 (m, 1H), 8.00 (s, 1H), 7.77-7.53 (m, 2H), 7.58 (d, J=4.0 Hz, 1H), 6.98 (d, J=4.4 Hz, 1H), 4.20 (s, 3H).

LCMS (ES+) 452 (M+H)$^+$, 469 (M+NH$_4$)$^+$, 474 (M+Na)$^+$; HRMS (ES+) m/z calculated for C$_{16}$H$_{11}$ClN$_5$O$_3$S$_2$ (M+H)$^+$ 451.9707, found 451.9698.

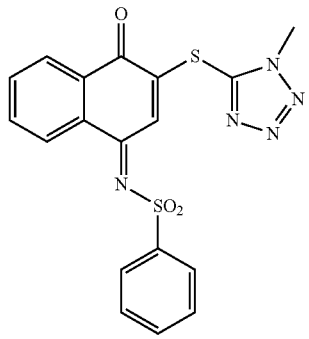 [SMILES: Cn1nnnc1SC1=C/C(=N\S(=O)(=O)c2ccccc2)c2ccccc2C1=O]
(13ac)

(E)-N-(3-(1-methyl-1H-tetrazol-5-ylthio)-4-oxonaphthalen-1(4H)-ylidene) benzenesulfonamide (13ac) was prepared according to the procedure for 13x except using 12h, affording 77.1 mg (93.7%) title compound as a yellow solid.

$^1$H NMR (400 MHz, CDCl$_3$) δ 8.19-8.13 (m, 2H), 8.03 (s, 1H), 7.97 (apparent d, J=5.6 Hz, 2H), 7.75-7.64 (m, 3H), 7.60-7.56 (m, 2H), 4.22 (s, 3H).

LCMS (ES+) 412 (M+H)$^+$, 429 (M+NH$_4$)$^+$, 434 (M+Na)$^+$, 823 (2M+H)$^+$, 840 (2M+NH$_4$)$^+$, 845 (2M+Na)$^+$; HRMS (ES+) m/z calculated for C$_{18}$H$_{14}$N$_5$O$_3$S$_2$ (M+H)$^+$412.0533, found 412.0537.

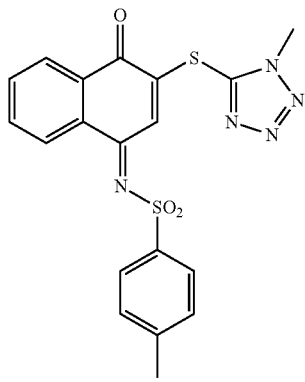 [SMILES: Cc1ccc(S(=O)(=O)/N=C2\C=C(Sc3nnnn3C)C(=O)c3ccccc32)cc1]

(13ad)

(E)-4-methyl-N-(3-(1-methyl-1H-tetrazol-5-ylthio)-4-oxonaphthalen-1(4H)-ylidene)benzenesulfonamide (13ad) was prepared according to the procedure for 13x except using 12i, affording 81.8 mg (96.1%) title compound as a yellow solid.

$^1$H NMR (400 MHz, CDCl$_3$) δ 8.18 (dd, J=6.8, 2.4 Hz, 1H), 8.13 (dd, J=6.0, 2.0 Hz, 1H), 8.02 (s, 1H), 7.85 (d, J=6.8 Hz, 2H), 7.72 (dt, J=7.6, 2.0 Hz, 1H), 7.69 (dt, J=7.6, 2.0 Hz, 1H), 7.37 (d, J=8.40 Hz, 2H), 4.22 (s, 3H), 2.45 (s, 3H).

LCMS (ES+) 426 (M+H)$^+$, 443 (M+NH$_4$)$^+$, 448 (M+Na)$^+$, 851 (2M+H)$^+$, 868 (2M+NH$_4$)$^+$, 873 (2M+Na)$^+$; HRMS (ES+) m/z calculated for C$_{19}$H$_{16}$N$_5$O$_3$S$_2$ (M+H)$^+$ 426.0689, found 426.0686.

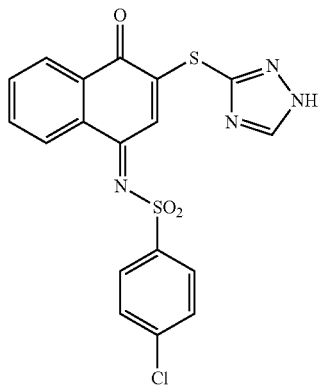

(13af)

(E)-N-(3-(1H-1,2,4-triazol-3-ylthio)-4-oxonaphthalen-1(4H)-ylidene)-4-chlorobenzenesulfonamide (13af) was prepared according to the procedure for 13x except using 12e and 3-mercapto-1,2,4-triazole, affording 43.8 mg (57.4%) title compound as a yellow solid.

$^1$H NMR (400 MHz, CD$_3$CN) δ 12.71 (br s, 1H), 8.64 (s, 1H), 8.14 (dd, J=6.1, 1.5 Hz, 1H), 8.12 (dd, J=6.3, 1.6 Hz, 1H), 7.94 (d, J=8.8 Hz, 2H), 7.81 (td, J=6.3, 1.7 Hz, 1H), 7.80 (s, 1H), 7.77 (td, J=6.3, 1.7 Hz, 1H), 7.65 (d, J=8.8 Hz, 2H).

LCMS (ESI+ve) m/z: 431 (M+H)$^+$, 453 (M+Na)$^+$, 861 (2M+H)$^+$, 883 (2M+Na)$^+$; HRMS (ESI+ve) m/z calculated for C$_{18}$H$_{12}$ClN$_4$O$_3$S$_2$ (M+H)$^+$ 431.0034, found 431.0028.

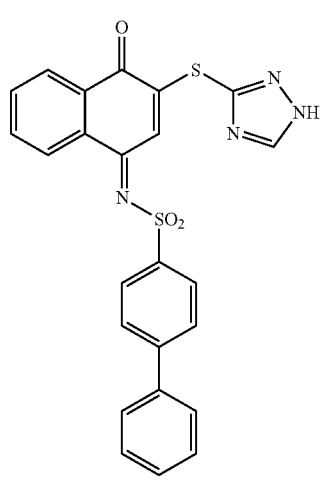 [SMILES: O=C1C(Sc2nc[nH]n2)=C/C(=N\S(=O)(=O)c2ccc(-c3ccccc3)cc2)c2ccccc21]

(13ae)

(E)-N-(3-(1H-1,2,4-triazol-3-ylthio)-4-oxonaphthalen-1(4H)-ylidene)biphenyl-4-sulfonamide (13ae) was prepared according to the procedure for 13x except using 12b and 3-mercapto-1,2,4-triazole, affording 53.6 mg (56.7%) title compound as a yellow solid.

$^1$H NMR (400 MHz, CD$_3$CN) δ 12.71 (br s, 1H), 8.66 (br s, 1H), 8.18-8.11 (m, 2H), 8.02 (d, J=8.7 Hz, 2H), 7.89 (d, J=8.7 Hz, 2H), 7.86 (s, 1H), 7.83-7.76 (m, 2H), 7.74 (dd, J=8.3, 1.3 Hz, 2H), 7.54 (t, J=7.3 Hz, 2H), 7.48 (d, J=7.3 Hz, 1H).

LCMS (ESI+ve) m/z: 473 (M+H)$^+$, 495 (M+Na)$^+$; HRMS (ESI+ve) m/z calculated for C$_{24}$H$_{17}$N$_4$O$_3$S$_2$ (M+H)$^+$ 473.0737, found 473.0732.

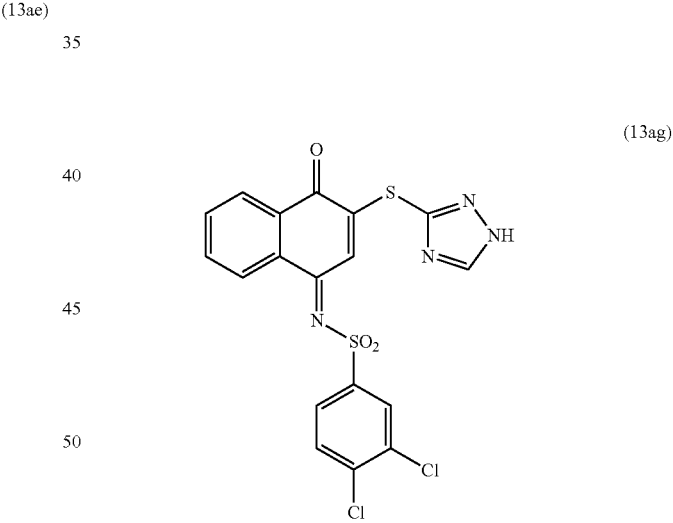

(13ag)

(E)-N-(3-(1H-1,2,4-triazol-3-ylthio)-4-oxonaphthalen-1(4H)-ylidene)-3,4-dichlorobenzenesulfonamide (13ag) was prepared according to the procedure for 13x except using 12g and 3-mercapto-1,2,4-triazole, affording 27.8 mg (29.9%) title compound as a yellow solid.

$^1$H NMR (400 MHz, CD$_3$CN) δ 12.72 (br s, 1H), 8.63 (s, 1H), 8.16-8.12 (m, 2H), 8.11 (d, J=2.1 Hz, 1H), 7.87 (dd, J=8.5, 2.1 Hz, 1H), 7.83-7.75 (m, 2H), 7.80 (s, 1H), 7.84 (d, J=8.5 Hz, 1H).

LCMS (ESI+ve) m/z: 465 (M+H)$^+$, 487 (M+Na)$^+$; HRMS (ESI+ve) m/z calculated for C$_{18}$H$_{11}$Cl$_2$N$_4$O$_3$S$_2$ (M+H)$^+$ 464.9644, found 464.9641.

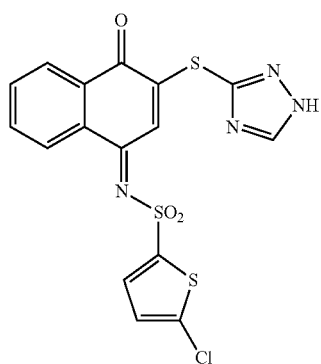

(13ah)

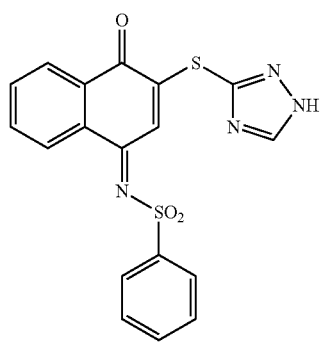

(13aj)

(E)-N-(3-(1H-1,2,4-triazol-3-ylthio)-4-oxonaphthalen-1 (4H)-ylidene)-5-chlorothiophene-2-sulfonamide (13ah) was prepared according to the procedure for 13x except using 12d and 3-mercapto-1,2,4-triazole, affording 69.2 mg (79.2%) title compound as a yellow solid.

$^1$H NMR (400 MHz, CD$_3$CN) δ 12.7 (br s, 1H), 8.62 (s, 1H), 8.20-8.17 (m, 1H), 8.16-8.12 (m, 1H), 7.85-7.78 (m, 2H), 7.77 (s, 1H), 7.58 (d, J=4.1 Hz, 1H), 7.14 (d, J=4.1 Hz, 1H).

LCMS (ESI+ve) m/z: 437 (M+H)$^+$, 459 (M+Na)$^+$, 875 (2M+H)$^+$, 897, (2M+Na)$^+$; HRMS (ESI+ve) m/z calculated for C$_{16}$H$_{10}$ClN$_4$O$_3$S$_3$ (M+H)$^+$ 436.9598, found 436.9592.

(E)-N-(3-(1H-1,2,4-triazol-3-ylthio)-4-oxonaphthalen-1 (4H)-ylidene)benzenesulfonamide (13aj) was prepared according to the procedure for 13x except using 12h and 3-mercapto-1,2,4-triazole, affording 52.9 mg (66.7%) title compound as a yellow solid.

$^1$H NMR (400 MHz, CD$_3$CN) δ 12.70 (br s, 1H), 8.64 (s, 1H), 8.14 (dd, J=4.6, 1.8 Hz, 1H), 8.12 (dd, J=4.6, 2.0 Hz, 1H), 7.96 (d, J=7.1 Hz, 2H), 7.83 (s, 1H), 7.79 (td, J=5.5, 1.7 Hz, 1H), 7.76 (td, J=5.5, 1.7 Hz, 1H) 7.73 (t, J=7.5 Hz, 1H), 7.64 (t, J=7.6 Hz, 2H).

LCMS (ESI+ve) m/z: 397 (M+H)$^+$, 419 (M+Na)$^+$, 793 (2M+H)$^+$, 815 (2M+Na)$^+$; HRMS (ESI+ve) m/z calculated for C$_{18}$H$_{13}$N$_4$O$_3$S$_2$ (M+H)$^+$ 397.0424, found 397.0426.

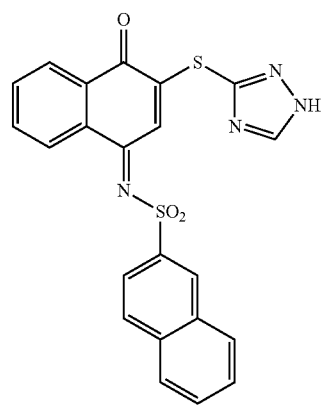

(13ai)

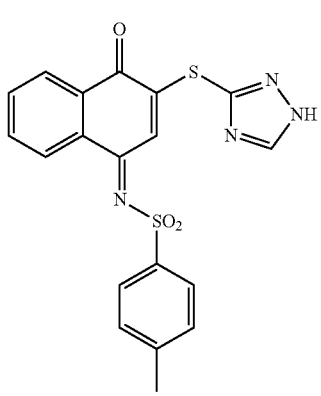

(13ak)

(E)-N-(3-(1H-1,2,4-triazol-3-ylthio)-4-oxonaphthalen-1 (4H)-ylidene)naphthalene-2-sulfonamide (13ai) was prepared according to the procedure for 13x except using 12f and 3-mercapto-1,2,4-triazole, affording 52.2 mg (58.5%) title compound as a yellow solid.

$^1$H NMR (400 MHz, CD$_3$CN) δ 12.73 (br s, 1H), 8.67 (br s, 1H), 8.57 (apparent d, J=1.7 Hz, 1H), 8.17-8.11 (m, 4H), 8.05 (apparent d, J=8.1 Hz, 1H), 7.96 (dd, J=8.8, 1.9 Hz, 1H), 7.91 (s, 1H), 7.81-7.69 (m, 4H).

LCMS (ESI+ve) m/z: 447 (M+H)$^+$, 469 (M+Na)$^+$, 893 (2M+1)$^+$; HRMS (ESI+ve) m/z calculated for C$_{22}$H$_{15}$N$_4$O$_3$S$_2$ (M+H)$^+$ 447.0580, found 447.0584.

(E)-N-(3-(1H-1,2,4-triazol-3-ylthio)-4-oxonaphthalen-1 (4H)-ylidene)-4-methylbenzenesulfonamide (13k) was prepared according to the procedure for 13x except using 12i and 3-mercapto-1,2,4-triazole, affording 57.6 mg (70.2%) title compound as a yellow solid.

$^1$H NMR (400 MHz, CD$_3$CN) δ 8.64 (br s, 1H), 8.14-8.09 (m, 2H), 7.85-7.79 (m, 3H), 7.79-7.75 (m, 2H), 7.44 (d, J=8.6 Hz, 2H), 2.45 (s, 3H).

LCMS (ESI+ve) m/z: 411 (M+H)$^+$, 433 (M+Na)$^+$, 821 (2M+H)$^+$, 843 (2M+Na)$^+$; HRMS (ESI+ve) m/z calculated for C$_{19}$H$_{15}$N$_4$O$_3$S$_2$ (M+H)$^+$ 411.0580, found 411.0582.

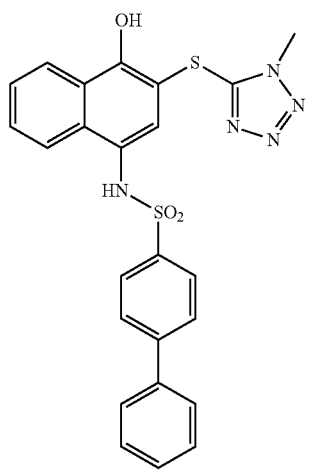

(14x)

N-(4-hydroxy-3-(1-methyl-1H-tetrazol-5-ylthio)naphthalen-1-yl)biphenyl-4-sulfonamide (14x) was prepared according to the procedure for 14d except using 13x, which afforded the title compound 33.0 mg (82.3%) as an off-white solid.

$^1$H NMR (400 MHz, CD$_2$Cl$_2$) δ 8.28 (dd, J=7.2, 2.3 Hz, 1H), 7.75 (dd, J=7.3, 2.2 Hz, 1H), 7.72 (d, J=8.5 Hz, 2H), 7.59 (d, J=8.5 Hz, 2H), 7.57-7.54 (m, 2H), 7.52-7.39 (m, 5H), 7.37 (s, 1H), 7.00 (br s, 1H), 4.00 (s, 3H).

LCMS (ESI+ve) m/z: 490 (M+H)$^+$, 492 (M+Na)$^+$; HRMS (ESI+ve) m/z calculated for C$_{24}$H$_{20}$N$_5$O$_3$S$_2$ (M+H)$^+$ 490.1002, found 490.1023.

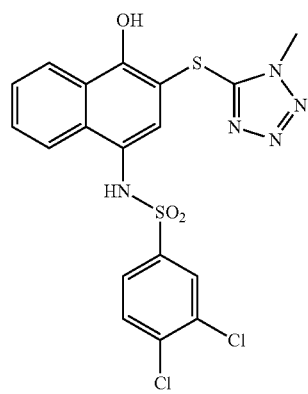

(14z)

3,4-dichloro-N-(4-hydroxy-3-(1-methyl-1H-tetrazol-5-ylthio)naphthalen-1-yl)benzenesulfonamide (14z) was prepared according to the procedure for 14d except using 13z, which afforded the title compound 39.8 mg (99.0%) as an off-white solid.

$^1$H NMR (400 MHz, CD$_2$Cl$_2$) δ 9.64 (br s, 1H), 8.32-8.26 (m, 1H), 7.99-7.93 (m, 1H), 7.83 (d, J=1.9 Hz, 1H), 7.54-7.46 (m, 3H), 7.44 (d, J=8.4 Hz, 1H), 7.14 (s, 1H), 3.96 (s, 3H).

LCMS (ESI+ve) m/z: 482 (M+H)$^+$, 504 (M+Na)$^+$; HRMS (ESI+ve) m/z calculated for C$_{18}$H$_{14}$Cl$_2$N$_5$O$_3$S$_2$ (M+H)$^+$ 481.9910, found 481.9914.

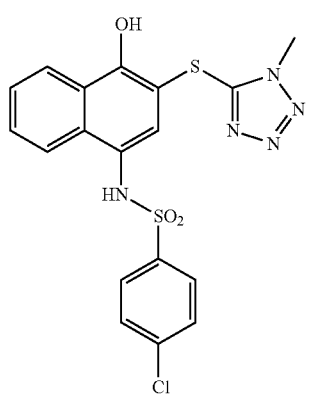

(14y)

4-chloro-N-(4-hydroxy-3-(1-methyl-1H-tetrazol-5-ylthio)naphthalen-1-yl)benzenesulfonamide (14y) was prepared according to the procedure for 14d except using 13y, which afforded the title compound 40.0 mg (99.3%) as an off-white solid.

$^1$H NMR (400 MHz, DMSO) δ 10.58 (br s, 1H), 10.12 (br s, 1H), 8.20 (d, J=8.9 Hz, 1H), 7.92 (d, J=8.9 Hz, 1H), 7.64-7.45 (m, 6H), 6.85 (s, 1H), 3.95 (s, 3H).

LCMS (ESI+ve) m/z: 448 (M+H)$^+$, 470 (M+Na)$^+$; HRMS (ESI+ve) m/z calculated for C$_{18}$H$_{15}$ClN$_5$O$_3$S$_2$ (M+H)$^+$ 448.0299, found 448.0303.

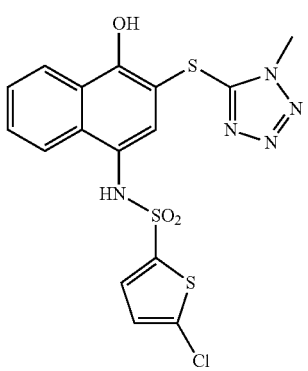

(14aa)

5-chloro-N-(4-hydroxy-3-(1-methyl-1H-tetrazol-5-ylthio)naphthalen-1-yl)thiophene-2-sulfonamide (14aa) was prepared according to the procedure for 14d except using 13aa, which afforded the title compound 40.0 mg (99.5%) as an off-white solid.

$^1$H NMR (400 MHz, CD$_2$Cl$_2$) δ 9.70 (br s, 1H), 8.33-8.27 (m, 1H), 8.02-7.97 (m, 1H), 7.57-7.48 (m, 2H), 7.23 (s, 1H), 7.09 (d, J=4.0 Hz, 1H), 6.77 (d, J=4.0 Hz, 1H), 3.97 (s, 3H).

LCMS (ESI+ve) m/z: 454 (M+H)$^+$, 476 (M+Na)$^+$; HRMS (ESI+ve) m/z calculated for C$_{16}$H$_{13}$ClN$_5$O$_3$S$_3$ (M+H)$^+$ 453.9864, found 453.9871.

(14ab)

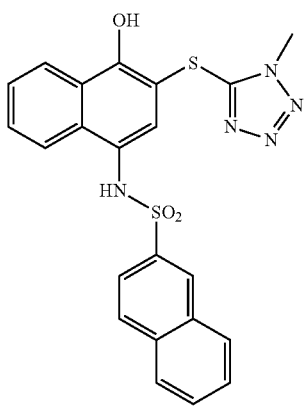

N-(4-hydroxy-3-(1-methyl-1H-tetrazol-5-ylthio)naphthalen-1-yl)benzenesulfonamide (14ac) was prepared according to the procedure for 14d except using 13ac, which afforded the title compound 35.7 mg (88.8%) as an off-white solid.

$^1$H NMR (400 MHz, CD$_2$Cl$_2$) δ 9.15 (br s, 1H), 8.67 (br s, 1H), 8.30-8.23 (m, 1H), 7.91-7.85 (m, 1H), 7.66 (d, J=7.2 Hz, 2H), 7.52-7.42 (m, 3H), 7.36 (t, J=7.7 Hz, 2H), 7.17 (s, 1H), 3.96 (s, 3H).

LCMS (ESI+ve) m/z: 414 (M+H)$^+$, 436 (M+Na)$^+$, 849 (2M+Na)$^+$; HRMS (ESI+ve) m/z calculated for C$_{18}$H$_{16}$N$_5$O$_3$S$_2$ (M+H)$^+$ 414.0689, found 414.0702.

N-(4-hydroxy-3-(1-methyl-1H-tetrazol-5-ylthio)naphthalen-1-yl)naphthalene-2-sulfonamide (14ab) was prepared according to the procedure for 14d except using 13ab, which afforded the title compound 39.0 mg (97.0%) as an off-white solid.

$^1$H NMR (400 MHz, CD$_2$Cl$_2$) δ 8.28 (apparent d, J=8.0 Hz, 1H), 8.23 (s, 1H), 7.88 (t, J=7.6 Hz, 2H), 7.82 (dd, J=7.8, 4.2 Hz, 2H), 7.71 (dd, J=8.7, 1.8 Hz, 1H), 7.65 (t, J=7.5 Hz, 1H), 7.57 (t, J=7.5 Hz, 1H), 7.46 (td, J=15.2, 6.9 Hz, 2H), 7.29 (s, 1H), 6.95 (apparent s, 1H), 3.88 (s, 3H).

LCMS (ESI+ve) m/z: 464 (M+H)$^+$, 486 (M+Na)$^+$; HRMS (ESI+ve) m/z calculated for C$_{22}$H$_{18}$N$_5$O$_3$S$_2$ (M+H)$^+$ 464.0846, found 464.0863.

(14ac)

N-(4-hydroxy-3-(1-methyl-1H-tetrazol-5-ylthio)naphthalen-1-yl)-4-methylbenzenesulfonamide (14ad) was prepared according to the procedure for 14d except using 13ad, which afforded the title compound 35.7 mg (88.8%) as an off-white solid.

$^1$H NMR (400 MHz, CD$_2$Cl$_2$) δ 9.17 (br s, 1H), 8.58 (s, 1H), 8.31-8.23 (m, 1H), 7.96-7.88 (m, 1H), 7.53 (d, J=8.3 Hz, 2H), 7.52-7.45 (m, 2H), 7.17 (s, 1H), 7.16 (d, J=8.5 Hz, 3H), 3.94 (s, 3H), 2.35 (s, 3H).

LCMS (ESI+ve) m/z: 428 (M+H)$^+$, 450 (M+Na)$^+$, 877 (2M+Na)$^+$; HRMS (ESI+ve) m/z calculated for C$_{19}$H$_{18}$N$_5$O$_3$S$_2$ (M+H)$^+$ 428.0846, found 428.0865.

TABLE 2

| HLM008182 and analogues (Group II) | | |
|---|---|---|
| YG2-120 (23, scheme number to be assigned) | 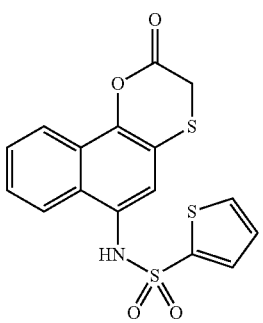 | Chemical Formula: C$_{16}$H$_{11}$NO$_4$S$_3$<br>Exact Mass: 376.98502<br>Molecular Weight: 377.45784 |

TABLE 2-continued
HLM008182 and analogues (Group II)
YG3-085
(12g in
Scheme 5)
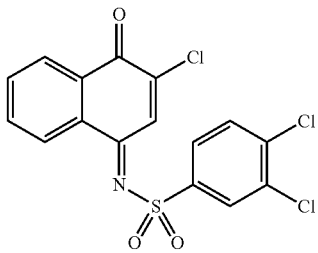
Chemical Formula:
C$_{16}$H$_8$Cl$_3$NO$_3$S
Exact Mass: 398.92905
Molecular Weight: 400.66362
YG3-087
(12h in
scheme 5)
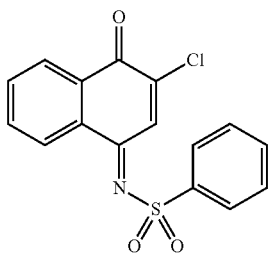
Chemical Formula:
C$_{16}$H$_{10}$ClNO$_3$S
Exact Mass: 331.00699
Molecular Weight: 331.77350
YG3-088
(12i in
scheme 5)
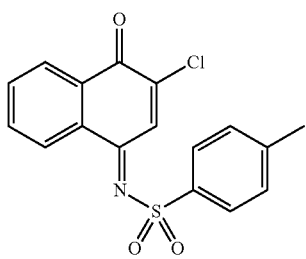
Chemical Formula:
C$_{17}$H$_{12}$ClNO$_3$S
Exact Mass: 345.02264
Molecular Weight: 345.80008
YG3-089-1
(13x in
scheme 5)
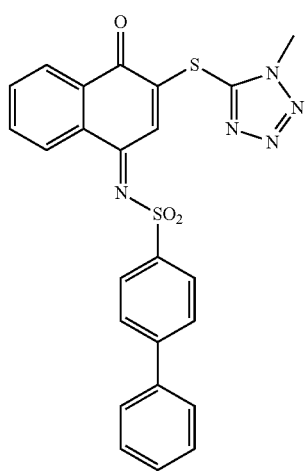
Chemical Formula:
C$_{24}$H$_{17}$N$_5$O$_3$S$_2$
Exact Mass: 487.07728
Molecular Weight: 487.55348

TABLE 2-continued

HLM008182 and analogues (Group II)

YG3-089-2
(13y in scheme 5)
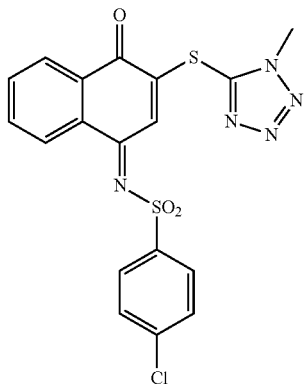
Chemical Formula:
C$_{18}$H$_{12}$ClN$_5$O$_3$S$_2$
Exact Mass: 445.00701
Molecular Weight: 445.90258

YG3-089-3
(13z in scheme 5)
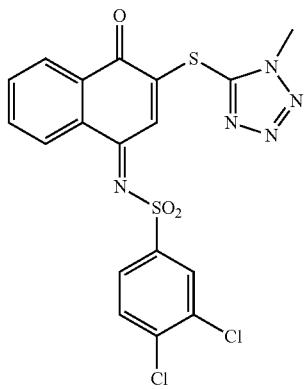
Chemical Formula:
C$_{18}$H$_{11}$Cl$_2$N$_5$O$_3$S$_2$
Exact Mass: 478.96804
Molecular Weight: 480.34764

YG3-089-4
(13aa in scheme 5)
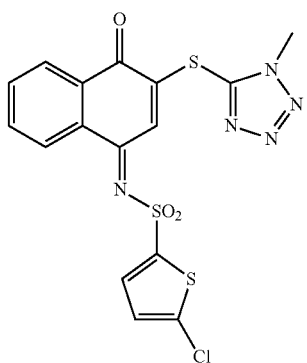
Chemical Formula:
C$_{16}$H$_{10}$ClN$_5$O$_3$S$_3$
Exact Mass: 450.96343
Molecular Weight: 451.93030

YG3-089-5
(13ab in scheme 5)
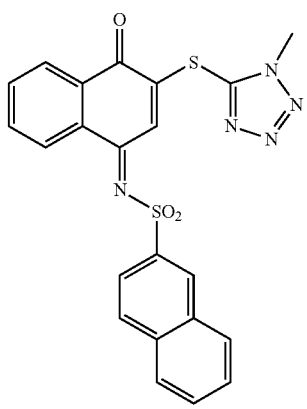
Chemical Formula:
C$_{22}$H$_{15}$N$_5$O$_3$S$_2$
Exact Mass: 461.06163
Molecular Weight: 461.51620

TABLE 2-continued
HLM008182 and analogues (Group II)
| | | |
|---|---|---|
| YG3-089-6 (13ac in scheme 5) | 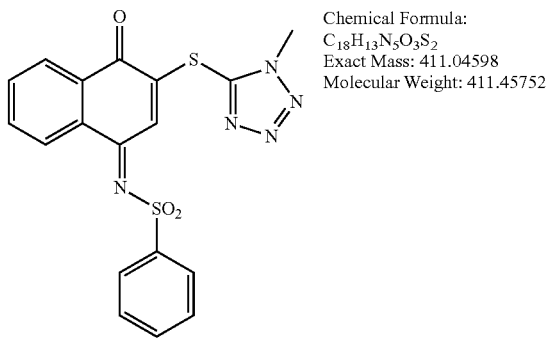 | Chemical Formula: $C_{18}H_{13}N_5O_3S_2$<br>Exact Mass: 411.04598<br>Molecular Weight: 411.45752 |
| YG3-089-7 (13ad in scheme 5) | 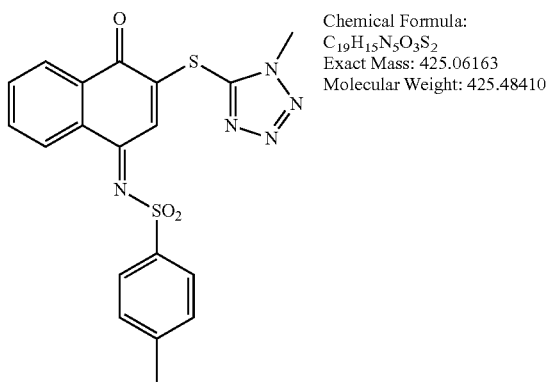 | Chemical Formula: $C_{19}H_{15}N_5O_3S_2$<br>Exact Mass: 425.06163<br>Molecular Weight: 425.48410 |
| YG3-095-1 (13ae in scheme 5) | 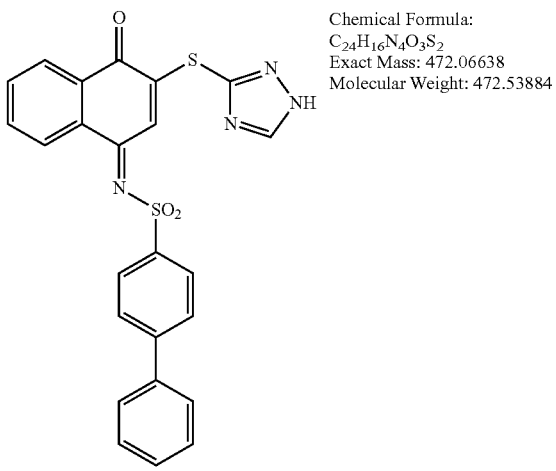 | Chemical Formula: $C_{24}H_{16}N_4O_3S_2$<br>Exact Mass: 472.06638<br>Molecular Weight: 472.53884 |
| YG3-095-2 (13af in scheme 5) | 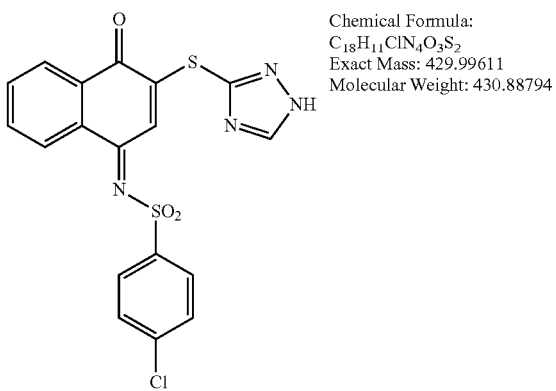 | Chemical Formula: $C_{18}H_{11}ClN_4O_3S_2$<br>Exact Mass: 429.99611<br>Molecular Weight: 430.88794 |

TABLE 2-continued

HLM008182 and analogues (Group II)

YG3-095-3
(13ag in scheme 5)
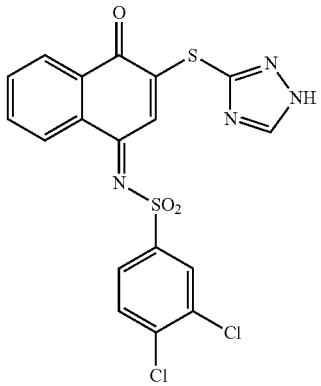 [SMILES: O=C1C(Sc2nc[nH]n2)=C/C(=N\S(=O)(=O)c2ccc(Cl)c(Cl)c2)c2ccccc21]
Chemical Formula:
C$_{18}$H$_{10}$Cl$_2$N$_4$O$_3$S$_2$
Exact Mass: 463.95714
Molecular Weight: 465.33300

YG3-095-4
(13ah in scheme 5)
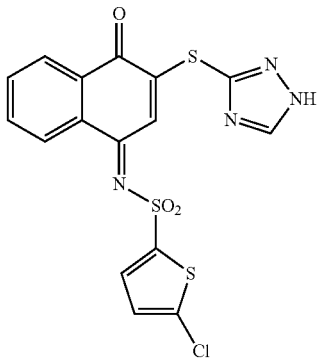 [SMILES: O=C1C(Sc2nc[nH]n2)=C/C(=N\S(=O)(=O)c2ccc(Cl)s2)c2ccccc21]
Chemical Formula:
C$_{16}$H$_9$ClN$_4$O$_3$S$_3$
Exact Mass: 435.95253
Molecular Weight: 436.91566

YG3-095-5
(13ai in scheme 5)
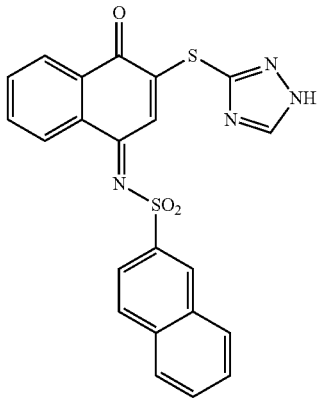 [SMILES: O=C1C(Sc2nc[nH]n2)=C/C(=N\S(=O)(=O)c2ccc3ccccc3c2)c2ccccc21]
Chemical Formula:
C$_{22}$H$_{14}$N$_4$O$_3$S$_2$
Exact Mass: 446.05073
Molecular Weight: 446.50156

YG3-095-6
(13aj in scheme 5)
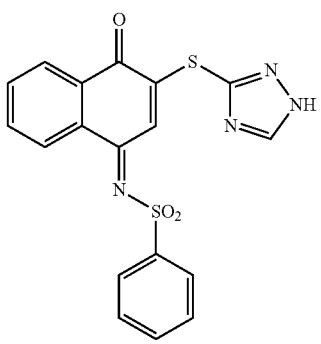 [SMILES: O=C1C(Sc2nc[nH]n2)=C/C(=N\S(=O)(=O)c2ccccc2)c2ccccc21]
Chemical Formula:
C$_{18}$H$_{12}$N$_4$O$_3$S$_2$
Exact Mass: 396.03508
Molecular Weight: 396.44288

TABLE 2-continued
HLM008182 and analogues (Group II)
YG3-095-7
(13ak in scheme 5)
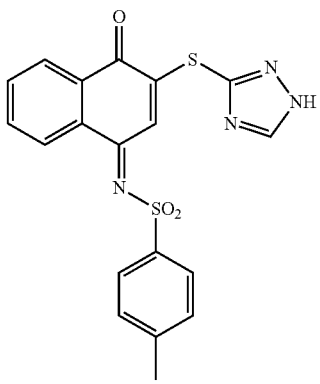 [SMILES: Cc1ccc(S(=O)(=O)/N=C2\C=C(Sc3nc[nH]n3)C(=O)c3ccccc32)cc1]
Chemical Formula: $C_{19}H_{14}N_4O_3S_2$
Exact Mass: 410.05073
Molecular Weight: 410.46946
YG3-110-1
(14x in scheme 5)
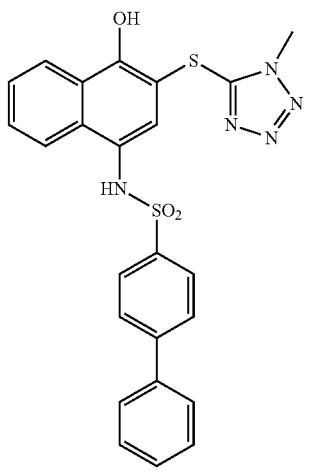 [SMILES: Cn1nnnc1Sc1cc(NS(=O)(=O)c2ccc(-c3ccccc3)cc2)c2ccccc2c1O]
Chemical Formula: $C_{24}H_{19}N_5O_3S_2$
Exact Mass: 489.09293
Molecular Weight: 489.56936
YG3-110-2
(14y in scheme 5)
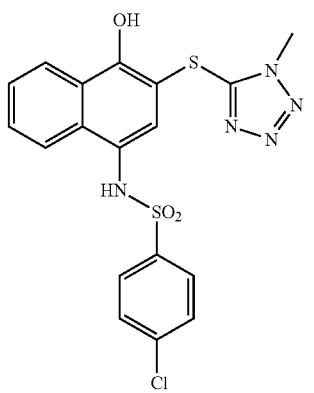 [SMILES: Cn1nnnc1Sc1cc(NS(=O)(=O)c2ccc(Cl)cc2)c2ccccc2c1O]
Chemical Formula: $C_{18}H_{14}ClN_5O_3S_2$
Exact Mass: 447.02266
Molecular Weight: 447.91846

TABLE 2-continued
HLM008182 and analogues (Group II)
YG3-110-3
(14z in scheme 5)
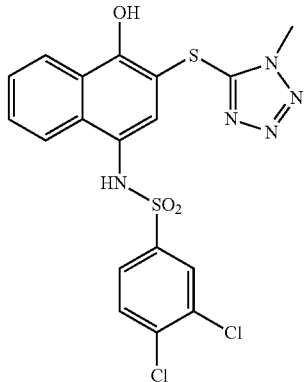 [SMILES: Cn1nnnc1Sc1cc(NS(=O)(=O)c2ccc(Cl)c(Cl)c2)c2ccccc2c1O]
Chemical Formula: $C_{18}H_{13}Cl_2N_5O_3S_2$
Exact Mass: 480.98369
Molecular Weight: 482.36352
YG3-110-4
(14aa in scheme 5)
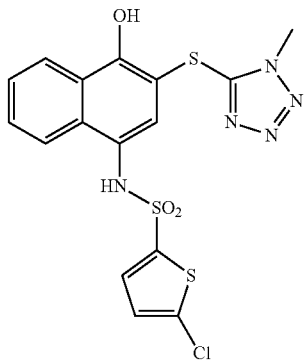 [SMILES: Cn1nnnc1Sc1cc(NS(=O)(=O)c2ccc(Cl)s2)c2ccccc2c1O]
Chemical Formula: $C_{16}H_{12}ClN_5O_3S_3$
Exact Mass: 452.97908
Molecular Weight: 453.94618
YG3-110-5
(14ab in scheme 5)
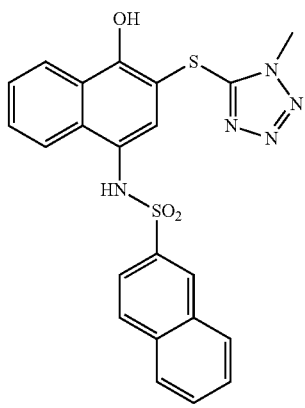 [SMILES: Cn1nnnc1Sc1cc(NS(=O)(=O)c2ccc3ccccc3c2)c2ccccc2c1O]
Chemical Formula: $C_{22}H_{17}N_5O_3S_2$
Exact Mass: 463.07728
Molecular Weight: 463.53208
YG3-110-6
(14ac in scheme 5)
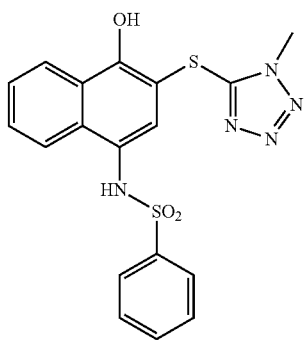 [SMILES: Cn1nnnc1Sc1cc(NS(=O)(=O)c2ccccc2)c2ccccc2c1O]
Chemical Formula: $C_{18}H_{15}N_5O_3S_2$
Exact Mass: 413.06163
Molecular Weight: 413.47340

TABLE 2-continued

HLM008182 and analogues (Group II)

YG3-110-7
(14ad in scheme 5)

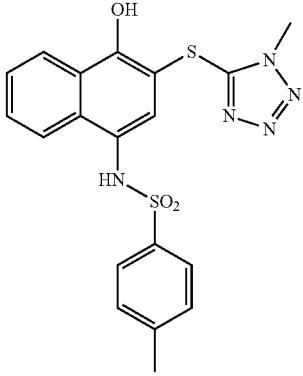 [SMILES: Cc1ccc(S(=O)(=O)Nc2cc(Sc3nnnn3C)c(O)c3ccccc23)cc1]

Chemical Formula: $C_{19}H_{17}N_5O_3S_2$
Exact Mass: 427.07728
Molecular Weight: 427.49998

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A compound having the structure shown in formula I:

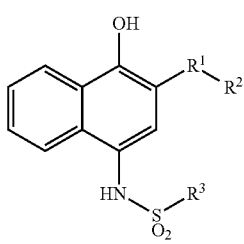

(I)

a. wherein $R^1$ is;
b. wherein $R^2$ is selected from the group consisting of alkylcarbonyl; and;
d. wherein $R^3$ is an aryl or heteroaryl then $R^3$ is selected from the group consisting of

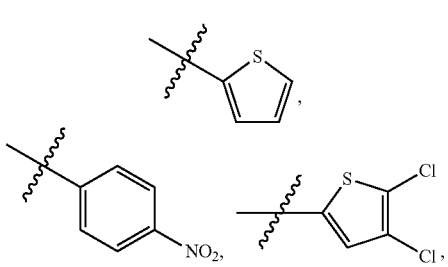

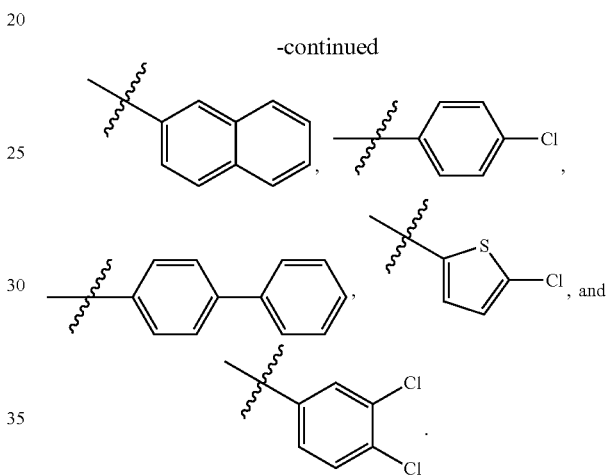

2. The compound of claim 1, wherein $R^2$ is selected from the group consisting of $CH_2COOH$, $CH_2COOC_2H_5$, $(CH_2)_2COOCH_3$, $(CH_2)_2COOH$, $(CH_2)_2CONHCH(CH_2)_2$, $CH(CH_3)COOH$, $CH_2COOH$, $CH_2COOC_2H_5$, $(CH_2)_2COOCH_3$, $(CH_2)_2COOH$, $(CH_2)_2CONHCH(CH_2)_2$.

3. The compound of claim 1, wherein when $R^2$ is $CH_2COOH$ then $R^3$ is selected from the group consisting of

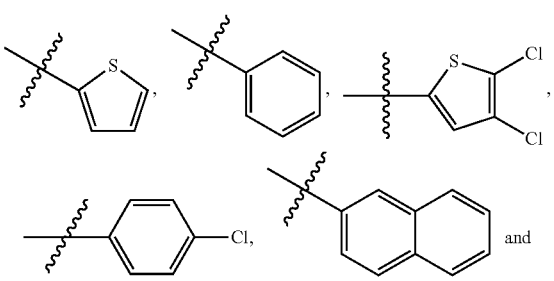

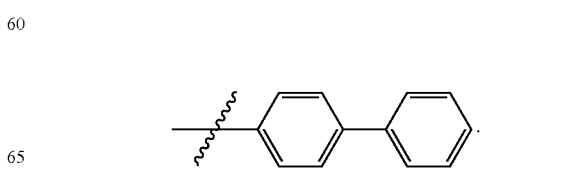

4. The compound of claim 1, wherein $R^2$ is $CH_2COOC_2H_5$ and $R^3$ is selected from the group consisting of

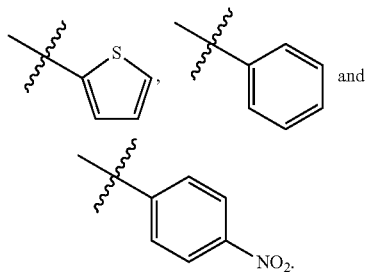

5. The compound of claim 1, wherein $R^2$ is $(CH_2)_2COOCH_3$ and $R^3$ is selected from the group consisting of

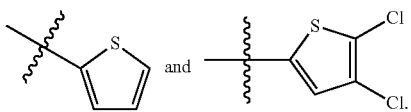 [SMILES: *c1cccs1 ; *c1cc(Cl)c(Cl)s1]

6. The compound of claim 1, wherein $R^2$ is $(CH_2)_2COOH$ and $R^3$ is

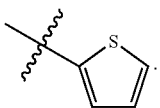

7. The compound of claim 1, wherein $R^2$ is $(CH_2)_2CONHCH(CH_2)_2$ and $R^3$ is

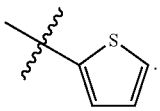

8. The compound of claim 1, wherein $R^2$ is $CH(CH_3)COOH$ and $R^3$ is selected from the group consisting of

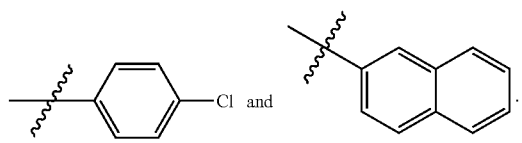 [SMILES: *c1ccc(Cl)cc1 ; "and" ; *c1ccc2ccccc2c1 ; "."]

9. The compound of claim 1, wherein the compound is selected from the group consisting of Ethyl 2-(1-oxo-4-(thiophen-2-ylsulfonylimino)-1,4-dihydronaphthalen-2-ylthio)acetate, Ethyl 2-(1-hydroxy-4-(thiophene-2-sulfonamido)naphthalen-2-ylthio)acetate, 2-(1-hydroxy-4-(thiophene-2-sulfonamido)naphthalen-2-ylthio)acetic acid, 2 (1 hydroxy-4-(thiophene-2-sulfonamido)naphthalen-2-ylthio)acetic acid, Methyl 3-(1-oxo-4-(thiophen-2-ylsulfonylimino)-1,4-dihydronaphthalen-2-ylthio)propanoate, Ethyl 2-(1-oxo-4-(phenylsulfonylimino)-1,4-dihydronaphthalen-2-ylthio)acetate, Ethyl 2-(1-oxo-4-(tosylimino)-1,4-dihydronaphthalen-2-ylthio)acetate, Ethyl 2-(4-(4-chlorobenzylsulfonylimino)-1-oxo-1,4-dihydronaphthalen-2-ylthio)-acetate, Methyl 3-(1-hydroxy-4-(thiophene-2-sulfonamido)naphthalen-2-ylthio)propanoate, Ethyl 2-(1-hydroxy-4-(phenylsulfonamido)naphthalen-2-ylthio)acetate, Ethyl 2-(1-hydroxy-4-(4-nitrophenylsulfonamido)naphthalen-2-ylthio)acetate, 3-(1-hydroxy-4-(thiophene-2-sulfonamido)naphthalen-2-ylthio)propanoic acid, 2-(1-hydroxy-4-(phenylsulfonamido)naphthalen-2-ylthio)acetic acid, N,N-dimethyl-3-(1-oxo-4-(thiophen-2-ylsulfonylimino)-1,4-dihydronaphthalen-2-ylthio)propanamide, (N-methyl-3-(1-oxo-4-(thiophen-2-ylsulfonylimino)-1,4-dihydronaphthalen-2-ylthio)propanamide, N-cyclopropyl-3-(1-oxo-4-(thiophen-2-ylsulfonylimino)-1,4-dihydronaphthalen-2-ylthio)propanamide, (Z)-2-(1-oxo-4-(thiophen-2-ylsulfonylimino)-1,4-dihydronaphthalen-2-ylthio)acetic acid, Methyl-3-(4-(4,5-dichlorothiophene-2-sulfonamido)-1-hydroxynaphthalen-2-ylthio)propanoate, 2-(4-(4,5-dichlorothiophene-2-sulfonamido)-1-hydroxynaphthalen-2-ylthio)acetic acid, 2-(4-(5-chlorothiophene-2-sulfonamido)-1-hydroxynaphthalen-2-ylthio)acetic acid, 2-(4-(4-chlorophenylsulfonamido)-1-hydroxynaphthalen-2-ylthio) acetic acid, 2-(1-hydroxy-4-(naphthalene-2-sulfonamido)naphthalen-2-ylthio)acetic acid, Ethyl 2-(4-(biphenyl-4-ylsulfonamido)-1-hydroxynaphthalen-2-ylthio)acetate, 2-(4-(biphenyl-4-ylsulfonamido)-1-hydroxynaphthalen-2-ylthio) acetic acid, 2-(4-(biphenyl-4-ylsulfonamido)-1-hydroxynaphthalen-2-ylthio)benzoic acid, 2-(4-(4-chlorophenylsulfonamido)-1-hydroxynaphthalen-2-ylthio) propanoic acid, 2-(1-hydroxy-4-(naphthalene-2-sulfonamido)naphthalen-2-ylthio)propanoic acid.

10. A compound having the structure shown in formula II:

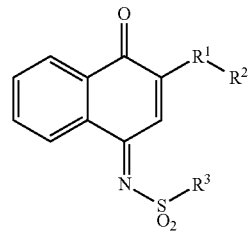

(II)

a. wherein $R^1$ is S, P, B, Cl, Br, I, heteroalkyl, heterocycloalkyl, heteroaryl, heteroarylcarbonyl, heteroaryloxycarbonyl, heterocycloalkoxy and heterocycloalkoxycarbonyl;
b. wherein $R^2$ is selected from the group consisting of alkylcarbonyl; and
d. wherein $R^3$ is an aryl or heteroaryl then $R^3$ is selected from the group consisting of

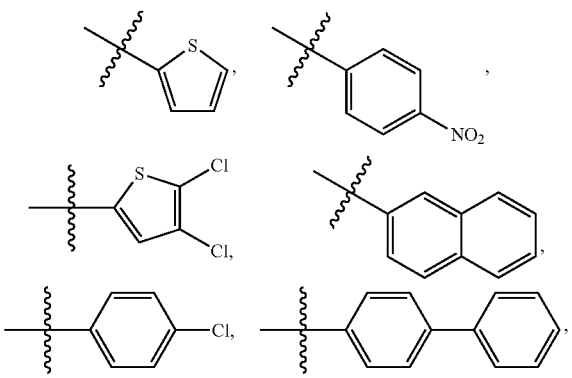

-continued

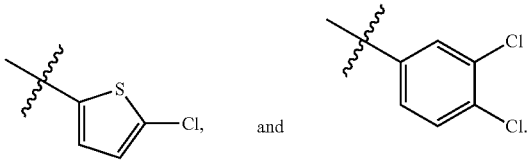
and

11. The compound of claim 10, wherein $R^2$ is selected from the group consisting of $CH_2COOH$, $CH_2COOC_2H_5$, $(CH_2)_2COOCH_3$, $(CH_2)_2COOH$, $(CH_2)_2CONHCH(CH_2)_2$, $CH(CH_3)COOH$, $CH_2COOH$, $CH_2COOC_2H_5$, $(CH_2)_2COOCH_3$, $(CH_2)_2COOH$, $(CH_2)_2CONHCH(CH_2)_2$.

12. The compound of claim 10, wherein $R^3$ is selected from the group consisting of

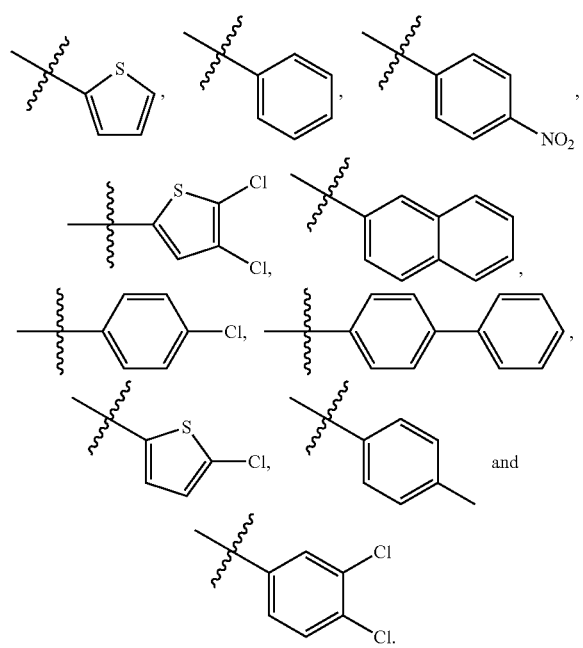

13. The compound of claim 10, wherein $R^2$ is $CH_2COOH$ and $R^3$ is selected from the group consisting of:

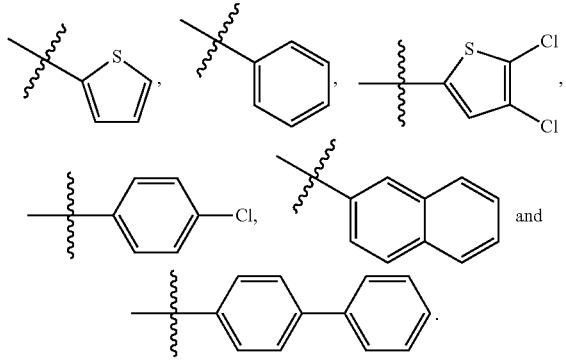

14. The compound of claim 10, wherein and $R^2$ is $CH_2COOC_2H_5$ and $R^3$ is selected from the group consisting of

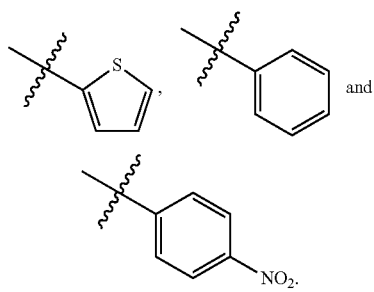
and

15. The compound of claim 10, wherein $R^2$ is $(CH_2)_2COOCH_3$ and $R^3$ is selected from the group consisting of

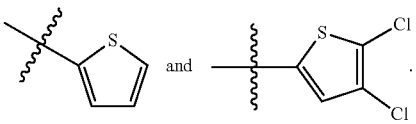 [SMILES: *c1cccs1 ; *c1cc(Cl)c(Cl)s1]

16. The compound of claim 10, wherein $R^2$ is $(CH_2)_2COOH$ and $R^3$ is

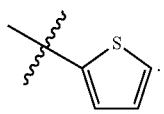 [SMILES: *c1cccs1]

17. The compound of claim 10, wherein $R^2$ is $(CH_2)_2CONHCH(CH_2)_2$ and $R^3$ is

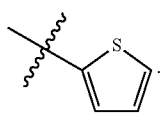 [SMILES: *c1cccs1]

18. The compound of claim 10, wherein $R^2$ is $CH(CH_3)COOH$ and $R^3$ is selected from the group consisting of

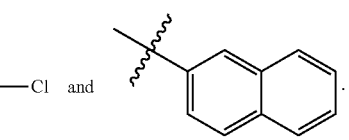

* * * * *

UNITED STATES PATENT AND TRADEMARK OFFICE
CERTIFICATE OF CORRECTION

| | | |
|---|---|---|
| PATENT NO. | : 8,466,157 B2 | Page 1 of 1 |
| APPLICATION NO. | : 13/225976 | |
| DATED | : June 18, 2013 | |
| INVENTOR(S) | : Harshani Lawrence et al. | |

It is certified that error appears in the above-identified patent and that said Letters Patent is hereby corrected as shown below:

In the Specification

Column 1, Line 13 through Line 18 should read:
GOVERNMENT SUPPORT
This invention was made with government support under grant number CA118210 awarded by the National Institutes of Health. The Government has certain rights in the invention.

Signed and Sealed this
Thirteenth Day of August, 2019

Andrei Iancu
*Director of the United States Patent and Trademark Office*